(12) United States Patent
Hitko et al.

(10) Patent No.: US 11,740,249 B2
(45) Date of Patent: *Aug. 29, 2023

(54) RECOGNITION OF CELLULAR TARGET BINDING BY A BIOACTIVE AGENT USING INTRACELLULAR BIOLUMINESCENCE RESONANCE ENERGY TRANSFER

(71) Applicant: Promega Corporation, Madison, WI (US)

(72) Inventors: Carolyn W. Hitko, Grover Beach, CA (US); Thomas Kirkland, Atascadero, CA (US); Thomas Machleidt, Madison, WI (US); Rachel Friedman Ohana, Madison, WI (US); Matt Robers, Madison, WI (US); Keith Wood, Mt. Horeb, WI (US)

(73) Assignee: Promega Corporation, Madison, WI (US)

( * ) Notice: Subject to any disclaimer, the term of this patent is extended or adjusted under 35 U.S.C. 154(b) by 1395 days.

This patent is subject to a terminal disclaimer.

(21) Appl. No.: 16/121,248

(22) Filed: Sep. 4, 2018

(65) Prior Publication Data

US 2019/0064192 A1    Feb. 28, 2019

Related U.S. Application Data

(63) Continuation of application No. 14/104,845, filed on Dec. 12, 2013, now Pat. No. 10,067,149.
(Continued)

(51) Int. Cl.
*C12Q 1/66* (2006.01)
*G01N 33/94* (2006.01)
(Continued)

(52) U.S. Cl.
CPC .............. *G01N 33/94* (2013.01); *C12Q 1/66* (2013.01); *G01N 33/542* (2013.01); *G01N 33/582* (2013.01)

(58) Field of Classification Search
CPC .... G01N 33/94; G01N 33/542; G01N 33/582; C12Q 1/66
See application file for complete search history.

(56) References Cited

U.S. PATENT DOCUMENTS 10,024,862 B2 *  7/2018  Hitko ................... G01N 33/582
10,067,149 B2 *  9/2018  Hitko ................... G01N 33/582
(Continued)

FOREIGN PATENT DOCUMENTS

CN          101962390        2/2011
WO      WO 1999/066324     12/1999
(Continued)

OTHER PUBLICATIONS

Beija et al., Synthesis and applications of Rhodamine derivatives as fluorescent probes. Chem Soc Rev. Aug. 2009;38(8):2410-33.
(Continued)

*Primary Examiner* — Louise W Humphrey
*Assistant Examiner* — Anjali Ajit Hirani
(74) *Attorney, Agent, or Firm* — Casimir Jones SC; David W. Staple

(57) ABSTRACT

Provided herein are compositions and methods for detection and analysis of intracellular binding of a bioactive agent to a cellular target. In particular, bioactive agents tethered to fluorophores, cellular targets fused to bioluminescent reporters, and methods of detecting and analyzing the interaction of bioactive agents with cellular targets therewith.

23 Claims, 34 Drawing Sheets

Specification includes a Sequence Listing.

Related U.S. Application Data

(60) Provisional application No. 61/794,461, filed on Mar. 15, 2013, provisional application No. 61/736,429, filed on Dec. 12, 2012.

(51) Int. Cl.
 G01N 33/542 (2006.01)
 G01N 33/58 (2006.01)

(56) References Cited

U.S. PATENT DOCUMENTS

| | | |
|---|---|---|
| 2006/0211045 A1 | 9/2006 | George et al. |
| 2008/0299592 A1 | 12/2008 | Miller |
| 2010/0281552 A1 | 11/2010 | Encell |
| 2012/0174242 A1 | 7/2012 | Binkowski |
| 2013/0317207 A1 | 11/2013 | Kirkland et al. |
| 2014/0194307 A1 | 7/2014 | Hitko et al. |
| 2014/0194325 A1 | 7/2014 | Hitko et al. |

FOREIGN PATENT DOCUMENTS

| | | |
|---|---|---|
| WO | WO 2001/046691 | 6/2001 |
| WO | WO 2002/029410 | 4/2002 |
| WO | WO 2004/034054 | 4/2004 |
| WO | WO 2006/086883 | 8/2006 |
| WO | WO 2010/127368 | 11/2010 |
| WO | WO 2013/078244 | 5/2013 |
| WO | WO 2014/093677 | 6/2014 |

OTHER PUBLICATIONS

Chen et al., Site-specific labeling of proteins with small molecules in live cells. Curr Opin Biotechnol. Feb. 2005;16(1):35-40.

Hall et al., Engineered Luciferase Reporter from a Deep Sea Shrimp Utilizing a Novel Imidazopyrazinone Substrate, ACS Chem Biol, 2012, 7:1848-1857, including Supplemental supporting information, 31 pages.

Paley et al., Bioluminescence: a versatile technique for imaging cellular and molecular features. Medchemcomm. Mar. 1, 2014;5(3):255-267.

Promega Corp. pGL3 Luciferase Reporter Vectors [Technical Manual]. U.S.A. Dec. 2008, 31 pages.

Stoddart et al., Application of BRET to monitor ligand binding to GPCRs. Nat Methods. Jul. 2015;12(7):661-663.

Toullec et al., The bisindolylmaleimide GF 109203X is a potent and selective inhibitor of protein kinase C, J Biol Chem 1991, 266(24): 15771-15781.

Xia et al., Biosensing and imaging based on bioluminescence resonance energy transfer. Curr Opin Biotechnol. Feb. 2009;20(1):37-44.

Zhang et al., HaloTag protein-mediated site-specific conjugation of bioluminescent proteins to quantum dots.Angew Chem Int Ed Engl. Jul. 24, 2006;45(30):4936-40.

International Search Report and Written Opinion for PCT/US2013/074765, dated Mar. 6, 2014, 10 pages.

Supplementary European Search Report for EP 13861977, dated May 20, 2016, 7 pages.

Search Report and Written Opinion for Singapore Patent Application 11201504525V, dated Sep. 9, 2016, 12 pages.

\* cited by examiner

FIG. 2A
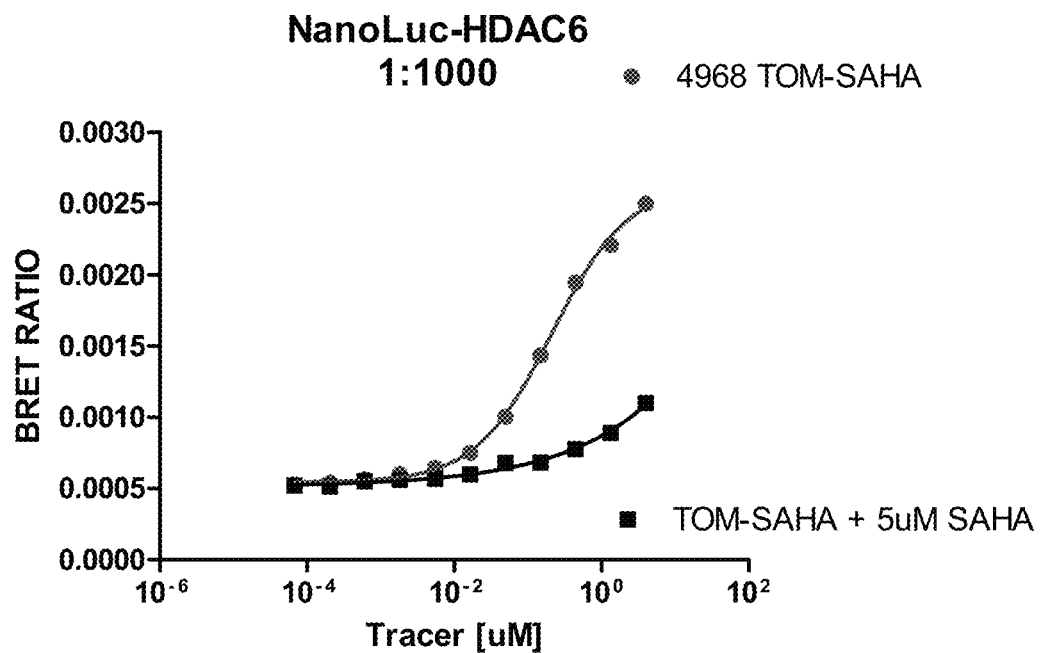
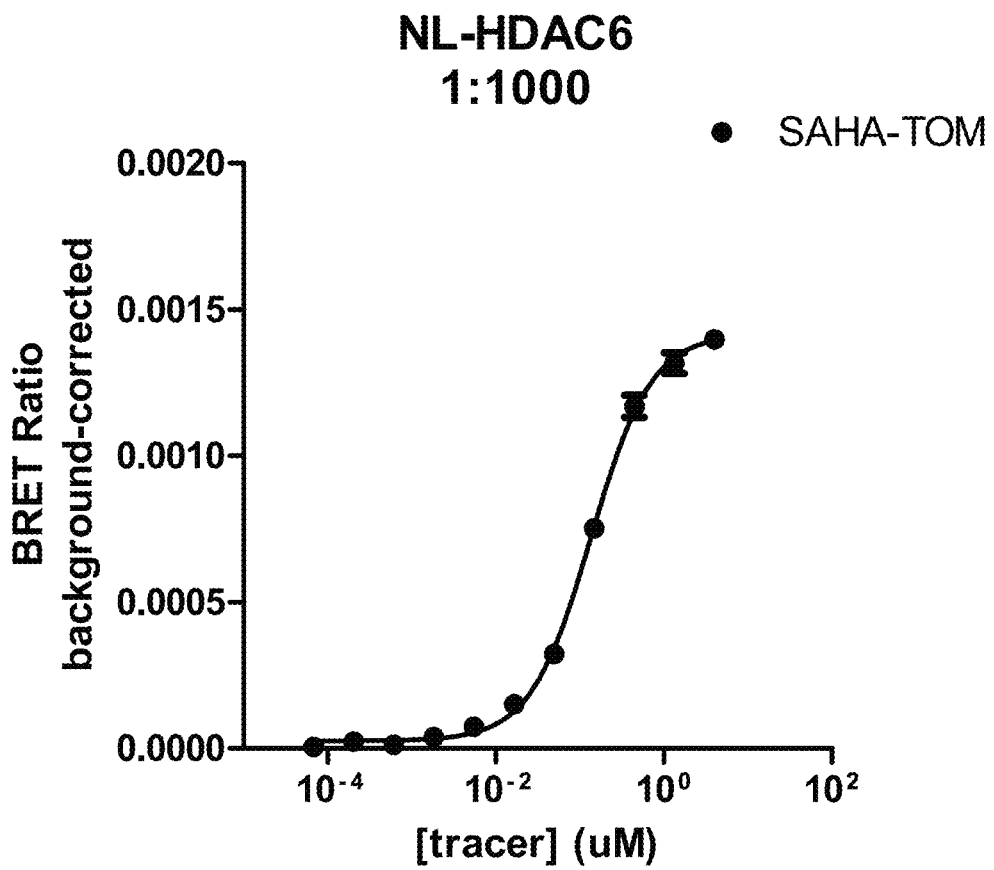

FIG. 2B
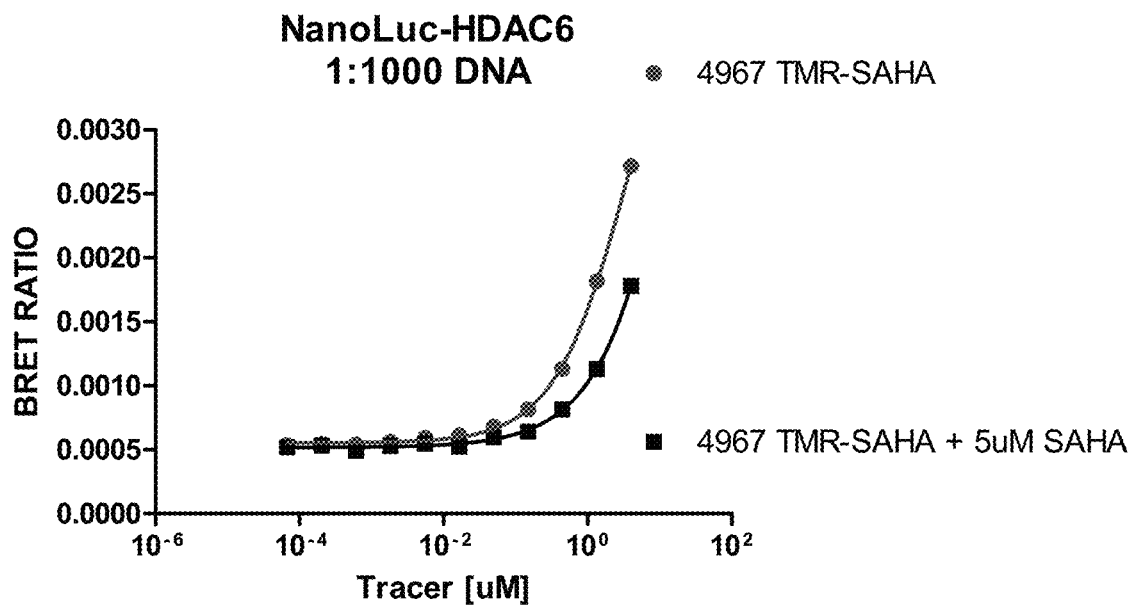
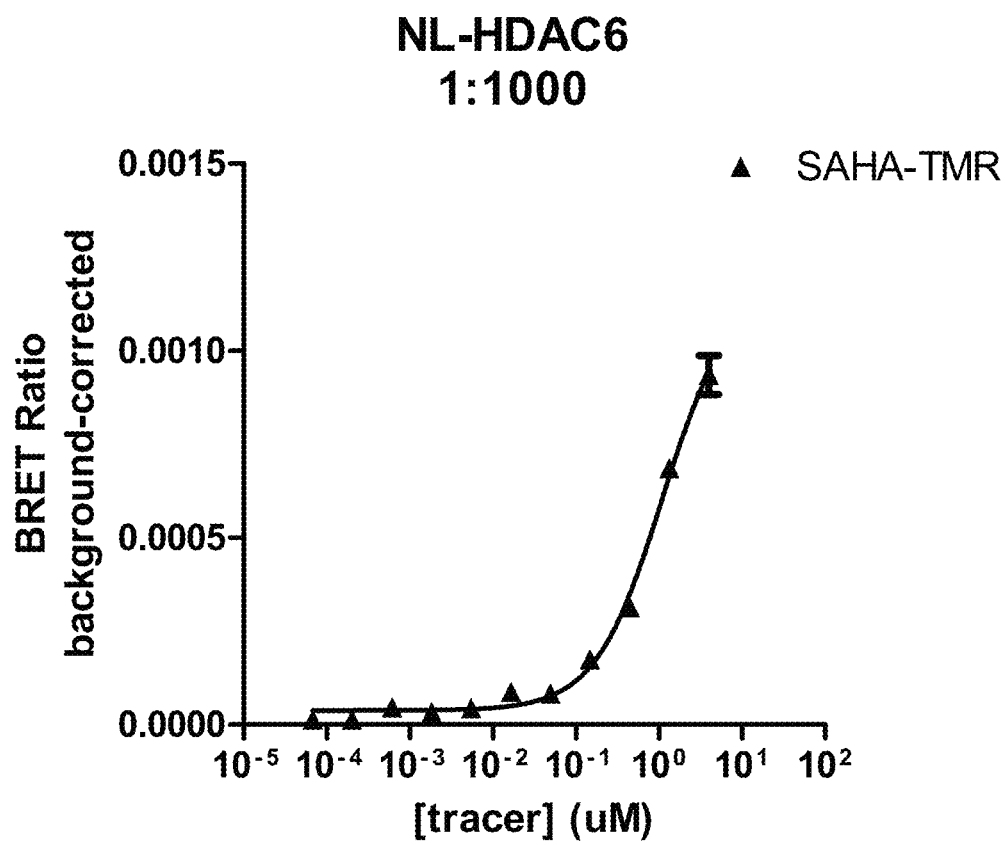

FIG. 4
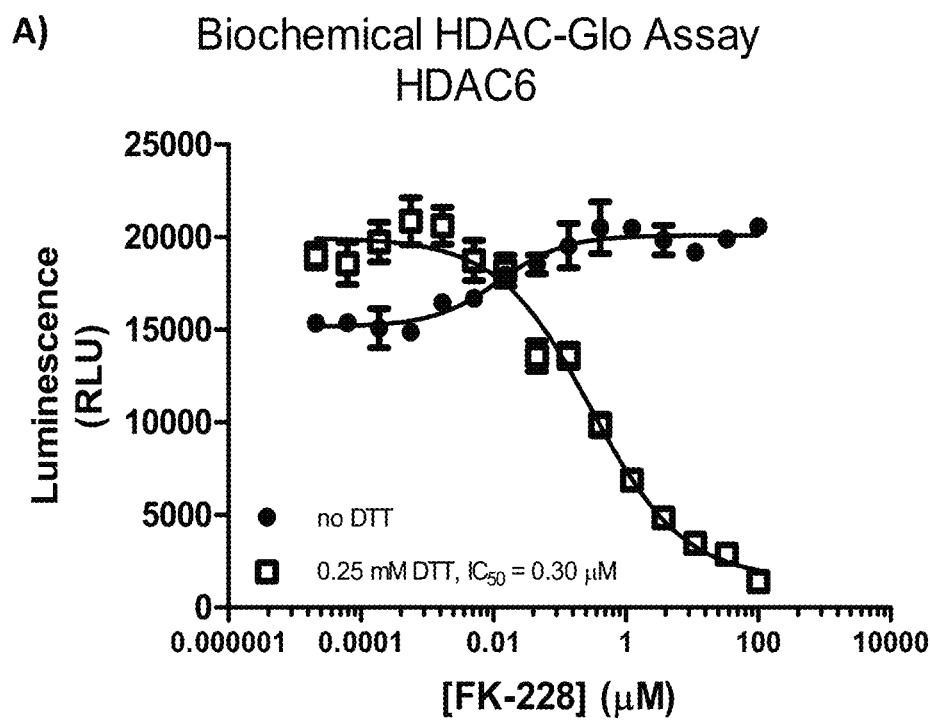
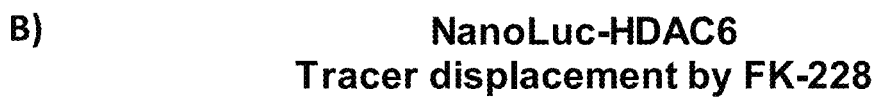

FIG. 5A
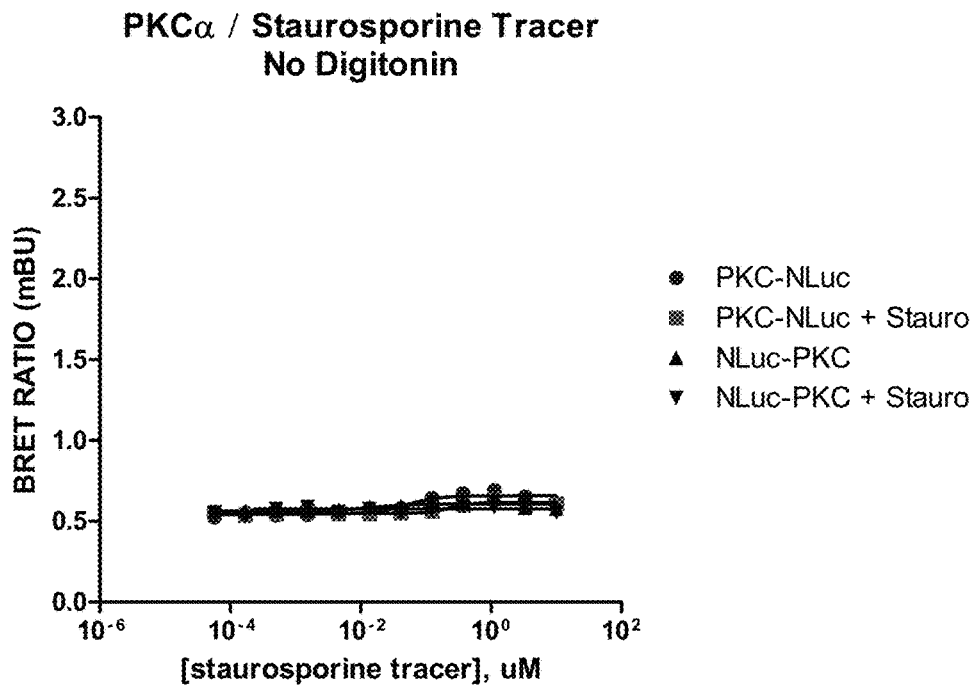
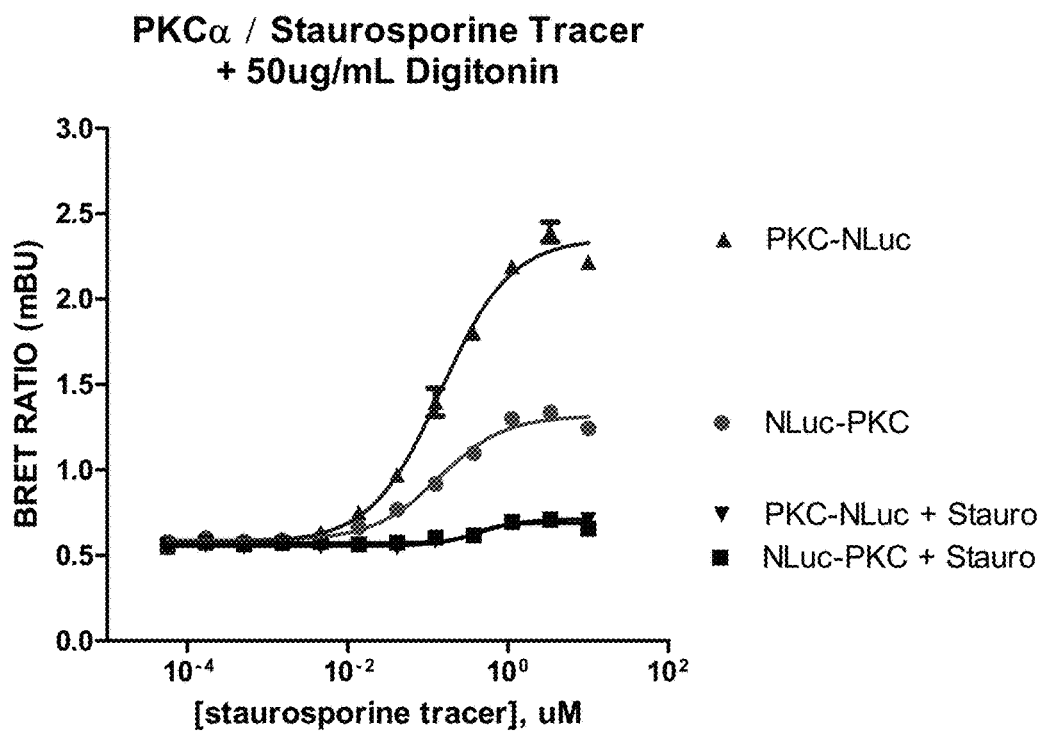
FIG. 5B

FIG. 7
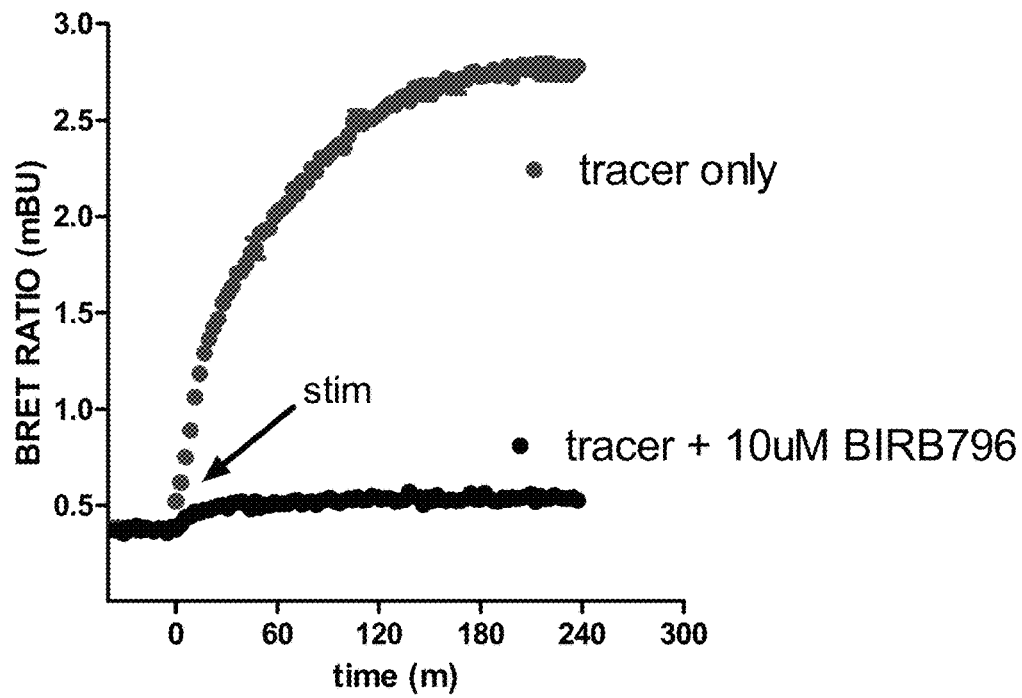
A) Kinetics of p38 Tracer Binding
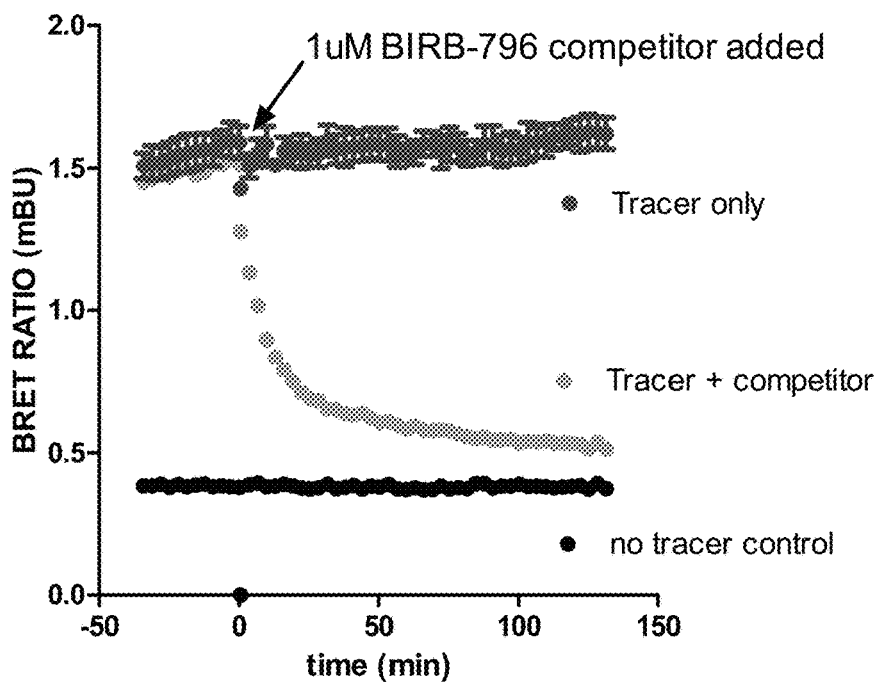
B) Kinetics of p38 Tracer Displacement

FIG. 8A
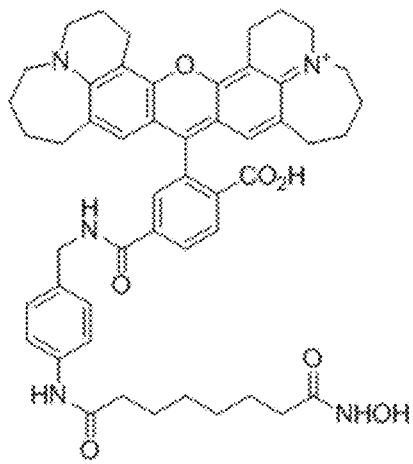
SAHA-TOM (4968)
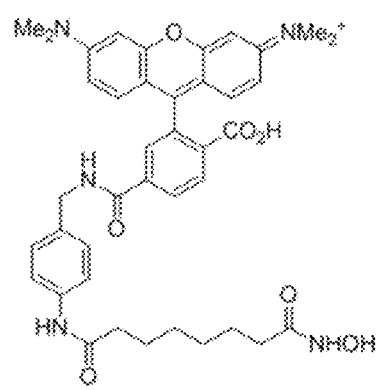
SAHA-TAMRA (4967)
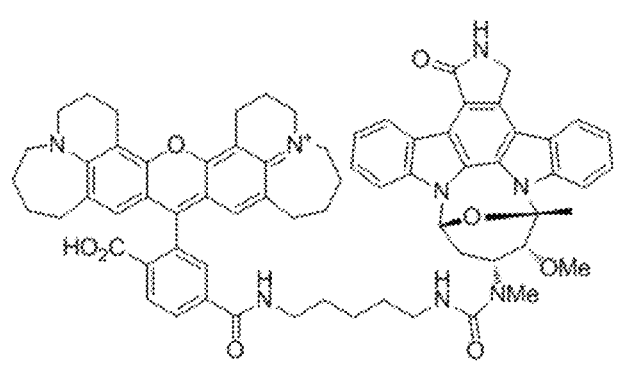
Staurosporine-TOM (5129)
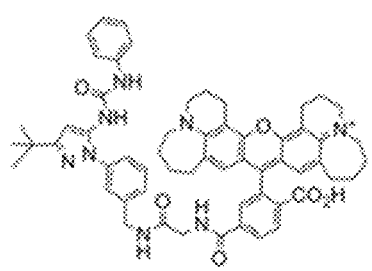
BIRB-TOM (4838)
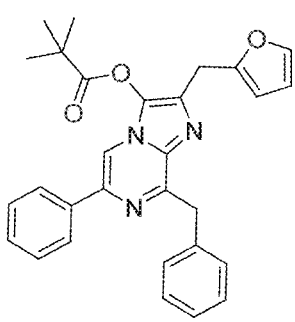
PBI 4378

FIG. 8B
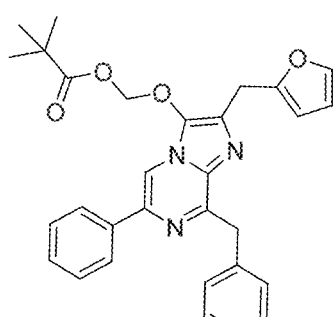
PBI 4377
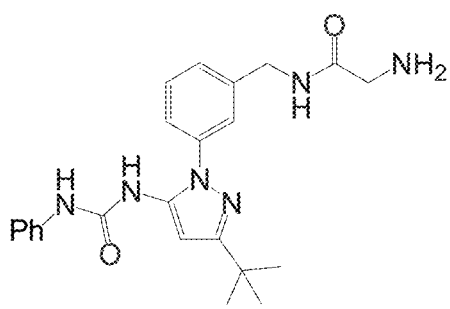
PBI 4835
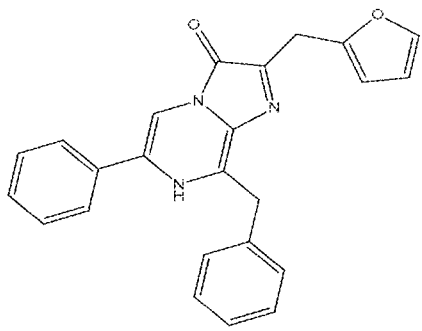
PBI-3939 (furimazine)

FIG. 10A
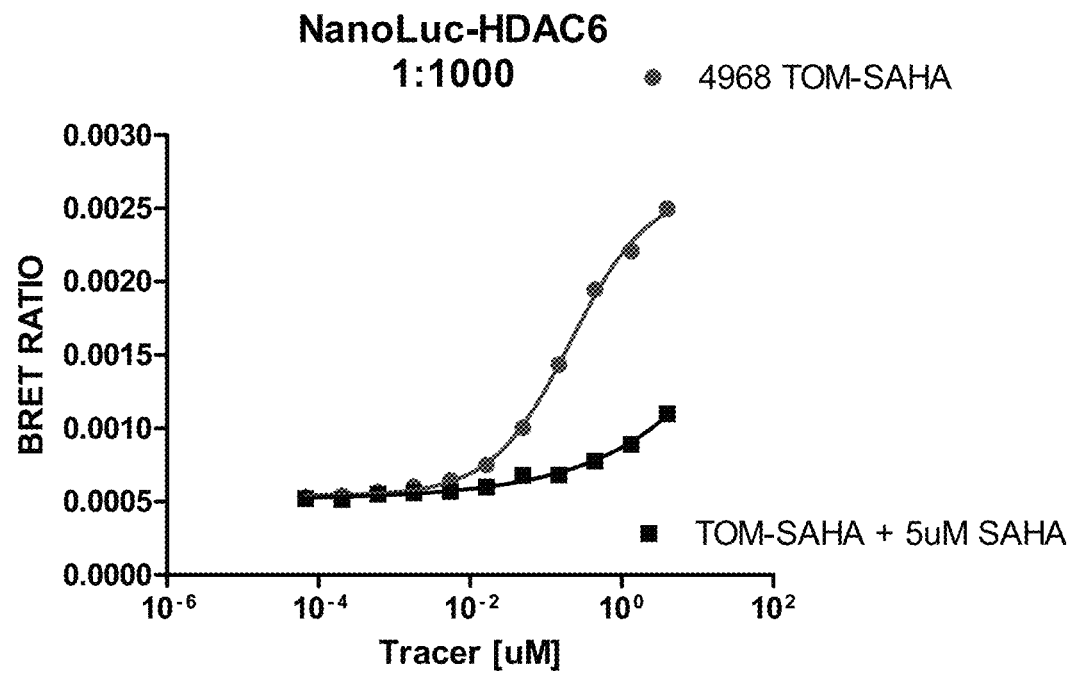
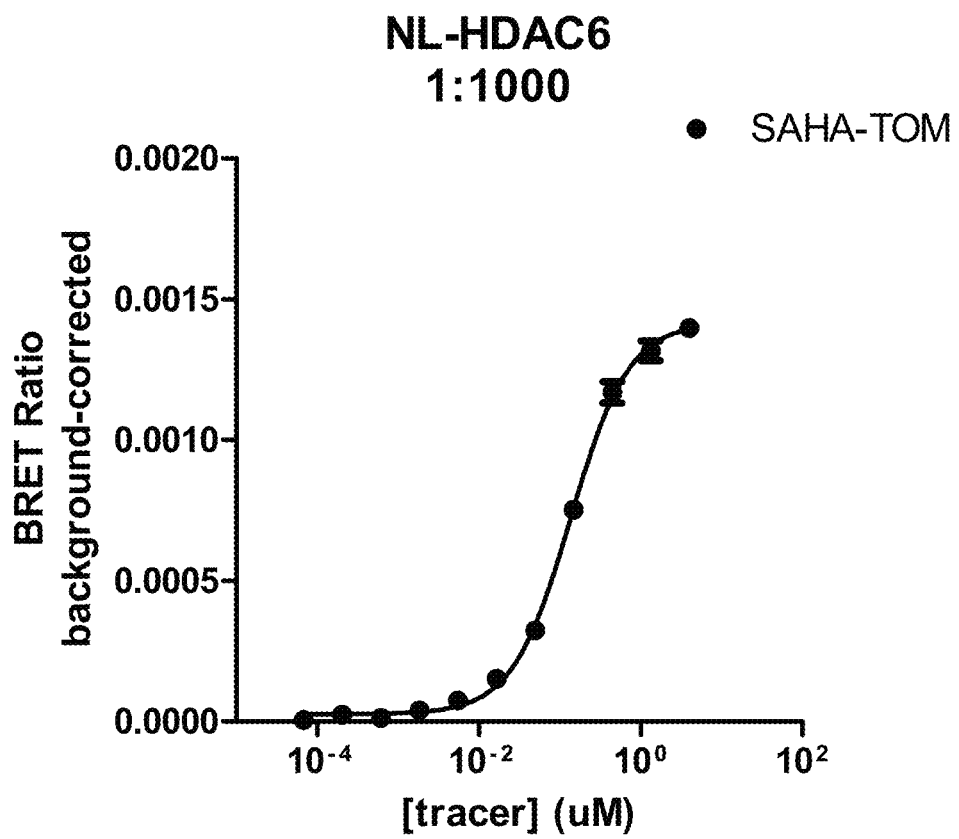

FIG. 10B
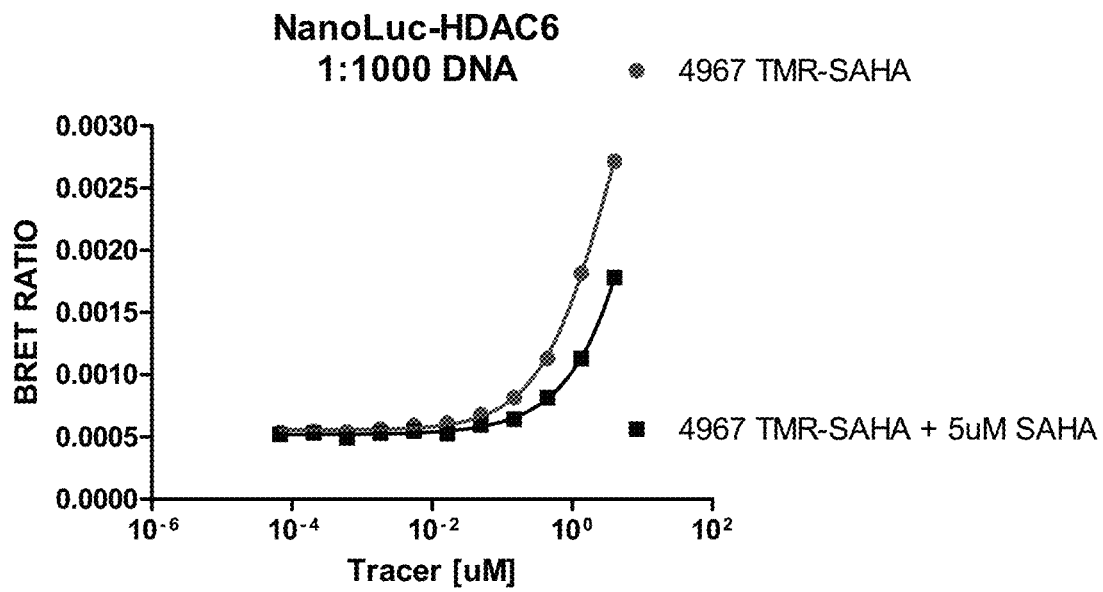
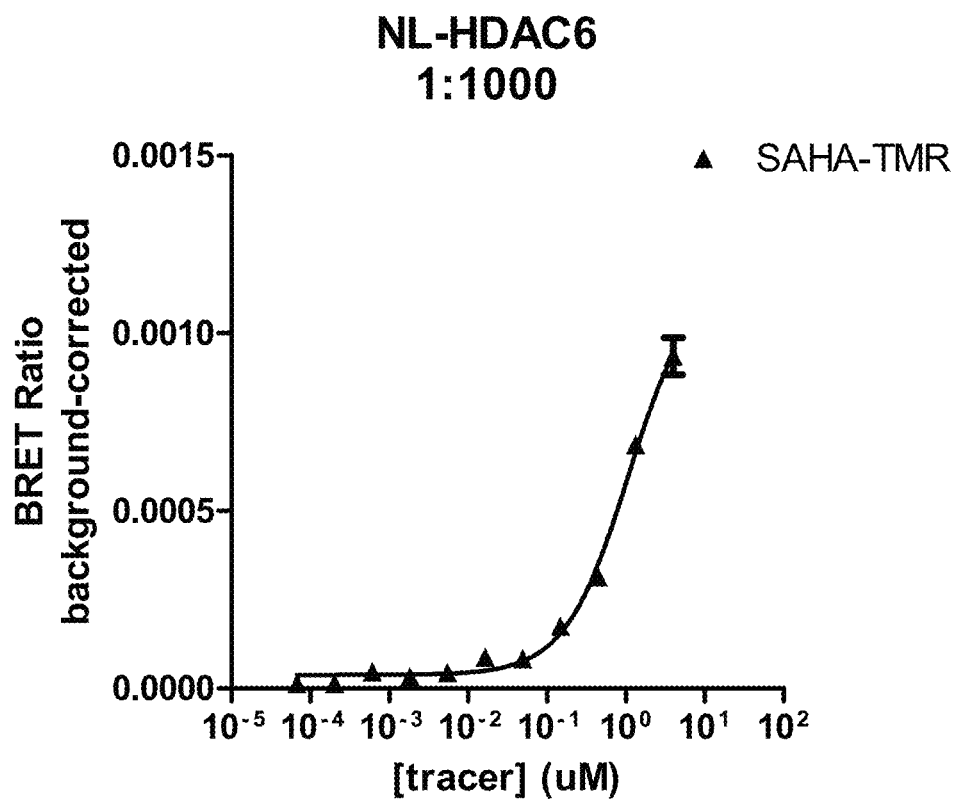

FIG. 14A
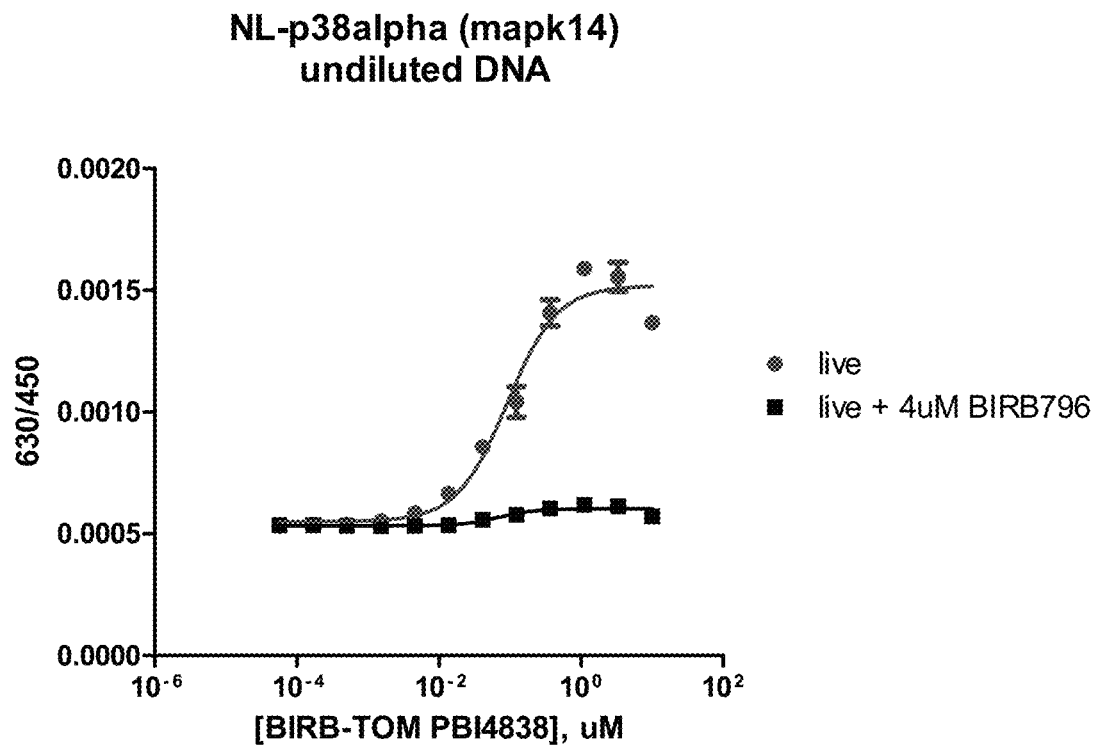
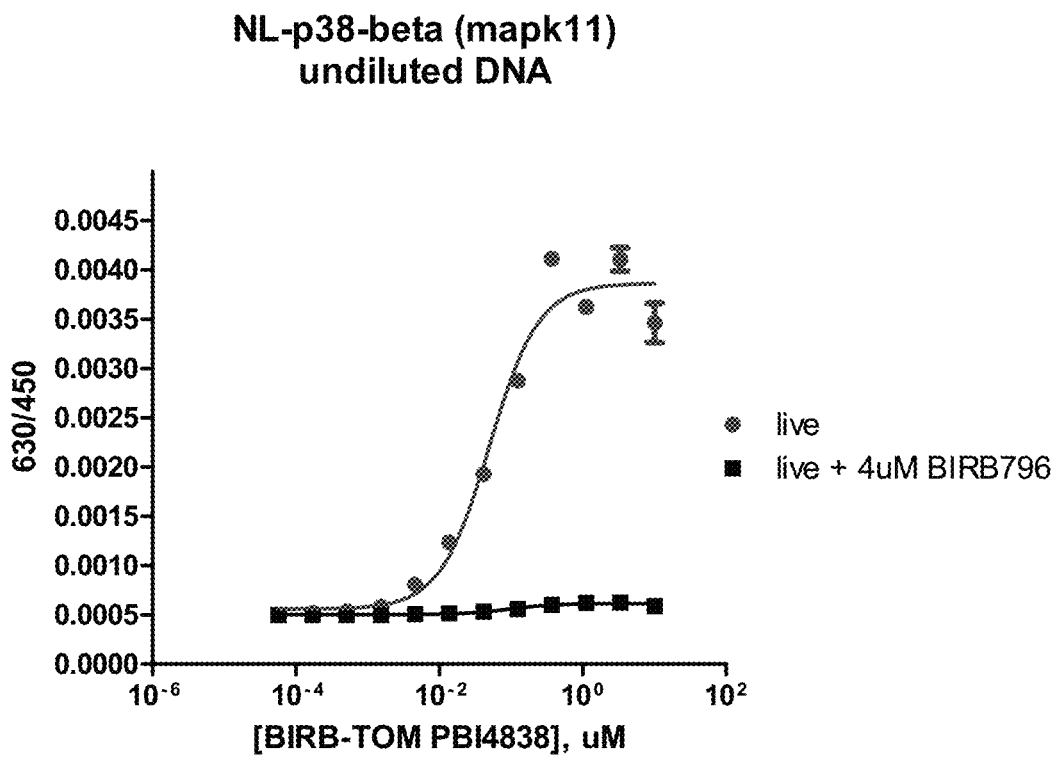

FIG. 15A
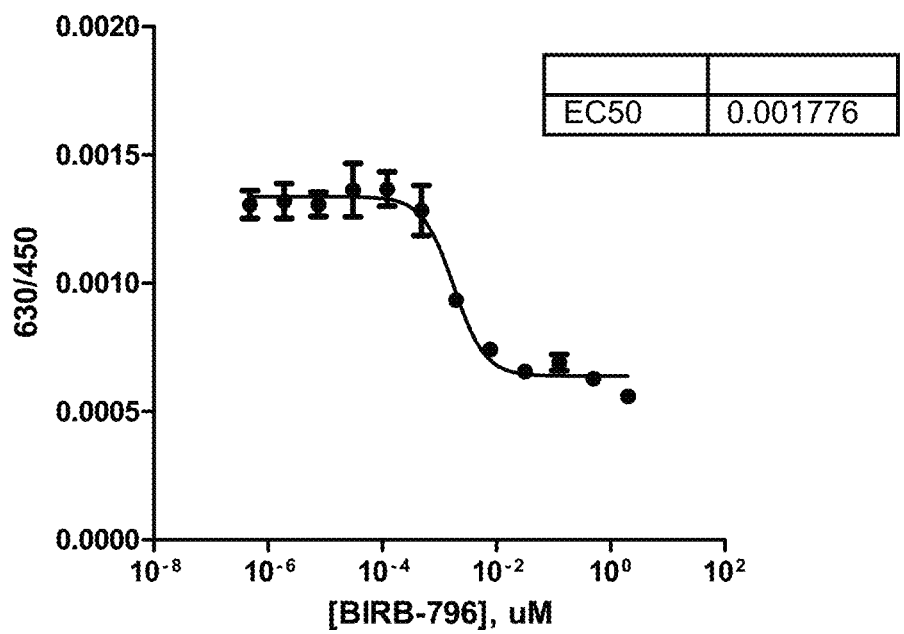
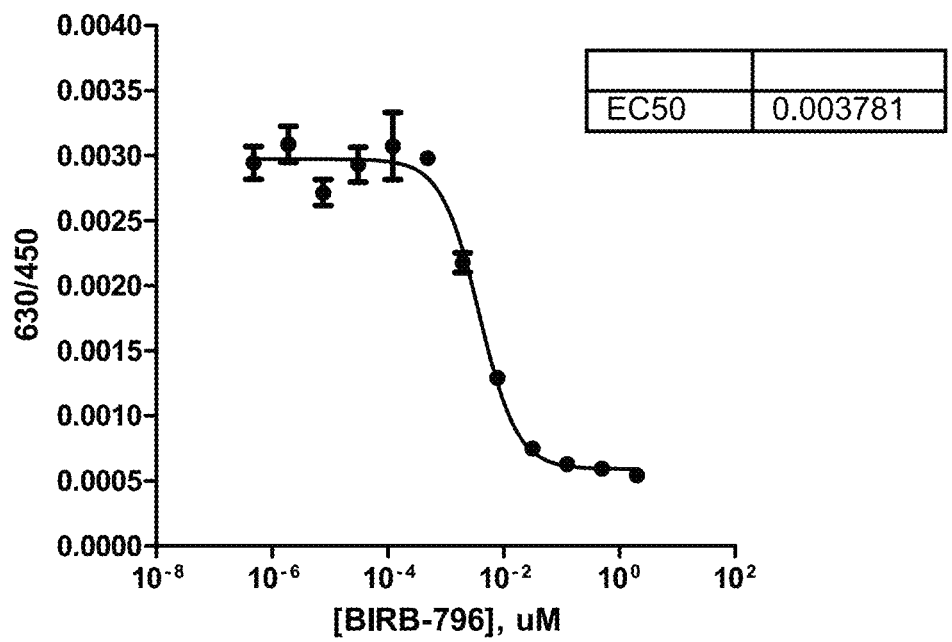

FIG. 17A
Trichostatin A
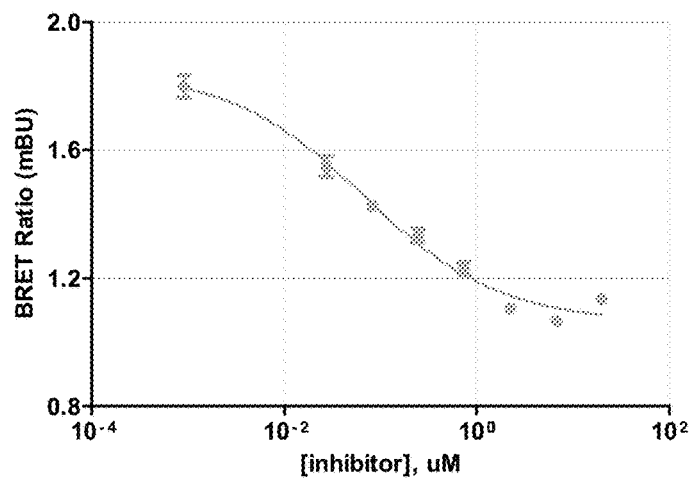
M-344
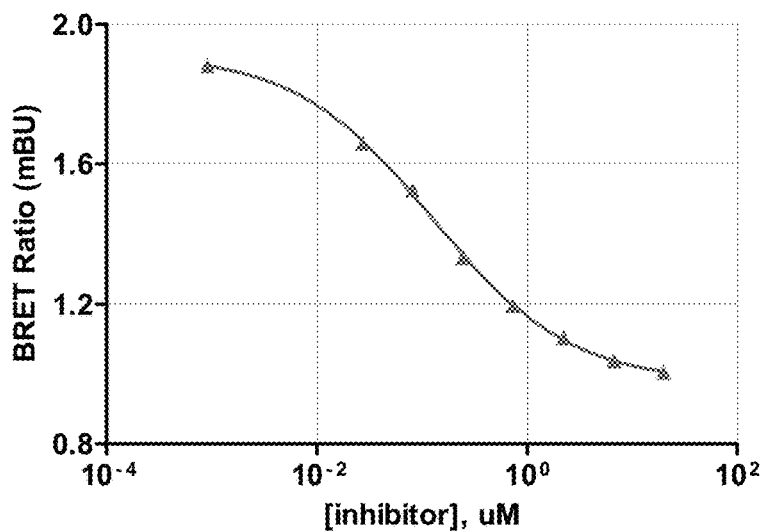
Panabinostat / LBH589
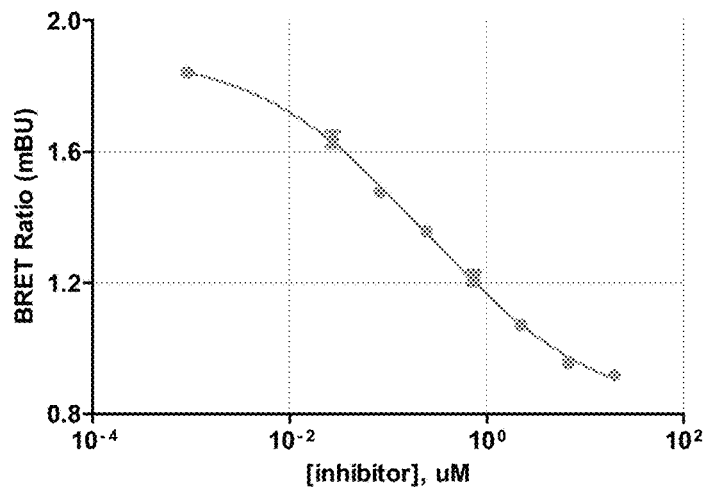

FIG. 17B
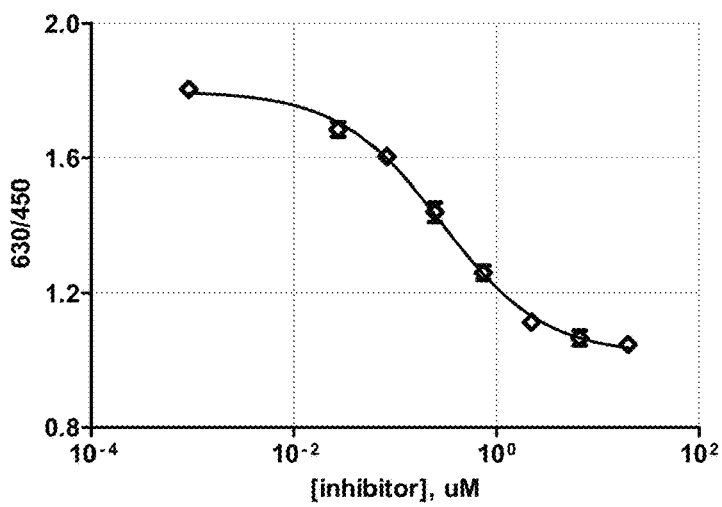
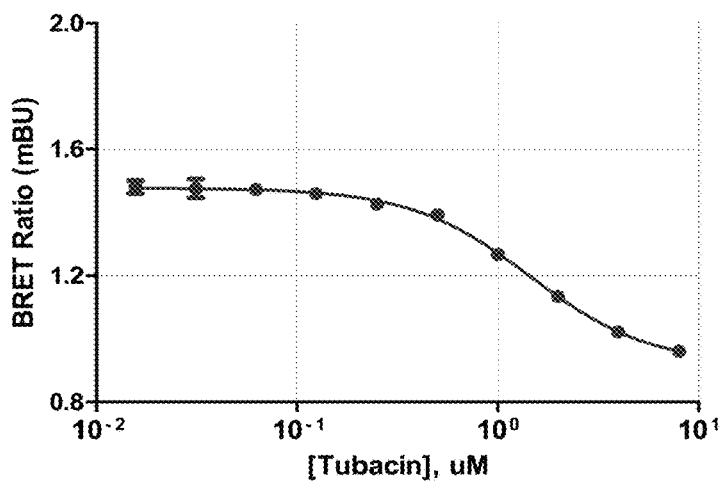
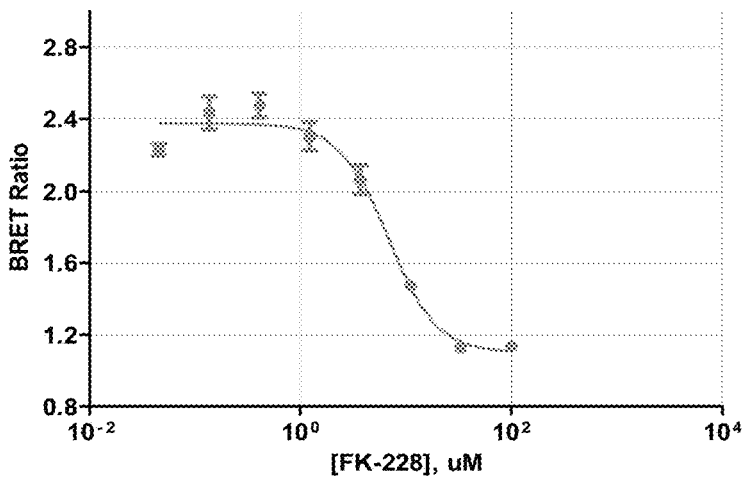

FIG. 17C
Compound 6h
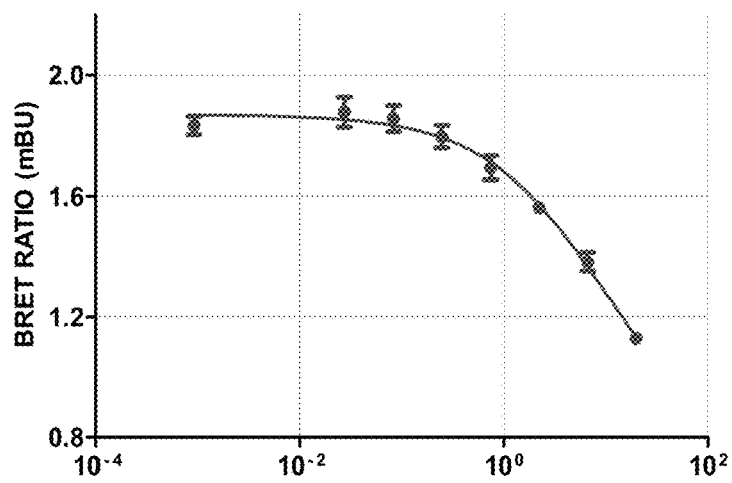
Mocetinostat
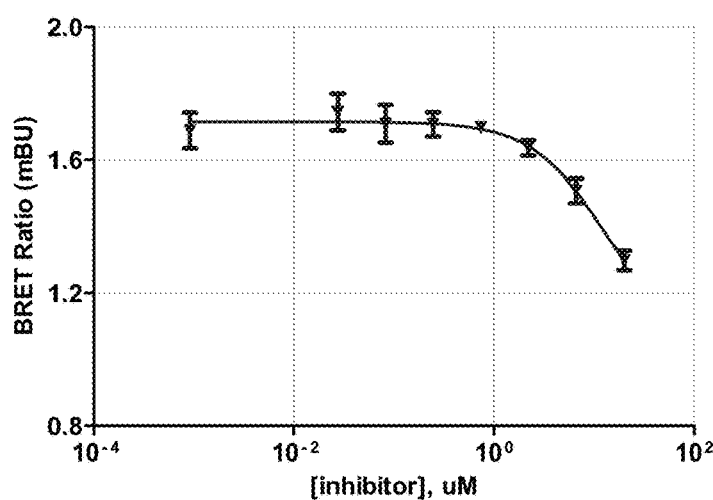
Apicidin
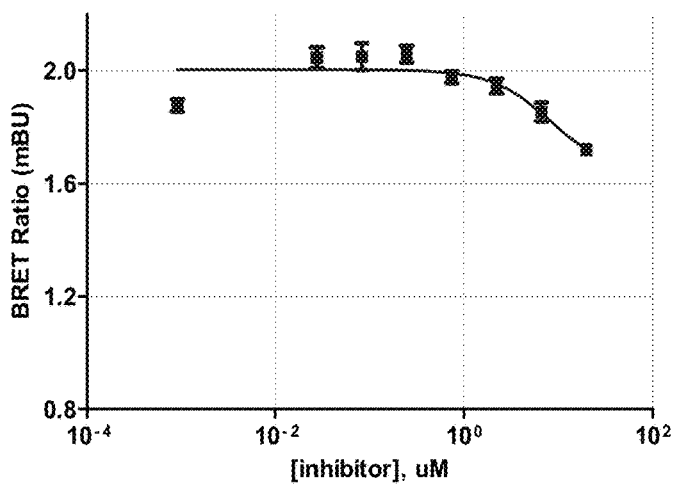

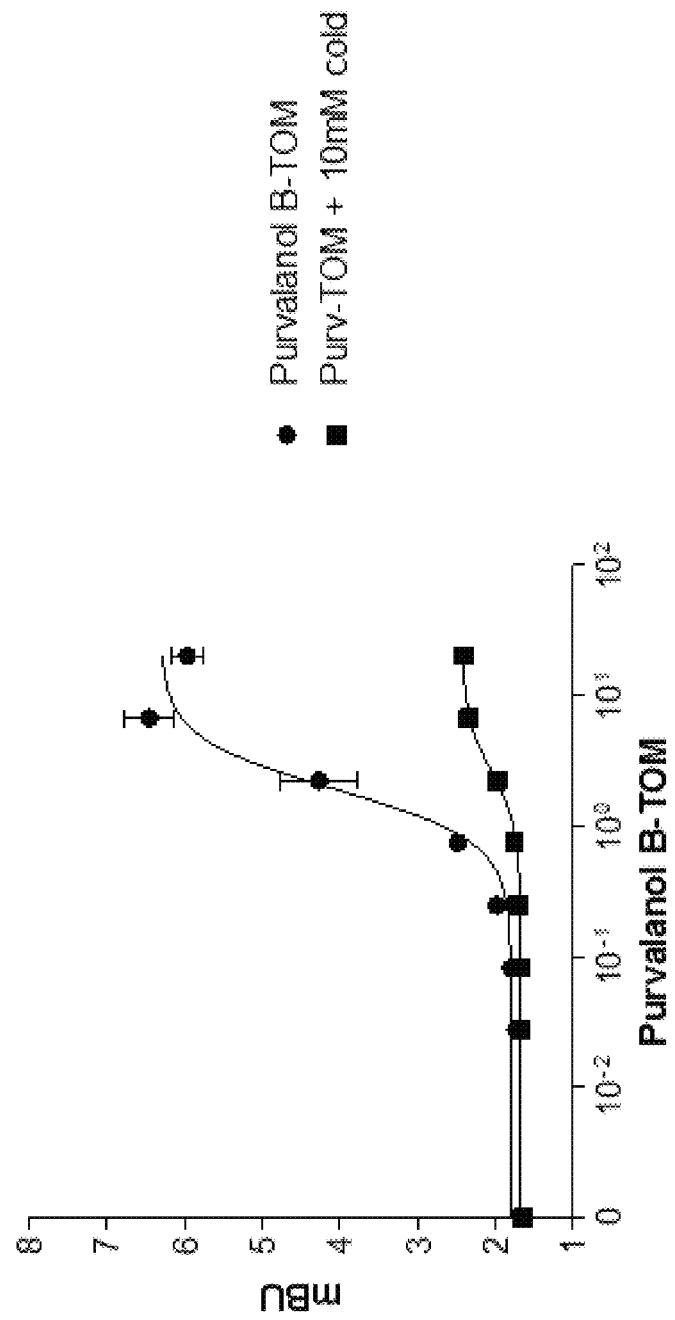

FIG. 19
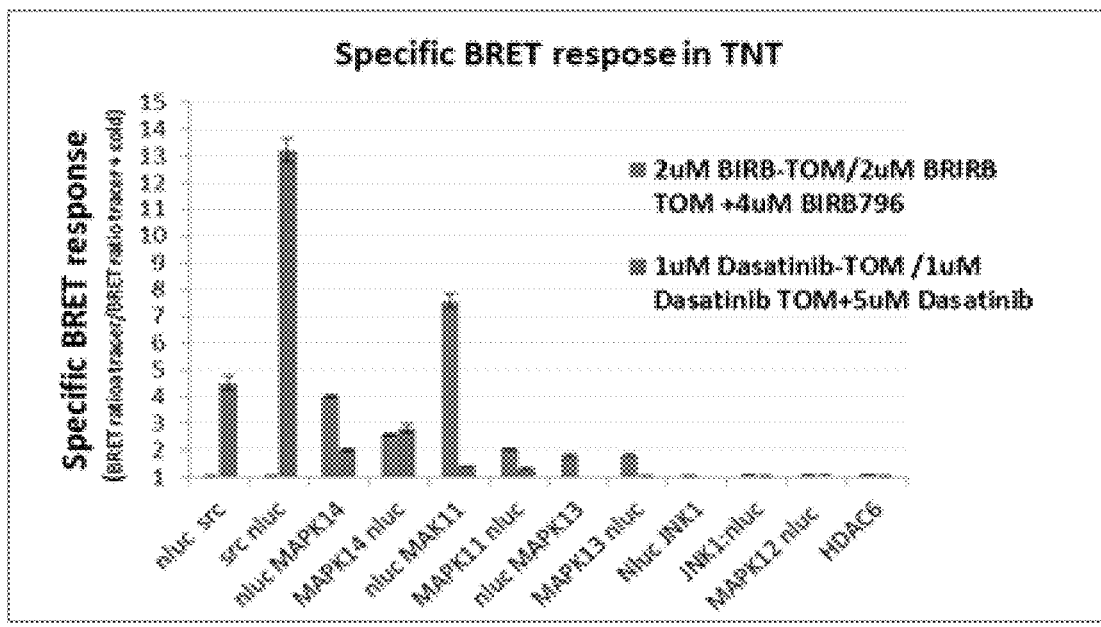
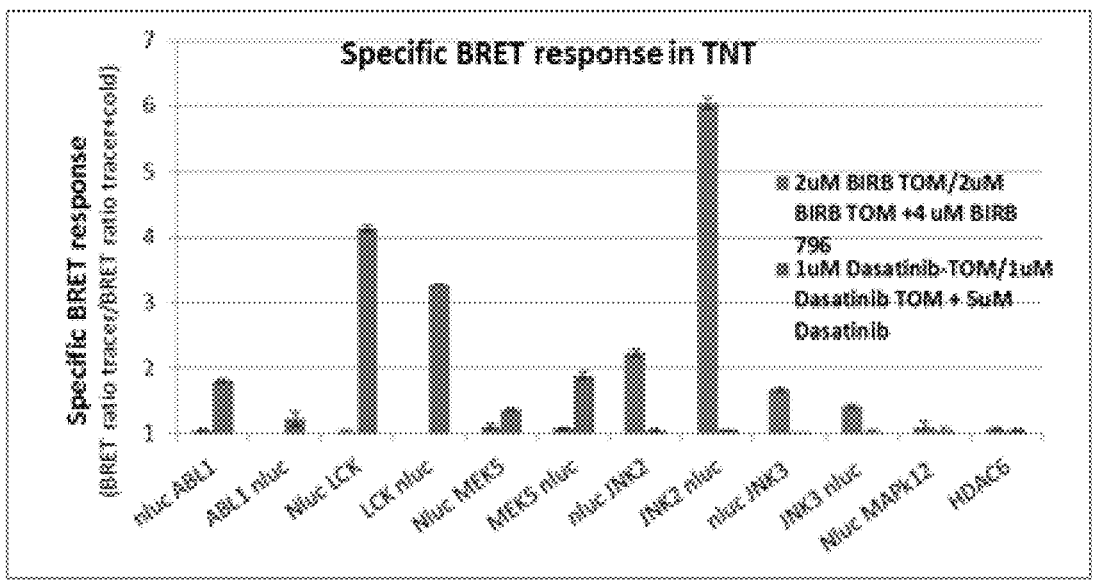

FIG. 20A
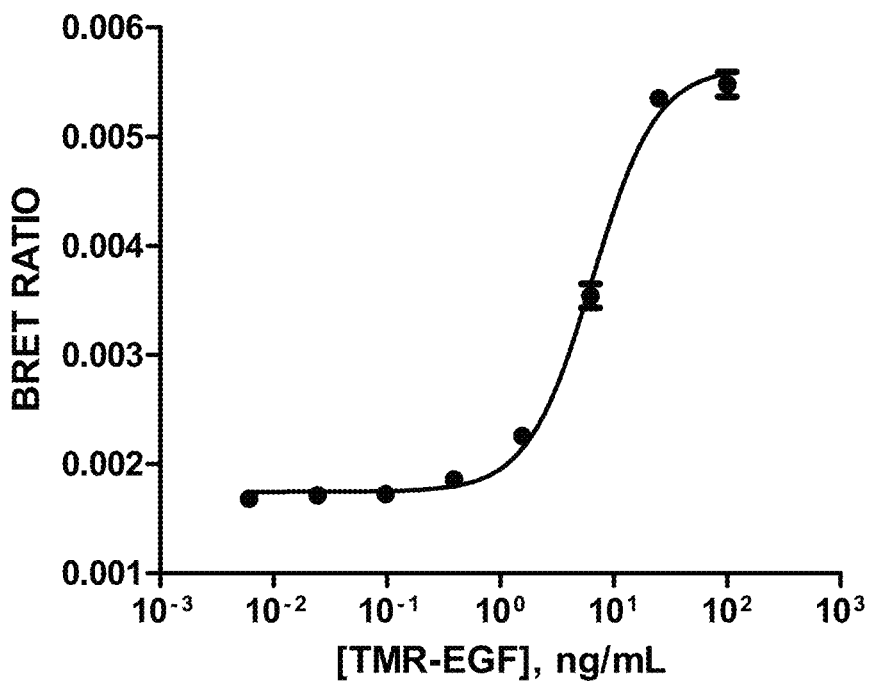
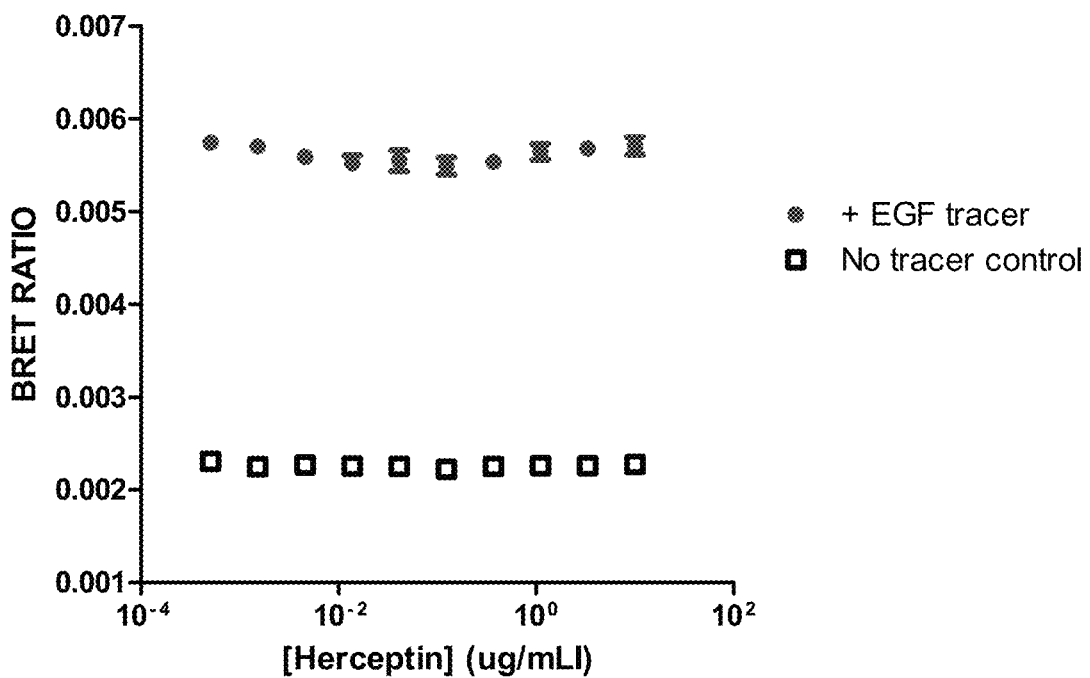

FIG. 20B
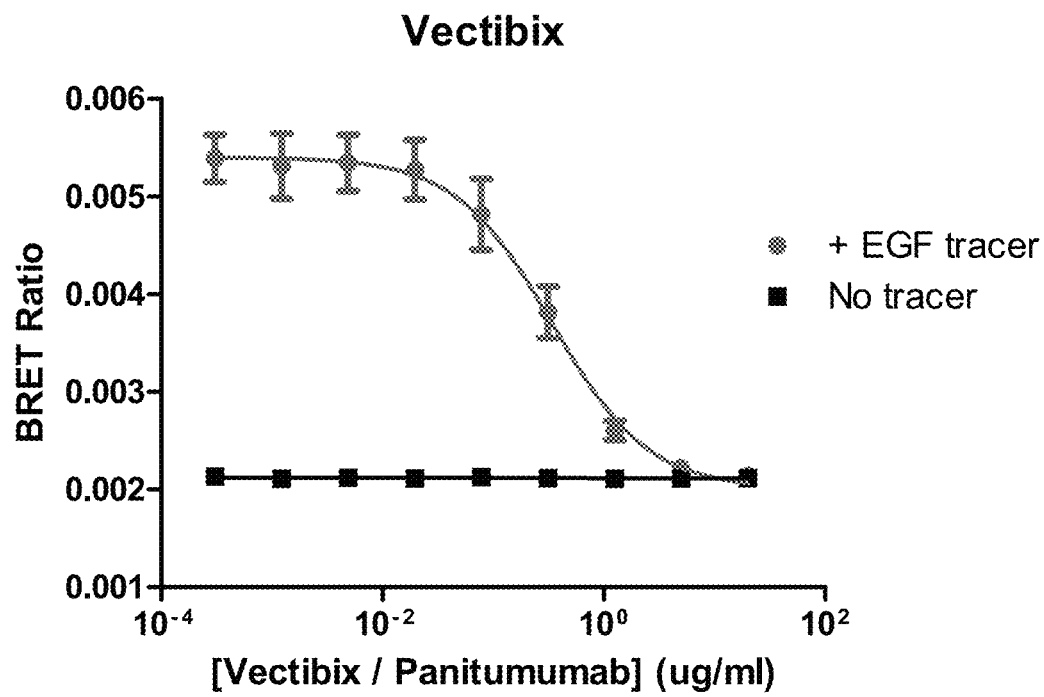
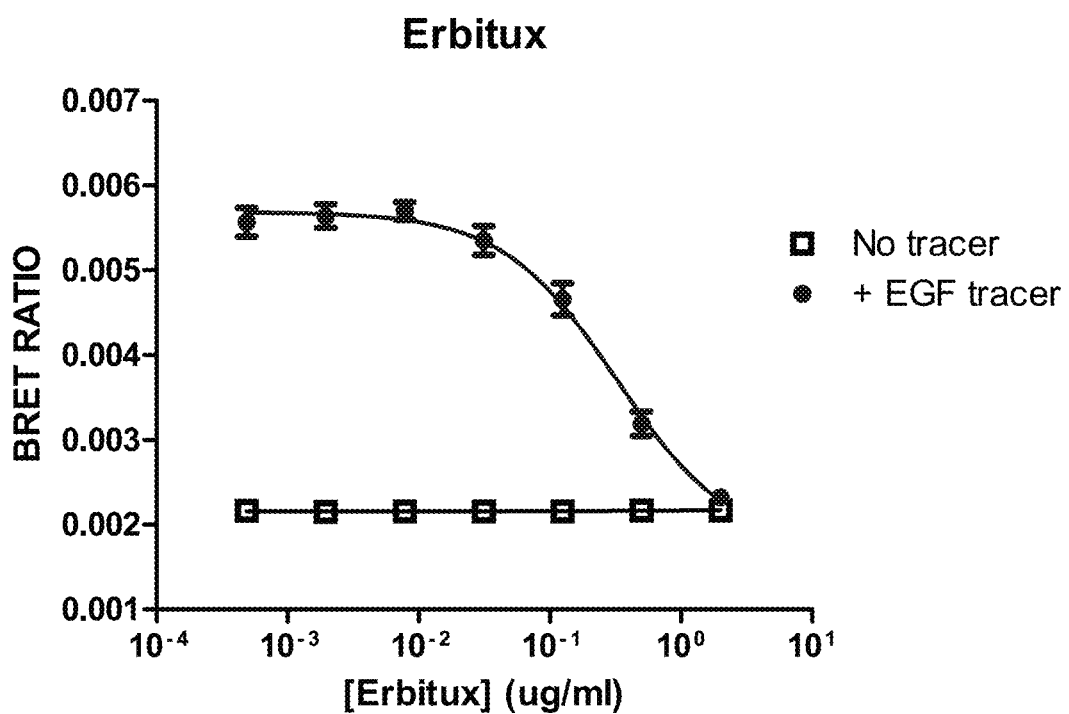

RECOGNITION OF CELLULAR TARGET BINDING BY A BIOACTIVE AGENT USING INTRACELLULAR BIOLUMINESCENCE RESONANCE ENERGY TRANSFER

CROSS-REFERENCE TO RELATED APPLICATIONS

The present application is a continuation of U.S. patent application Ser. No. 14/104,845, filed Dec. 12, 2013, now U.S. Pat. No. 10,067,149, which claims priority to U.S. Provisional Patent Application Ser. No. 61/736,429 filed Dec. 12, 2012; and U.S. Provisional Patent Application Ser. No. 61/794,461 filed Mar. 15, 2013; each of which are hereby incorporated by reference in their entireties.

FIELD

The present invention provides compositions and methods for detection and analysis of intracellular binding of a bioactive agent to a cellular target. In particular, provided herein are bioactive agents tethered to fluorophores, cellular targets fused to bioluminescent reporters, and methods of detecting and analyzing the interaction of bioactive agents with cellular targets therewith.

BACKGROUND

The interaction of molecular species with cellular targets is critically important in understanding cellular physiology and developing therapeutic interventions, such as new synthetic drugs and biopharmaceuticals. Methods are needed for accurately and efficiently determining target engagement, particularly within living cells where these interactions mediate their phenotypic responses. The ability to affectively interrogate target engagement has broad implications to the discovery process, ranging from high-throughput screening, optimization of screening hit into drug leads, and the discovery and characterization of therapeutically relevant cellular targets.

Phenotypic-based screening with a small molecule library plays an important role in the drug discovery field. Using such screening approaches, compound libraries, without prior knowledge of their underlying cellular targets, are screened for their ability to mitigate disease symptoms. While this approach can be used to identify small molecules that are able to modulate cellular physiology, determining the biological relevant targets of these small molecule hits is a major technical challenge. In addition, small molecules promoting some desirable phenotypic responses may pose in vivo liabilities due to off-target interactions. In order to predict drug selectivity and minimize potential side effects, it is important to also profile lower affinity, off-target interactions. Most methods today rely on the enrichment of these targets from complex cellular lysate using "bi-functionalized" lead compounds that contain a selective moiety (the lead compound) and a sorting moiety (affinity). As the enrichment is based on the binding properties of the lead compounds, where the inherent affinity of these leads for their target is insufficient, compound analogs are designed to photo-crosslink to the target. By either approach, the specificity of target isolation is essential, and the failure rate of these methods is high. Failure of these approaches can be due to: hit compounds binding multiple targets with low to moderate affinity with these relative weak interactions difficult to detect; lack of robust, straightforward, unbiased technologies to characterize the detected interactions; inability to perform target isolation within the native cellular environment upon which interactions may depend; limited information provided about the binding potency of targets in the cell; and high background of false positive interactions due to non-specific binding to the solid support or functionalized small molecule.

SUMMARY

In some embodiments, the present invention provides BRET assay systems comprising: (a) a bioactive agent tethered to a fluorophore; (b) a cellular target fused to a bioluminescent reporter; and (c) a substrate for the bioluminescent reporter. In some embodiments, the bioactive agent is a small molecule. In some embodiments, the fluorophore is a carboxy rhodamine analog. In some embodiments, the bioluminescent reporter comprises a polypeptide with at least 70% sequence identity (e.g., 75% identity, 80% identity, 85% identity, 90% identity, 95% identity, 98% identity, 99% identity) with SEQ ID NO: 1. In some embodiments, (a) and (b) are within a cell. In some embodiments, (b) is expressed intracellularly as a fusion protein with a protein of interest, e.g., cellular target. In some embodiments, (a) is added extracellularly and enters the cell. In some embodiments, the cellular target is a binding partner of the bioactive agent. In some embodiments, the emission spectrum of the bioluminescent reporter overlaps with the absorption spectrum of the fluorophore. In some embodiments, upon binding of the bioactive agent to the cellular target, conversion of the substrate to a reaction product by the bioluminescent reporter results in excitation of the fluorophore by BRET and fluorescence emission from the fluorophore. In some embodiments, (a) is one of a library of bioactive agents tethered to fluorophores. In some embodiments, (b) is one of a plurality of cellular targets fused to a bioluminescent reporter. In some embodiments, (b) is a library of cells expressing one of a plurality of cellular targets fused to a bioluminescent reporter.

In some embodiments, the present invention provides methods of detecting, analyzing, characterizing, etc. the binding of a bioactive agent to a cellular target. In some embodiments, the cellular target may be the primary drug target. In some embodiments, the cellular target is an off-target liability that may cause undesirable side effects in vivo. In some embodiments, the present invention provides cells comprising one or more of (e.g., each of) (a) a bioactive agents tethered to a fluorophore; (b) a cellular target fused to a bioluminescent reporter; and (c) a substrate for the bioluminescent reporter.

In some embodiments, the present invention provides methods for detection of an interaction between a bioactive agent and a cellular target comprising: (a) expressing in a cell a fusion of said cellular target and a bioluminescent reporter that emits energy at a first wavelength; (b) contacting said cell with said bioactive agent tethered to a fluorophore, wherein said fluorophore accepts energy at said first wavelength and emits energy at a second wavelength; (c) contacting said cell with a substrate for said bioluminescent reporter; (d) detecting energy at said second wavelength, wherein the presence of said energy at said second wavelength indicates the interaction of said bioactive agent with said cellular target.

DRAWINGS

FIG. 1 shows a schematic representation of an embodiment of the present invention: (Panel A) fluorophore-tethered bioactive agent and bioluminescent-reporter-tethered cellular target; (Panel B) binding of bioactive agent to cellular target; (Panel C) addition of reporter substrate results in BRET; and (Panel D) displacement by excess untethered bioactive agent results in loss of BRET and fluorescence.

FIGS. 2A-B show graphs comparing the BRET profiles of two different fluorophore-SAHA derivatives as BRET acceptors for NANOLUC-HDAC6 fusions in live cells.

FIGS. 3A-B show graphs depicting the effect of dilution of expression on assay performance. FIG. 3A demonstrates the effect of lowered expression on the BRET assay window using competitive displacement of fluorophore-tethered SAHA from NANOLUC-fused HDAC6. FIG. 3B shows the effect of lowered expression on both BRET assay window, as well as observed compound potency (EC50) for a drug tracer binding to NANOLUC-Histamine H1 receptor.

FIG. 4, Panels A and B show graphs demonstrating the requirement of the cellular milieu for pro-drug processing.

FIGS. 5A-C show graphs demonstrating the ability to use permeabilization agents to potentiate the entry of impermeable drug tracers.

FIG. 6 shows a graph depicting competitive displacement of fluorophore-tethered BIRB-796 from NANOLUC-fused p38.

FIG. 7, Panels A and B show graphs depicting measurement of the kinetics of fluorophore-tethered BIRB-796 from NANOLUC-fused p38.

FIGS. 8A-B show exemplary fluorophore-tethered bioactive agents and other compounds that find use in embodiments described herein.

FIGS. 9A-B show a comparison of p38 fusions with *Renilla* luciferase and NANOLUC luciferase within an embodiment described herein.

FIGS. 10A-B show dose-response curves for NANOLUC-p38alpha binding to a BIRB-TOM conjugate compared to a BIRB-TMR conjugate.

Figure 14B:
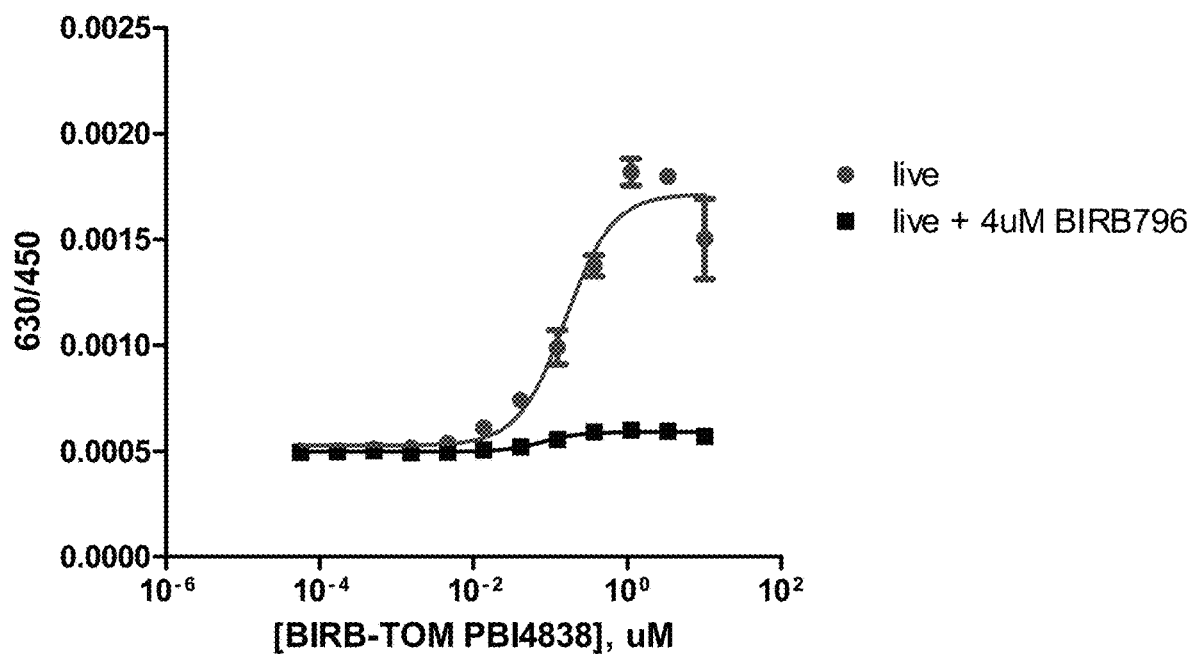
Figure 14C:
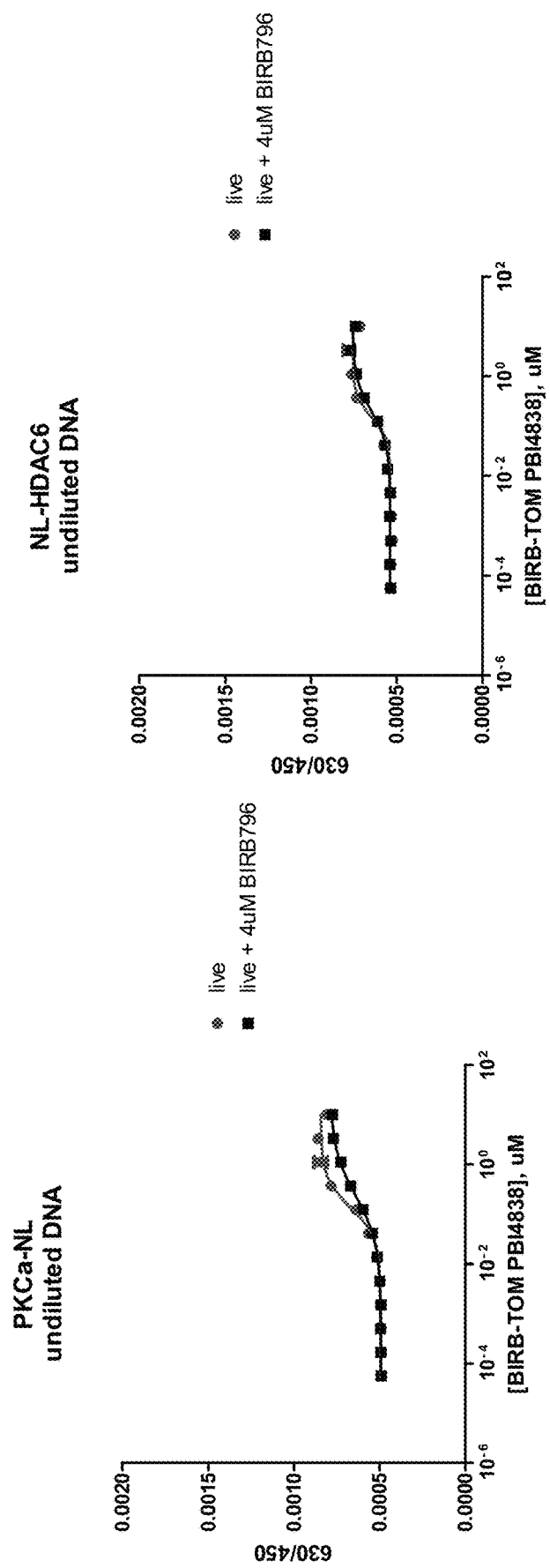

FIGS. 14A-C show affinity of PBI-4838 to Jnk2, p38beta, and p38alpha.

Figure 15B:
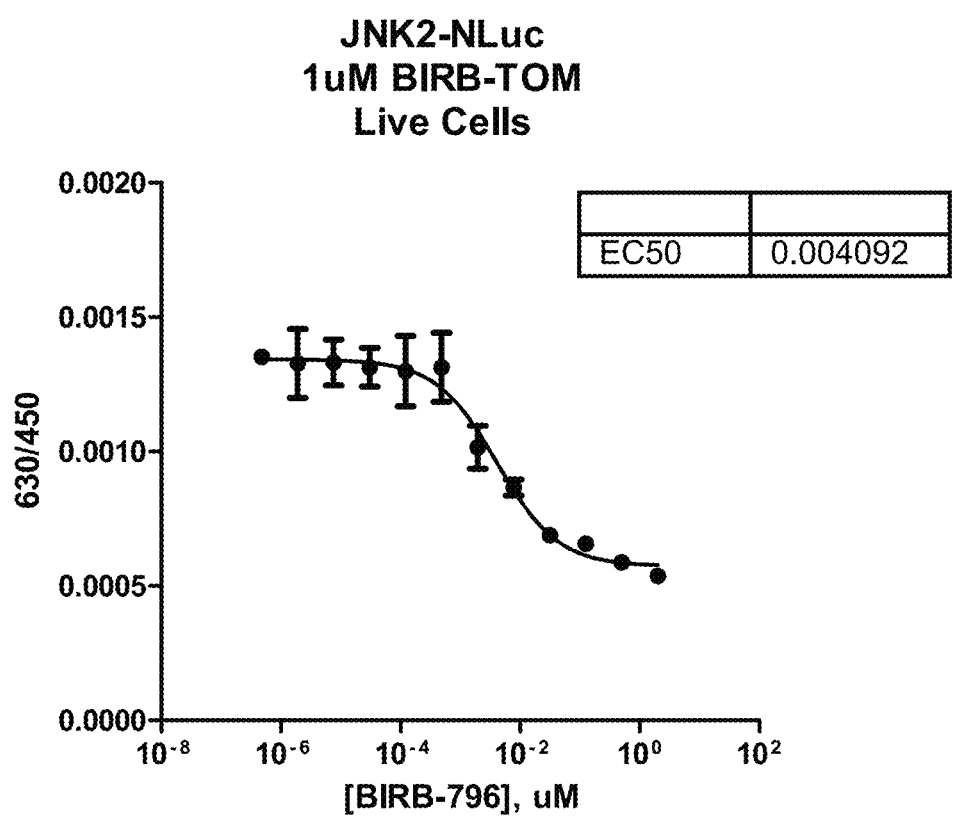
Figure 15C:
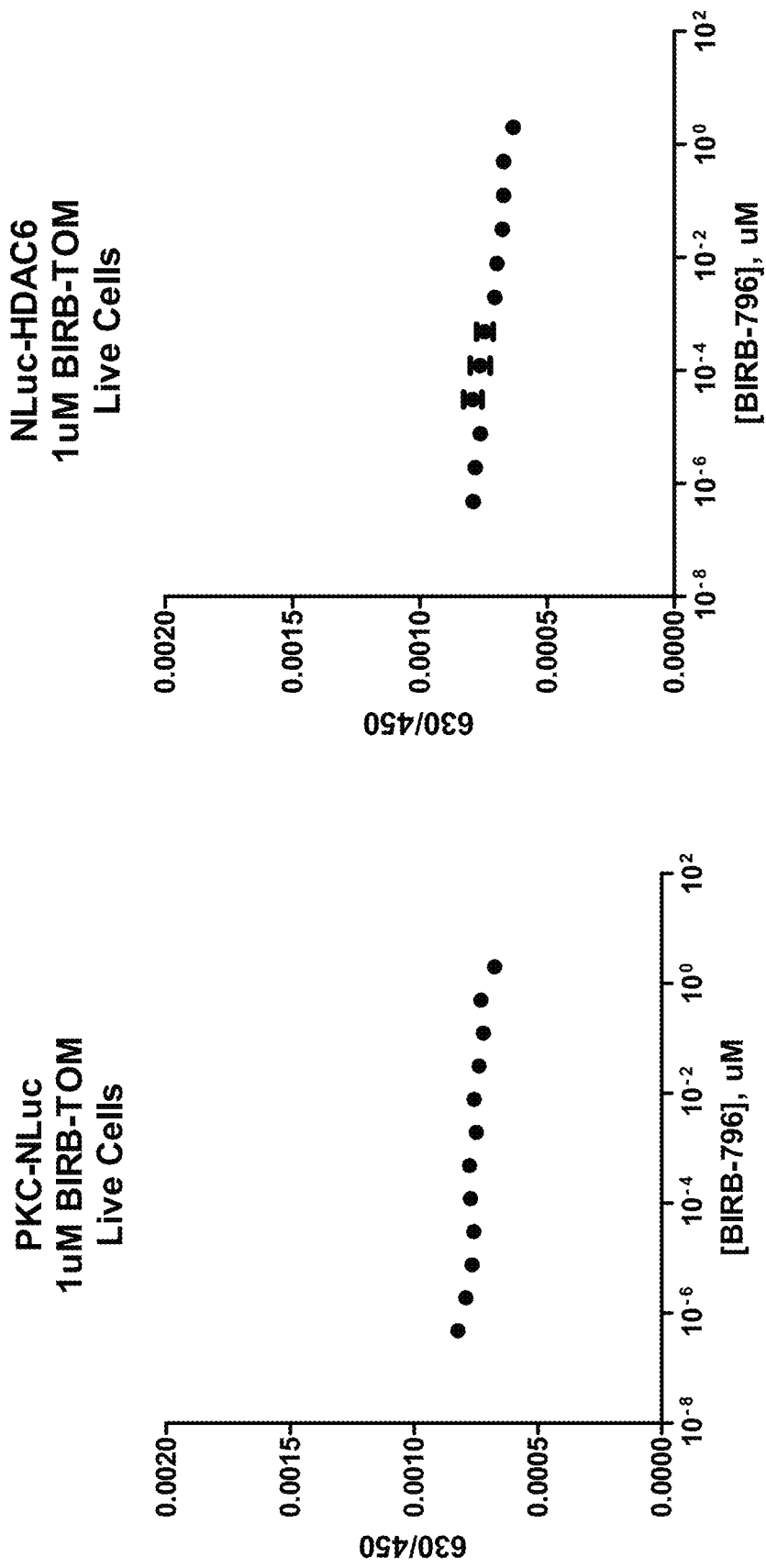
Figure 16A:
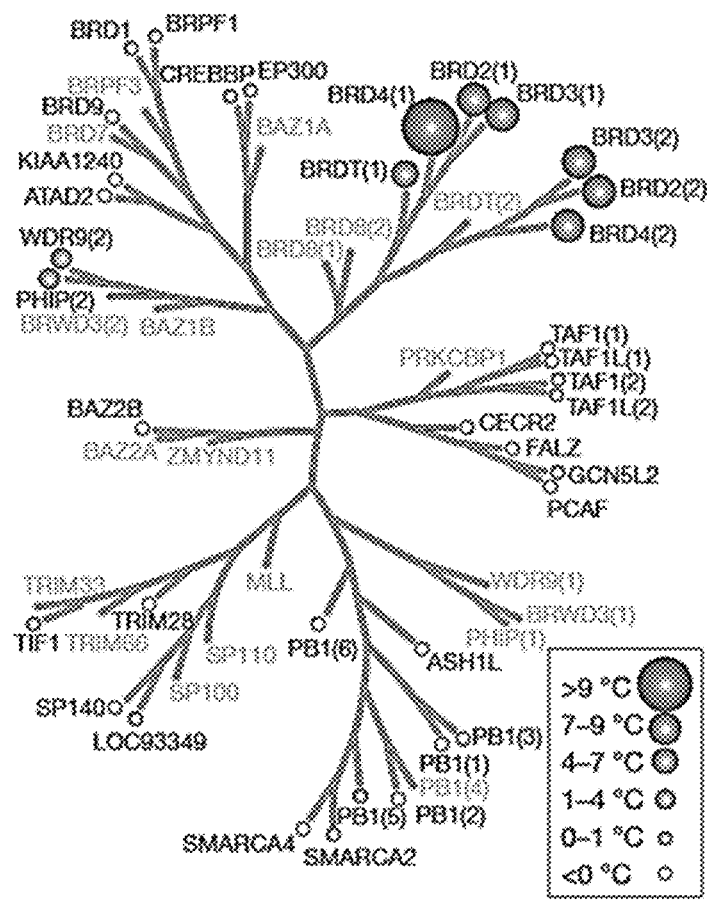
Figure 16B:
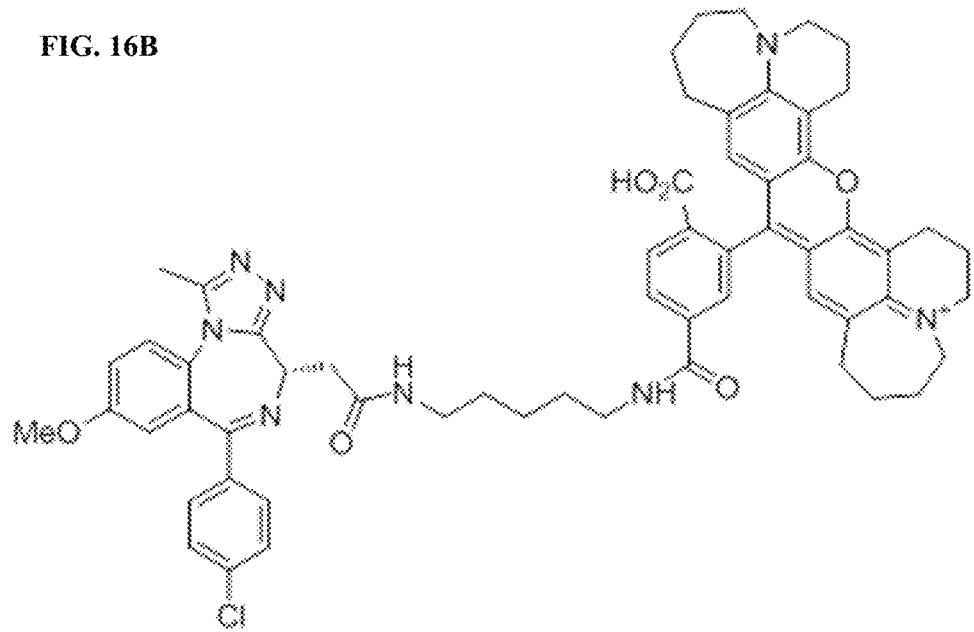
Figure 16C:
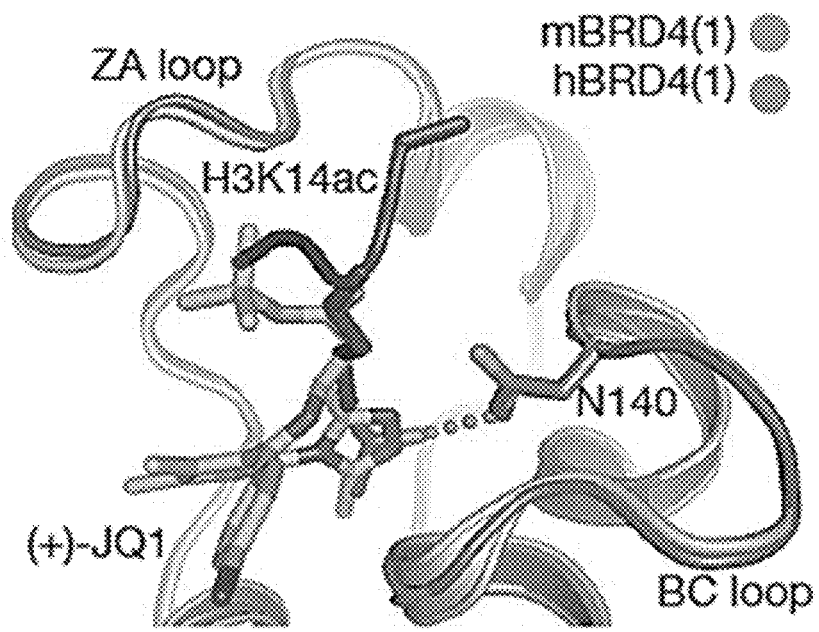
Figure 16D:
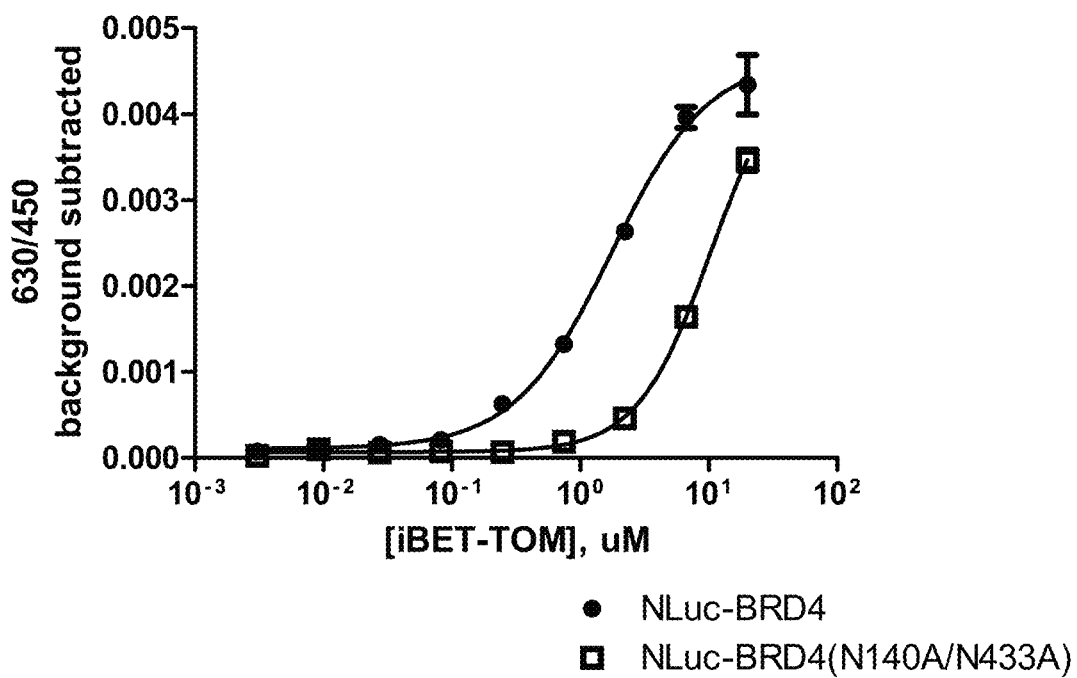

FIGS. 15A-C shows relative affinities of PBI-4966 to wild-type BRD4 versus the mutant BRD4.

FIGS. 16A-D show structurally-distinct compounds can be identified by competitive displacement of drug tracers using the method of the present invention.

FIGS. 17A-C show graphs depicting competitive displacement of drug tracers with unlabeled drug.

FIG. 18 shows a graph depicting measurement of specific binding between a drug tracer and the NANOLUC-target fusion in a cell-free system.

FIG. 19, Panels A and B show graphs depicting a specific BRET response in TNT.

FIGS. 20A-B show graphs depicting measurement of binding of fluorescently-labeled cytokines to NANOLUC-EGFR.

DETAILED DESCRIPTION

Figure 1:
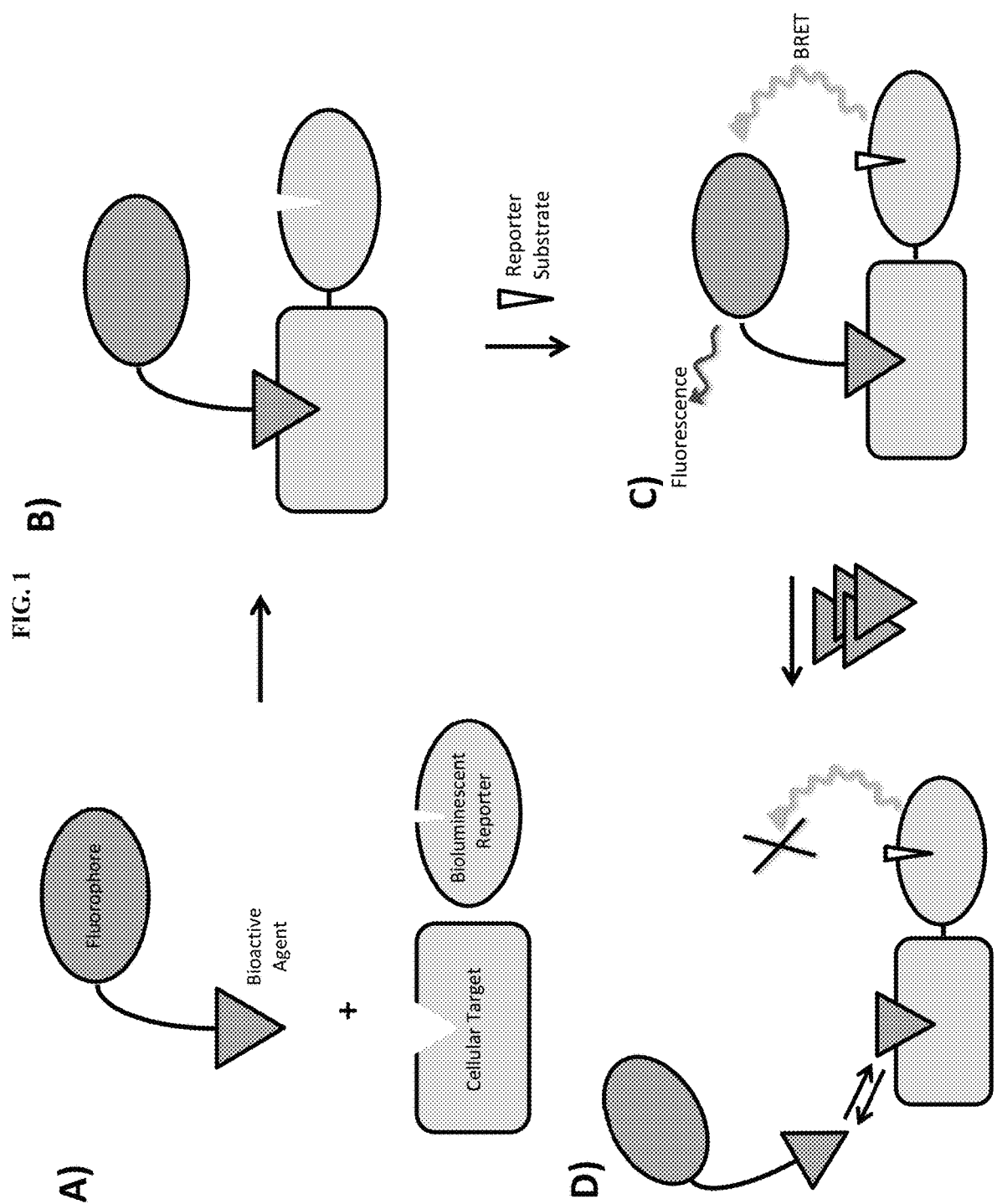

The present invention provides compositions and methods for detection and analysis of intracellular binding of a bioactive agent to a cellular target. In particular, provided herein are bioactive agents tethered to fluorophores, potential cellular targets fused to bioluminescent reporter proteins and methods of detecting and analyzing the interaction of bioactive agents with cellular targets therewith (See FIG. 1).

The interaction of a first entity (e.g., bioactive agent) and a second entity (e.g., cellular target) is detected, characterized, quantified, analyzed, etc. through the detection/measurement of a signal produced by signal transfer (e.g., transfer of energy (e.g., fluorescence, light energy, resonance, by BRET, etc.)) between a third entity (e.g., fluorophore) connected, fused, tethered, linked, etc. to the first entity and a fourth entity (e.g., bioluminescent reporter protein) connected, fused, tethered, linked, etc. to the second entity. The interaction and/or binding of the first and second entities bring the third and fourth entities into close enough proximity to allow signal transfer (e.g., energy transfer) from one to another. In some embodiments, the fourth entity (e.g., bioluminescent reporter protein) emits energy (e.g., upon interaction with its substrate), and that emitted energy is absorbed by the third entity (e.g., fluorophore), causing the third entity to emit measurable different energy form the fourth entity (e.g., light at a different wavelength). In such embodiments, detection of the energy emitted from the third entity (e.g., light at the emission maximum of the third entity) upon addition to the system of the substrate for the fourth entity (e.g., bioluminescent reporter) indicates interaction of the first and second entities. In some embodiments, the duration, kinetics, affinity, strength, and/or specificity, of the binding of the first and second entities is detected, measured, quantified, determined, interrogated, etc. based on measurement of the signal output of the fourth entity (e.g., bioluminescent reporter protein) under various conditions.

In various embodiments, a cellular target fused to a bioluminescent reporter protein and a bioactive agent tethered to a fluorophore are provided (e.g., intracellularly, extracellularly, in lysate, in vitro, etc.). Substrate for the bioluminescent reporter protein is added to the system. If an interaction has occurred (e.g., binding) between the bioactive agent and the cellular target, the bioluminescent reporter protein and fluorophore are brought into close enough proximity for BRET to occur, and a detectable signal to be emitted from the fluorophore.

In some embodiments, the cellular target and bioluminescent reporter fusion is expressed in cells in which an assay is to be performed. In some embodiments, the fusion is expressed at or near the native abundance for the cellular target. In some embodiments, the fluorophore-tethered bioactive agent is added extracellularly (e.g., added to the culture medium) and enters the cell via diffusion, active transport, passive transport, endocytosis, or any suitable mechanism. In some embodiments, varying amount of fluorophore-tethered bioactive agent is added to the cells to assay binding kinetics, assay binding affinity, provide sufficient signal, etc.

In certain embodiments, the present invention provides compositions, methods, and systems for detection of intracellular interactions between a bioactive agent and cellular target (e.g., known or unknown). In some embodiments, a fusion of a bioluminescent reporter and a cellular target are expressed within a cell. The bioactive agent, tethered to a fluorophore, is introduced to the cell (e.g., conjugate of fluorophore and bioactive agent is cell permeable, cell is permeablized, etc.). A substrate for the bioluminescent reporter protein is added to the cell prior, concurrently or subsequent to the addition of the bioactive agent. Detection of a fluorescent signal from the fluorophore (as the result of BRET) indicates an intracellular interaction (e.g., binding) between the bioactive agent and cellular target. In some embodiments, a cellular target fused to a bioluminescent reporter is expressed at a natural cellular abundance (e.g., relative to the native cellular target, or at a level appropriate for proper biological function of the fused target). In some embodiments, interaction of a bioactive agent with a cellular target is detected intracellularly.

In some embodiments, characteristics of the interaction between the bioactive agent and cellular target are interrogated by altering the cellular conditions or the conditions of the system. For example, in some embodiments, a competitive binder of the cellular target (e.g., untethered bioactive agent) is added to the cell to compete with the fluorophore-tethered bioactive agent.

In some embodiments, a library of bioluminescent reporter protein-tagged cellular targets is provided (e.g., in solution, in a lysate, immobilized on a surface, expressed within a cell, etc.). In some embodiments, a bioactive agent is provided which lacks a known cellular target or where knowledge of the cellular target is uncertain or incomplete. The cellular target of a bioactive agent is determined by adding the bioactive agent to the library and determining which cellular-target fusion produces BRET induced fluorescence of the bioactive agent-tethered fluorophore. In some embodiments, the library of bioluminescent reporter-tagged cellular targets is provided as a collection of nucleic acids or vectors comprising nucleic acids (e.g., plasmids, BacMam viruses, Lentiviruses, etc.) encoding the protein fusions. In some embodiments, the library of bioluminescent reporter protein-tagged cellular targets is expressed within cells. In some embodiments, the library of bioluminescent reporter-tagged cellular targets is provided by translating nucleic acids in cell-free translation reactions. In some embodiments, a library of cellular targets fusions, or cells expressing cellular target fusions, are provided in a microplate format. In such embodiments, the interaction of a bioactive agent (e.g., one identified through a phenotypic assay or screen) with the entire library of cellular targets can be interrogated (e.g., in solution, in lysates, intracellularly, etc.) in a high-throughput manner. In some embodiments, bioluminescent reporter-tagged cellular targets are immobilized on a solid surface to create a protein array. For example, in some embodiments, in addition to the bioluminescent reporter, cellular targets are also expressed as fusions with a tag or coupled to a protein (e.g., HALOTAG, Promega) that allows for the proteins to be covalently immobilized on a solid surface (e.g., a surface displaying appropriate ligands (e.g., HALOTAG Ligand)). In certain embodiments, a library of bioactive agents (e.g., lead compounds or drug-like small molecules) is added to the system (e.g., array) and any pairs capable of producing BRET are identified. In some embodiments, cellular targets for all or a portion of a library of bioactive agents are unknown.

In certain embodiments, compositions, methods, and systems herein provide a conjugate of a bioactive agent and an energy acceptor (e.g., fluorophore, chromophore). In some embodiments, a bioactive agent is any small molecule (e.g., >2000 daltons, >1000 daltons, >500 daltons, etc.), macromolecule, or molecular complex capable of interacting with the biology of a cell. In some embodiments, an energy acceptor is an entity capable of generating, exhibiting, and/or emitting a signal (e.g., light, heat, chemical reaction, fluorescence, resonance energy, etc.) when triggered by energy absorption (e.g., resonance energy transfer). In some embodiments, a bioactive agent and energy acceptor (e.g., fluorophore, chromophore) are fused, tethered, connected, etc., by any suitable structure or mechanism (e.g., expressed as a fusion construct (e.g., with or without peptide linker), chemically linked (e.g., directly or indirectly), enzymatically linked, linked by a linker (e.g., peptide, nucleic acid, polymer, ester linkage, PEG linker, carbon chain, etc.)). In some embodiments, the conjugate of a bioactive agent and an energy acceptor (e.g., bioactive agent tethered to a fluorophore) is produced by non-natural chemical synthesis (e.g., a purposeful execution of chemical reactions not present in natural cells). The type of linkage should not be viewed as limiting.

As used herein, the term "bioactive agent" refers generally to any physiologically or pharmacologically active substance or a substance suitable for detection. In some embodiments, a bioactive agent is a potential therapeutic compound (e.g., small molecule, peptide, nucleic acid, etc.), or drug-like molecule. In some embodiments, the bioactive agent is produced by non-natural chemical synthesis (e.g., a purposeful execution of chemical reactions not present in natural cells). Bioactive agents for use in embodiments described herein are not limited by size or structure.

In certain embodiments, libraries of bioactive agents (e.g., >50 agents, >100 agents, >500 agents, >1000 agents, >5000 agents, >10,000 agents, >50,000 agents, etc.) are provided. In some embodiments, systems, methods, and compositions are provided for screening libraries of bioactive agents for a phenotypic effect and/or activity. In some embodiments, the present invention provides means of identifying the bioactive agent in a library responsible for producing, eliciting, inducing, etc. phenotypic effect and/or activity. In some embodiments, the present invention provides means of identifying the cellular target of a bioactive agent (e.g., a bioactive agent responsible for the phenotypic effect and/or activity).

As used herein, the term "energy acceptor" refers to any small molecule (e.g., dye), macromolecule (e.g., autofluorescent protein, phycobiliproteins, nanoparticle, surface, etc.), or molecular complex that produces a readily detectable signal in response to energy absorption (e.g., resonance energy transfer). In certain embodiments, an energy acceptor is a fluorophore or other detectable chromophore. Suitable fluorophores include, but are not limited to: xanthene derivatives (e.g., fluorescein, rhodamine, Oregon green, eosin, Texas red, etc.), cyanine derivatives (e.g., cyanine, indocarbocyanine, oxacarbocyanine, thiacarbocyanine, merocyanine, etc.), naphthalene derivatives (e.g., dansyl and prodan derivatives), oxadiazole derivatives (e.g., pyridyloxazole, nitrobenzoxadiazole, benzoxadiazole, etc.), pyrene derivatives (e.g., cascade blue), oxazine derivatives (e.g., Nile red, Nile blue, cresyl violet, oxazine 170, etc.), acridine derivatives (e.g., proflavin, acridine orange, acridine yellow, etc.), arylmethine derivatives (e.g., auramine, crystal violet, malachite green, etc.), tetrapyrrole derivatives (e.g., porphin, phtalocyanine, bilirubin, etc.), CF dye (Biotium), BODIPY (Invitrogen), ALEXA FLOUR (Invitrogen), DYLIGHT FLUOR (Thermo Scientific, Pierce), ATTO and TRACY (Sigma Aldrich), FluoProbes (Interchim), DY and MEGASTOKES (Dyomics), SULFO CY dyes (CYANDYE, LLC), SETAU and SQUARE DYES (SETA BioMedicals), QUASAR and CAL FLUOR dyes (Biosearch Technologies), SURELIGHT DYES (APC, RPE, PerCP, Phycobilisomes) (Columbia Biosciences), APC, APCXL, RPE, BPE (Phyco-Biotech), autofluorescent proteins (e.g., YFP, RFP, mCherry, mKate), quantum dot nanocrystals, etc. In some embodiments, a fluorophore is a rhodamine analog (e.g., carboxy rhodamine analog), such as those described in U.S. patent application Ser. No. 13/682,589, herein incorporated by reference in its entirety. Some such fluorophores are described herein in Example 8. In some embodiments, BRET efficiency is significantly enhanced by the technical features of rhodamine analog (e.g., carboxy rhodamine analog) as an energy acceptor compared to other fluorophores. For example, the left shifted EC50 and reduced nonspecific background of these dyes is advantageous for use in some embodiments.

In certain embodiments, compositions, methods, and systems herein provide a fusion of a cellular target and a bioluminescent reporter protein (e.g., luciferase). In some embodiments, a cellular target and bioluminescent reporter protein are fused, tethered, connected, etc. by any suitable structure or mechanism (e.g., expressed as a fusion construct (e.g., with or without peptide linker), chemically linked (e.g., directly or indirectly), enzymatically linked, linked by a linker (e.g., peptide, nucleic acid, other polymer (e.g., ester linkage, PEG linker, carbon chain, etc.)). In some embodiments, an amino acid chain (e.g., 3-100 amino acids) is used to connect the cellular target and a bioluminescent reporter protein. In some embodiments, the structure and/or function of neither the cellular target nor the bioluminescent reporter are impacted (e.g., significantly impacted) by fusion or the presence of the linker. In certain embodiments, a linker allows fusion without loss of activity or one or both of the elements. In other embodiments, an amino acid linker properly spaces and/or orients the bioluminescent reported for energy transfer with the fluorophore.

In some embodiments, a cellular target comprises any suitable binding/interaction partner (e.g., receptor, enzyme) for a bioactive agent (e.g., small molecule, protein, nucleic acid, lipid, etc.). However, in some embodiments, knowledge of the interaction between a cellular target and bioactive agent is not required to practice the invention. In particular embodiments, a cellular target is a protein that binds to or otherwise interacts with (e.g., has a binding affinity to) a bioactive agent. In more particular embodiments, a cellular target is a receptor protein or an enzyme that binds to or otherwise interacts with (e.g., has a binding affinity to) a small molecule bioactive agent. The present invention is not limited by the identity, type, or class of cellular targets. In certain embodiments, libraries of hundreds, thousands, tens of thousands, more different cellular targets find use in the present invention. In some embodiments, a cellular target is a G-protein coupled receptor or a protein kinase.

In certain embodiments, the bioluminescent reporter is a luciferase. In some embodiments, a luciferase is selected from those found in *Gaussia, Coleoptera*, (e.g., fireflies), *Renilla, Vargula, Oplophorus*, mutants thereof, portions thereof, variants thereof, and any other luciferase enzymes suitable for the systems and methods described herein. In some embodiments, the bioluminescent reporter protein is a modified, enhanced luciferase enzyme from *Oplophorus* (e.g., NANOLUC enzyme from Promega Corporation, SEQ ID NO: 1, or a sequence with at least 70% identity (e.g., >70%, >80%, >90%, >95%) thereto). In some embodiments, the bioluminescent reporter protein is a thermostable *Photuris pennsylvanica* luciferase or a sequence with at least 70% identity (e.g., >70%, >80%, >90%, >95%) thereto). Exemplary bioluminescent reporters are described, for example, in U.S. Pat. App. No. 2010/0281552 and U.S. Pat. App. No. 2012/0174242, both of which are herein incorporated by reference in their entireties.

In some embodiments, the bioluminescent reporter protein comprises NANOLUC (See U.S. Pat. App. Nos. 2010/0281552 and 2012/0174242, herein incorporated by reference in their entireties). In some embodiments, the bioluminescent reporter protein comprises a polypeptide with at least 70% identity (e.g., >70%, >80%, >90%, >95%) to SEQ ID NO: 1 that retains bioluminescent characteristics. In certain embodiments, the use of the NANOLUC enzyme, or a variant thereof, provides features (e.g., signal intensity, brightness, high light output, etc.) that enable the use of the BRET assays described herein. In some embodiments, the high light output of NANOLUC enables the low concentration (e.g., <1 µM, <100 nM, <10 nm, <1 nm, etc.) of assay components, e.g., DNA encoding NANOLUC, useful to carry out assays under physiologically relevant conditions. In some embodiments, NANOLUC enables the use of BRET in characterizing cellular targets identified in a phenotypic screen.

In some embodiments, a substrate for the bioluminescent reporter protein is provided. In some embodiments, the bioluminescent reporter protein converts the substrate into a reaction product and releases light energy as a by-product. In some embodiments, the substrate is a substrate for a luciferase enzyme. In some embodiments, the substrate is a substrate for a modified, enhanced luciferase enzyme from *Oplophorus*, e.g., NANOLUC enzyme from Promega Corporation (e.g., SEQ ID NO: 1). In some embodiments, a pro-substrate for the bioluminescent reporter protein is provided, which produces a substrate through a chemical or physical process (e.g., hydrolysis, enzymatic reaction, photo-cleavage, etc). In some embodiments, the pro-substrate comprises coelenterazine, a coelenterazine derivative, a structural or functional equivalent of coelenterazine, a molecule substantially equivalent to coelenterazine (e.g., structurally and/or functionally), or molecule functionally or structurally similar to coelenterazine. In some embodiments, the bioluminescent reporter protein converts the coelenterazine, coelenterazine derivative, structural or functional equivalent of coelenterazine, or substantial equivalent to coelenterazine into coelenteramide, a coelenteramide derivative, a structural or functional equivalent of coelenteramide, or a substantial equivalent to coelenteramide and releases light energy as a by-product.

In some embodiments, fluorophore and bioluminescent reporter are selected that exhibit sufficient overlap of emission (e.g., of bioluminescent reporter) and excitation (e.g., of fluorphore) spectra to provide efficient energy transfer between the two. In some embodiments, the peak emission of the bioluminescent reporter is substantially separated from the peak emission of the fluorophore, for example by at least 80 nm, 100 nm, 120 nm, 140 nm, etc., in wavelength. In particular embodiments, the Forster distance of the fluorophore and bioluminescent reporter pair is small (e.g., <20 nm, <10 nm, <5 nm, <3 nm, etc.). In such embodiments, the short Forster distance results in the requirement that the fluorophore and bioluminescent reporter must be brought into very close proximity for energy transfer to occur. Therefore, the short Forster distance reduces aberrant and/or background signal (e.g., created by diffusing fluorophore and/or reporter).

In certain embodiments, a fluorophore and bioluminescent reporter pair are selected that are sufficiently bright to allow detection of the transferred signal at a native abundance (or near native abundance) of the cellular target fused to the bioluminescent reporter. In some embodiments, should either the selected fluorophore or bioluminescent reporter produce insufficient energy (light) emission, either the fusion of the cellular target and bioluminescent reporter will need to be overexpressed (e.g., beyond native abundance, beyond a biologically relevant level, etc.), and/or the amount of fluorophore-tethered bioactive agent will have to be increased (e.g., to a potentially toxic level, beyond a physiologically relevant level, above the amount when kinetic experiments can be performed, etc.). In some embodiments, sufficient brightness of the bioluminescent reporter and fluorophore allows detection of bioactive agent and cellular target interaction at a range of concentrations and ratios.

In some embodiments, compositions, methods, and systems are provided for identification of the cellular targets of lead compounds emerging from a phenotypic assay or phenotypic screen. In some embodiments, binding of a bioactive agent (e.g., small molecule) to a cellular target is characterized using a competitive binding assay (SEE FIG. 1, Panel C and 1, Panel D). In some embodiments, following identification of bioactive agents capable of eliciting a phenotype, "lead compounds" tethered to fluorophores are used to identify cellular targets, through their linkage to a bioluminescence reporter protein (e.g., binding of bioactive agent to cellular target results in BRET between bioluminescence reporter protein and fluorophore). In such embodiments, although a phenotype has been associated with a particular bioactive agent, the interaction partner (e.g., cellular target) for that bioactive agent in unknown. In some embodiments, the bioactive agent tethered to a fluorophore is able to regenerate a phenotype, thereby validating that tethering the bioactive agent to the fluorophore (or the cellular target to the bioluminescent reporter) does not affect the cellular binding patterns. In some embodiments, the use of a library of cellular targets, each fused to bioluminescent reporter protein (e.g., NANOLUC), provides less interference due to relative solubility or native abundance of the cellular target compared to other detection methods (e.g., mass spectrometry analysis). In some embodiments, such a detection method provides a greater degree of sensitivity or specificity. In some embodiments, target identification through linkage to a bioluminescence reporter protein enables detection through energy transfer, even when binding of the target is inefficient or incomplete. In some embodiments, BRET allows for analysis of the lead compound's binding affinity in live cells using competitive displacement of a fluorescent tracer that binds to the same site on the cellular target. In some embodiments, systems and methods described herein provide the ability to use two distinct methods with the same library for target identification, thus providing higher stringency for identifying cellular targets, complementary methods addressing all the major limitations with other approaches, detection of low affinity targets (e.g., BRET provides the advantage of maintaining the bioactive agent in equilibrium with the target throughout the experiment).

Some embodiments described herein find use in drug discovery, drug validation, drug target discovery, or drug target validation. In certain embodiments, the binding interaction between a bioactive agent (e.g., drug-like small molecule) and a cellular target can be detected, validated, and/or characterized. In some embodiments, the relative binding affinity of bioactive agents for a cellular target (e.g., in solution, in a lysate, on a surface, in a cell, etc.), can be determined by their ability to displace a bioactive agent that has been tethered to a fluorophore. Specifically, higher binding affinity of a first bioactive agent relative to a second bioactive agent is indicated by requiring a lower concentration of the first bioactive agent to displace a tethered bioactive agent relative to the second bioactive agent. Displacement of the tethered bioactive agent is determined by the loss or reduction of energy transfer from the bioluminescent reporter protein fused to a cellular target. In some embodiments, the concentration of bioactive agent needed to displace a tethered bioactive agent is used to estimate the binding EC50 or the inhibition constant (Ki) for bioactive agent. In some embodiments, the development of new or modified bioactive agents is guided by their ability to displace one or more bioactive agents, each tethered to a fluorophore, from one or more cellular targets, each fused to a bioluminescent reporter protein.

In some embodiments, a collection of compounds which may have unknown binding affinity to a cellular target may be screened for their ability to bind the target fused to a bioluminescent protein by determining their ability to displace a bioactive agent tethered to a fluorophore. In some embodiments, compounds may be screened for their ability to bind a first cellular target preferentially relative to a second cellular target by their ability to displace a first tethered bioactive agent from the first cellular target relative to a second tethered bioactive agent from the second bioactive target. In some embodiments, the first and second tethered bioactive agents are the same.

In some embodiments, systems and methods described herein provide the ability to determine the affinity of a bioactive agent (e.g., lead compound) for wild-type and mutant version(s) of a cellular target, e.g., target protein. In some embodiments, characterization of the affinity and selectivity of the fluorescently-labeled bioactive agent (e.g., drug) to a disease-relevant mutant protein may be performed in cells. Such systems and methods may be useful to identify bioactive agent(s) (e.g., drug) that selectively bind a wild-type or mutant protein differentially.

In addition to primary targets, intended targets, and/or known targets, bioactive agents (e.g., lead compounds) may also bind to unexpected and/or unintended cellular targets (off targets). In some cases, off target of a bioactive agent is responsible for a portion of the therapeutic and/or adverse effects associated with administration of the bioactive agent. In some embodiments, systems and methods described herein provide the ability to identify off targets of a bioactive agent. Understanding the identity and extent of off-target bioactive agent binding provides valuable information regarding the pharmacology of the agent.

In some embodiments, systems and methods described herein provide the ability to estimate the binding characteristics of a bioactive agent tethered with a fluorophore to a cellular target fused to a bioluminescent reporter (e.g., EC50, Kd, binding rate, environmental influences, etc.) In some embodiments, the binding characteristics are correlated to biochemical, physical, or phenotypic characteristics related to the cellular target. In some embodiments, displacement of the tethered bioactive agent by a separate agent may occur through separate sites on the cellular target. In some embodiments, the binding characteristics of the tethered bioactive agent may be used to determine the influence of post-translational modification (e.g., cleavage, phosphorylation, methylation, acetylation, lipidation, etc.), intracellular translocation (e.g., movement to a nucleus, mitochondria, membrane, etc.), or protein interaction (e.g., interactions with other proteins, nucleic acids, lipids, etc.) on the cellular target. An example is determining the binding characteristics of an antibody to a cellular target by its influence on the binding characteristics of the tethered bioactive agent. In some embodiments, the binding characteristics of the tethered bioactive agent may be used to determine the influence of chemical modifications or transformation of the bioactive agent or the tethered fluorophore (e.g., intracellular metabolism, change in ionic state, etc.)

In some embodiments, the cellular target may comprise more than one molecular component. For example, the target may comprise more than one polypeptide, and may further comprise other natural or synthetic molecules (e.g., prosthetic groups, cofactors, metabolites, nucleic acids, lipids, carbohydrates, etc.). In some embodiments, a bioactive agent tethered to a fluorophore binds to a first molecular component, and a bioluminescent reporter is fused to a second molecular component, so that a signal from the tethered bioactive agent is produced when bound to the first molecular component and the first molecular component is in close proximity to the second molecular component.

A priori knowledge of the existence of an interaction between a bioactive agent and cellular target is not need to practice the invention. In some embodiments, detection and/or characterization of an unknown or previously unidentified interaction by energy transfer is provided. Advantages of the systems, compositions, and methods described herein, over other methods of target discovery may include: a broad range of possible bioactive agent concentrations because (in some embodiments) it need not be expressed within cells (e.g., allows for addition of enough acceptor fluorophore to generate detectable signal), natural protein concentration of cellular target (e.g., no need for overexpression to gain enough signal for detection), signal detectable on a plate reader (e.g., high throughput detection, no imaging necessary), detection of interactions within a cell, etc.

In some embodiments, bioactive agents (e.g., lead compounds) are conjugated to a fluorescent energy acceptor dye, and therefore the binding of the modified agent to its luciferase-fused (e.g., NANOLUC-fused) cellular target results in energy transfer from NANOLUC to the acceptor dye. Such a system provides a homogeneous assay that can be performed in living cells. In some embodiments, the labeled bioactive agent remains in equilibrium with the cellular target throughout the experiment allowing detection of targets that interact with the lead compounds with low affinity. In some embodiments, BRET enables measurements of binding affinity in living cells by the competitive displacement of a fluorescent tracer designed for the same binding site.

In some embodiments, BRET efficiency is significantly enhanced by the technical features of NANOLUC as an energy donor compared to other luciferases. For example, NANOLUC is significantly brighter than other luciferases commonly used for BRET, thereby allowing energy transfer to be quantitated at lower expression levels which are more suitable for maintaining relevant biology within a cell. In some embodiments, the narrow emission spectrum of NANOLUC increases the dynamic range by reducing spectral cross-over in the acceptor channel. In some embodiments, the dynamic range can be further increased by using long-wavelength acceptors that emit in the near-red region of the spectrum (600 to 650 nm). In some embodiments, evaluation of multiple dye ligands during development of embodiments of the present invention revealed that rhodamine analogs (e.g., carboxy rhodamine analog), such as those described in U.S. patent application Ser. No. 13/682,589, herein incorporated by reference in its entirety, delivers an optimal dynamic range for use with NANOLUC and/or in the BRET applications described herein.

EXPERIMENTAL

Example 1

Experiments were conducted during development of embodiments of the present invention to demonstrate the improved performance of PBI tracer conjugates and compared to conjugates with standard dyes for drug tracer applications. In this example, conjugates of suberoylanilide hydroxamic acid (SAHA), an inhibitor of histone deacetylase 6 (HDAC6), and a PBI dye (SAHA-TOM (PBI-4968); See FIGS. 8A-B) or standard dye (SAHA-TAMRA (PBI-4967); See FIGS. 8A-B) were utilized in an intracellular BRET assay using a NANOLUC-HDAC fusion protein (SEQ ID NO: 3).

HEK293 cells were transfected using FuGene HD (Promega Corp.) with plasmid DNA encoding a NANOLUC-HDAC6 fusion protein. NANOLUC-HDAC6 DNA was diluted 1:1000 with a promoterless carrier DNA (pGEM3Z) to yield a final concentration of 50 ng/well total DNA in 96-well plate format (at a seeding density of 20,000 cells/well). Twenty-four hours post-transfection, cells were then incubated with serially-diluted tracer in the presence or absence of a molar excess of unlabeled SAHA (as a specificity control). Following equilibration with the drug tracers, furimazine (a coelenterazine derivative substrate for NANOLUC; Promega Corp.) was added at a concentration of 20 uM, and BRET was quantified on a Varioskan luminometer. The specific BRET signal was calculated by subtracting the non-specific signal (in the presence of unlabeled SAHA) from the signal generated from the SAHA tracer alone.

Results in FIGS. 2A-B demonstrate that the SAHA-TOM (PBI-4968) conjugate/tracer generated a superior, specific BRET signal compared to SAHA-TMR (PBI-4967) and also generated a left-shifted $EC_{50}$ value for binding within living cells. As a drug conjugate for BRET applications, the benefit of the PBI-4968 TOM dye over other commonly used fluorophores can be applied to competitive binding assays or target identification (chemical proteomics) screening using NANOLUC fusion protein libraries.

While this example demonstrates the binding of a drug tracer to a known high-affinity target, in other embodiments such a tracer is combined with a library of NANOLUC fusion proteins to profile relative drug affinities and specificities across target families. In such embodiments, profiling efforts aide in identification of drugs with promiscuous binding profiles, which may correlate with undesirable drug side effects in vivo.

Example 2

Experiments were conducted during development of embodiments of the present invention to demonstrate the unexpected benefit of low expression levels of NANOLUC for BRET applications.

Figure 3A:
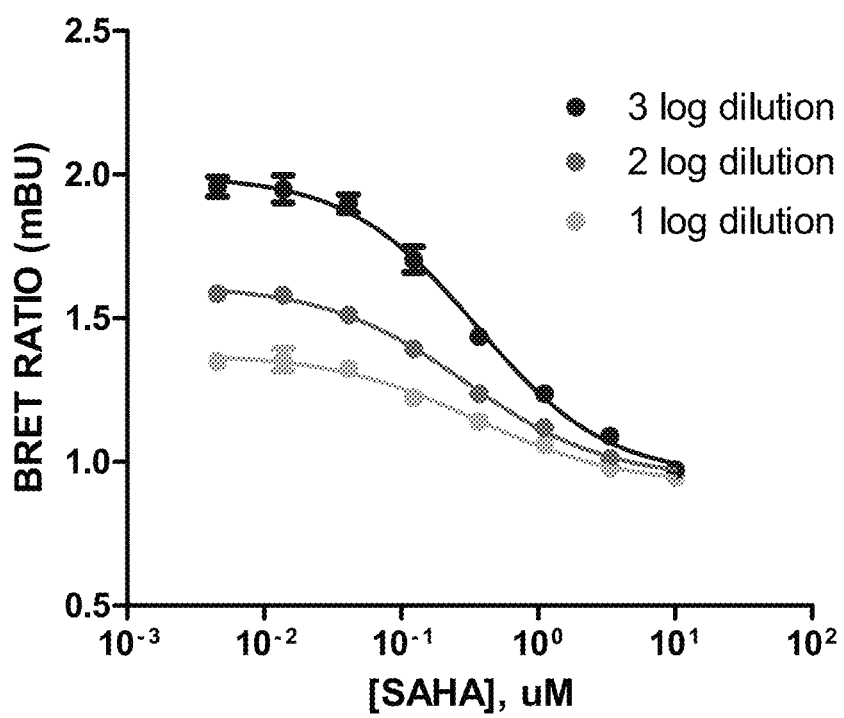

A) HEK293 cells were transfected using Fugene HD with varying amounts of NANOLUC-HDAC6 DNA and seeded in a 96-well plate format. For the transfection, NANOLUC-HDAC6 DNA was diluted with promoterless carrier DNA (pGEM3Z). The final DNA concentration/well remained 50 ng/well; however the NANOLUC-HDAC6 DNA was diluted 1:10, 1:100, and 1:1000 (at a seeding density of 20,000 cells/well in 96-well format). Twenty-four hours post-transfection, cells were treated with serially-diluted SAHA in the presence of a fixed concentration (1 uM) of SAHA-TOM (PBI-4968; See FIGS. 8A-B) conjugate. After two hours of incubation, furimazine was added to 20 uM, and BRET detected on a Varioskan luminometer. The results in FIGS. 3A-B demonstrate that an unexpectedly high dilution of DNA encoding the NANOLUC fusion was required to achieve proper signal to background for BRET applications.

B) DNA encoding a NANOLUC-Histamine H1 (GPCR) fusion protein was transfected into HEK293 cells using varying amounts of DNA ranging from undiluted to 1:10,000 (diluted with promoterless carrier DNA (pGEM3Z as described above) to maintain a constant amount of DNA/transfection as described above). Twenty-four hours post-transfection, cells were treated with serially-diluted with mepyramine-bodipy-633 (CellAura) and equilibrated for 2 hours. Cells were then treated with furimazine to a concentration of 20 uM, and BRET detected on a Varioskan luminometer.

Figure 3B:
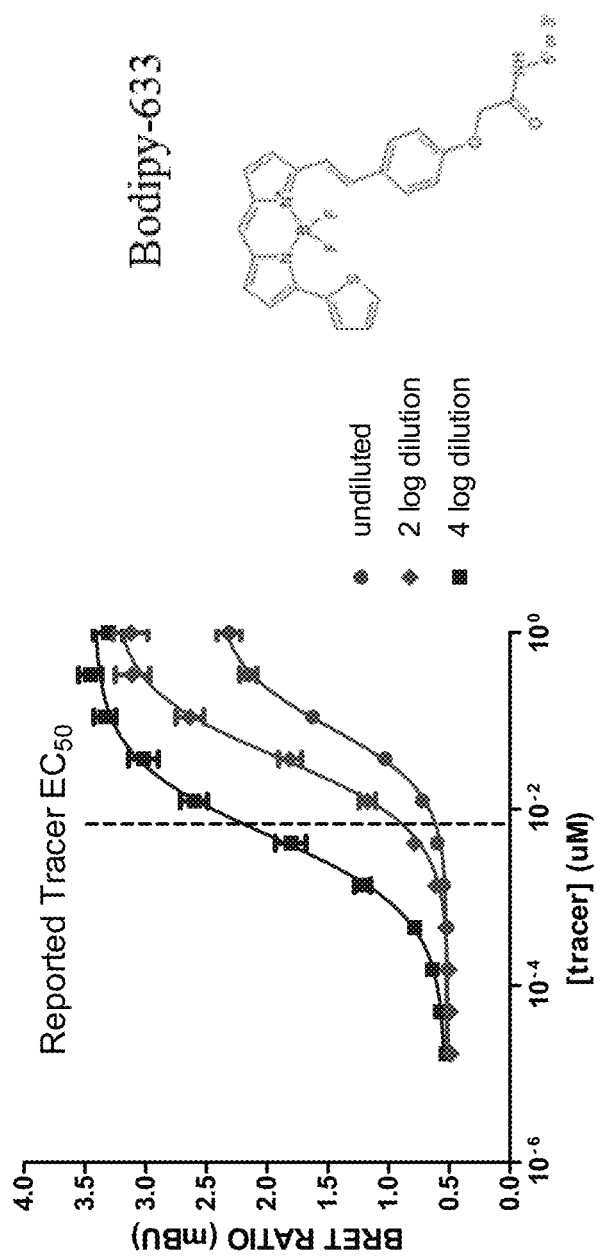

The results in FIG. 3B indicate that a large dilution of DNA encoding the NANOLUC fusion was required to generate a high affinity interaction with optimal signal-to-background. The ability to dilute NANOLUC fusion proteins to exceedingly low levels is beneficial in various BRET applications, including competitive binding assays or target identification (chemical proteomics) screening of NANOLUC fusion proteins.

Example 3

Experiments were conducted during development of embodiments of the present invention to demonstrate the predictive value of intracellular BRET measurement for quantifying the binding of pro-drugs compared to traditional biochemical (activity-based) formats. The example includes the natural pro-drug, FK228, which requires the reducing environment of the cell cytoplasm to become activated and capable of binding to HDAC6.

HEK293 cells were transfected with DNA encoding NANOLUC-HDAC6 at a 1:1000 dilution with carrier DNA as previously described. Twenty-four hours post-transfection, cells were incubated with serially-diluted natural pro-drug, FK-228; in the presence of a fixed concentration (1 uM) of SAHA-TOM (PBI-4968) conjugate. For comparison, a biochemical, activity-based HDAC6 assay was run in parallel. Briefly, a 3-fold serial dilution of FK-228 (Selleckchem catalog #S3020) was performed at 100× in 100% DMSO in wells of a 96-well plate. A 5 µL aliquot of this 100×/100% DMSO titration series was added to 245 µL of HDAC-Glo™ I/II assay buffer alone (Promega Corp.) or 245 µL of HDAC-Glo™ I/II assay buffer supplemented with 2× (0.5 mM) DTT to make a 2×/2% DMSO master intermediate titration series of FK-228 in wells of a 96-well plate. From this master intermediate titration series, 5 replicates were transferred to wells of a white 384-well assay plate (Corning 3673). A 5 addition of 2×(2 nM) HDAC 6 (BPS Bioscience catalog #50006) was added to all wells for a final concentration of 1 nM HDAC6/well. The 104, enzyme/inhibitor mixes was allowed to pre-incubate for 45 minutes at room temperature. An equal volume (10 µL) of HDAC-Glo™ I/II Final Detection Reagent (Promega Corp.) was added to all wells (20 µL final assay volume), and luminescence was measured after a 10 minute incubation at room temperature. For all test conditions, the final concentration of HDAC-Glo™ I/II substrate was 50 µM. The data was plotted (sigmoidal dose response—variable slope) using Prism™ software from GraphPad (no DTT: closed circles; 0.25 mM DTT: open squares).

The results in FIGS. 4A and 4B indicate the requirement of the cellular milieu for measuring binding of pro-drugs that must be processed by the cell to become activated.

Example 4

Experiments were conducted during development of embodiments of the present invention to demonstrate the use of permeabilization agents to introduce impermeable drug tracers to cells.

HEK293 cells were transfected with DNA encoding PKCalpha (PKCa)-NANOLUC or NANOLUC-PKCalpha at a 1:1000 dilution of DNA with promoterless carrier DNA as described previously. Twenty-four hours post-transfection, cells were treated with or without digitonin to a final concentration of 50 ug/mL. Cells were then treated with serially-diluted a staurosporine-PBI-dye conjugate (PBI-5129; See FIGS. 8A-B). Cells were co-incubated in the presence or absence of 5 uM unconjugated staurosporine as a specificity control for binding. Following two hours of equilibration with a tracer, furimazine was added to a final concentration of 20 uM, and BRET ratios were measured on a Varioskan luminometer (FIGS. 5A and 5B).

In a second experiment, identically-transfected PKCa-NANOLUC cells were treated with serially diluted digitonin prior to treatment with a fixed concentration of staurosporine-TOM (PBI-5129; See FIGS. 8A-B) tracer (5 uM final concentration) in the presence or absence of 5 uM unlabeled staurosporine (specificity control) (FIG. 5C).

Figure 5C:
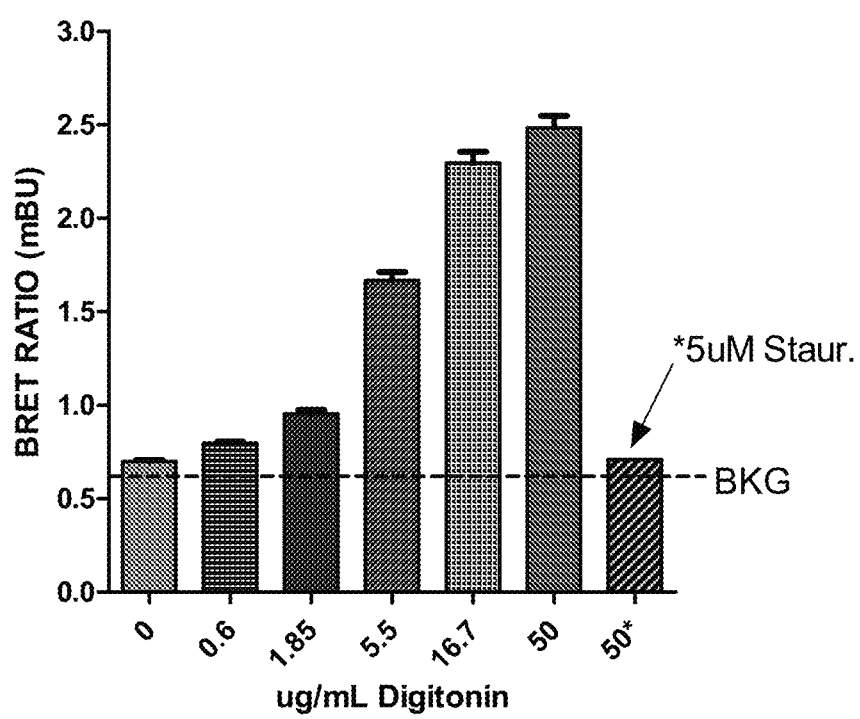

FIG. 5A-C demonstrate the ability to use permeabilization agent to potentiate the entry of impermeable drug tracers and applied to BRET-based chemical proteomics screens of NANOLUC™ fusion protein libraries.

Example 5

Experiments were conducted during development of embodiments of the present invention to demonstrate the use of NANOLUC/BRET to measure relative drug affinities in living cells. In some embodiments, similar experiments are configured to optimize leads from high-throughput chemical screens.

HEK293 cells were transfected with DNA encoding a NANOLUC-p38 fusion protein (to a final concentration of 50 ng/well DNA in 96-well format). Twenty-four hours post-transfection, cells were treated with serially diluted BIRB-796 or PBI-4835 in the presence of 0.5 uM PBI-4838 (BIRB796 dye conjugate derivative; see, e.g., U.S. Ser. No. 13/682,589; herein incorporated by reference in its entirety).

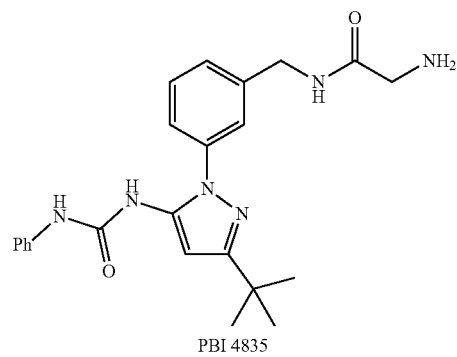 [SMILES: CC(C)(C)c1cc(NC(=O)Nc2ccccc2)n(-c2cccc(CNC(=O)CN)c2)n1]

PBI 4835

After two hours of equilibration, furimazine was added to a concentration of 20 uM, and BRET was measured on a Varioskan luminometer.

Figure 6:
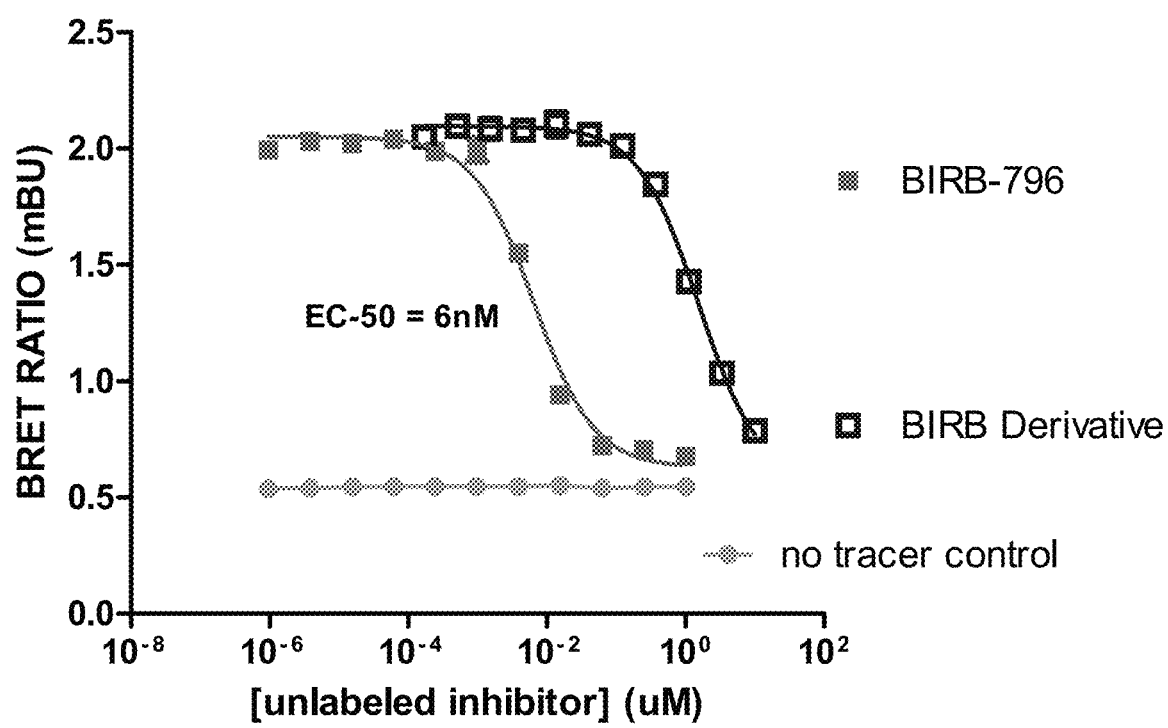

FIG. 6 demonstrates that the dose-response BRET curves support the higher known affinity of BIRB-796 over PBI-4835. The ability to measure the relative affinities of unlabeled drugs can be applied to HTS screens, lead optimization or chemical proteomics applications. In some embodiments, similar experiments are configured to characterize optimized lead compounds from high-throughput chemical screens (e.g., compounds with lower IC50 values for tracer displacement would indicate higher binding efficiency to the target of interest).

Example 6

Experiments were conducted during development of embodiments of the present invention to demonstrate the use of NANOLUC/BRET to monitor the kinetics of drug binding in living cells. In some embodiments, similar experiments are configured to optimize leads from high-thoughput chemical screens.

HEK293 cells were transfected with DNA encoding a NANOLUC-p38 fusion (to a final concentration of 50 ng/well DNA in 96-well format). Twenty-four hours post-transfection, cells were pretreated for 2 hours with protected furimazine (PBI-4378; See FIGS. 8A-B) to a final concentration of 20 uM. BRET was measured over time on a Varioskan luminometer set to 37° C. After a short pre-read, cells were stimulated with varying concentrations of PBI-4838 (in the presence or absence of 1 uM BIRB796 as a specificity control). Dose and time-dependent increases in BRET were then monitored kinetically over 4 hours.

In a separate experiment, transfected cells were pretreated with both 20 uM PBI-4377 and 1 uM PBI-4838 to generate a steady BRET signal.

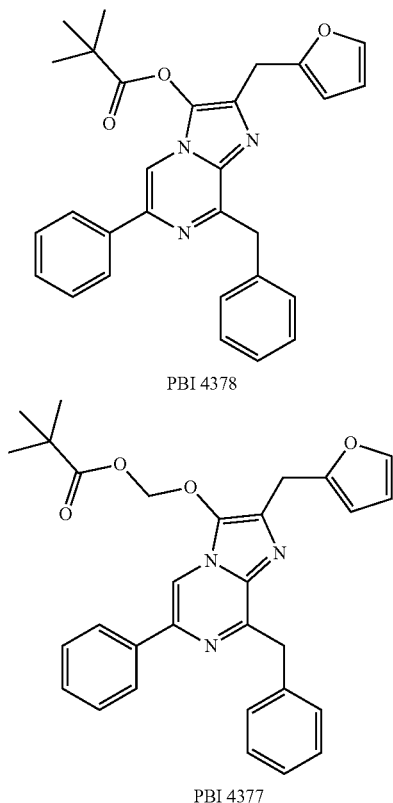 [SMILES: CC(C)(C)C(=O)Oc1c(Cc2ccco2)nc2c(Cc3ccccc3)nc(-c3ccccc3)cn12 ; CC(C)(C)C(=O)OCOc1c(Cc2ccco2)nc2c(Cc3ccccc3)nc(-c3ccccc3)cn12]

PBI 4378

PBI 4377

After a short pre-read, cells were stimulated with 1 uM unlabeled BIRB-796, and competitive displacement was monitored by BRET in real-time.

The results in FIG. 7A-B support use of BRET for monitoring binding and displacement of drug tracers in living cells. Such formats can be exploited for HTS or chemical proteomics screening of NANOLUC fusion proteins in live cells. In some embodiments, similar experiments are configured to characterize optimized lead compounds from high-throughput chemical screens (e.g., compounds with altered kinetics of displacement by a fluorescent drug tracer indicate altered binding kinetics to the target of interest).

Example 7

The following example relates to the use of specific NANOLUC™ substrates (SEE FIG. 8) or enzyme components to discriminate the subcellular localization of a drug binding event using BRET.

The physical separation of complementary NANOLUC™ enzyme polypeptides or peptide allows the isolation of NANOLUC (donor) signal to the extracellular space. For example, the small signal peptide is genetically tethered to a cell surface receptor. Upon exogenous addition of the large signal polypeptide to the cell medium, the donor signal is isolated to the extracellular space. This signal isolation increases the signal/background generated in various BRET applications including drug tracer binding/displacement.

In some embodiments, full length NANOLUC™ protein fusions are utilized if impermeable NANOLUC™ substrate is applied.

Example 8

The following provides synthesis schemes for exemplary compounds that find use in embodiments of the present invention.

Boc-Protected SAHA Amine

7-Trityloxycarbamoyl heptanoic acid (200 mg, 463 umol) was combined with 4-[(N-Boc)aminomethyl]aniline (113 mg, 510 umol), HBTU (352 mg, 927 umol) and triethylamine (194 uL, 1.4 mmol) in 3 mL of DMF. The reaction was stirred overnight, then adsorbed onto Celite, and the product was obtained by column chromatography eluting with a gradient of 0->100% EtOAc in heptanes. Calcd for M+H: 635.3; found 635.9.

SAHA Amine

Suberoyl(4-[(N-Boc)aminomethyl]anilide) hydroxamic acid (286 mg, 450 mmol) was dissolved in 2 mL of DCM to which was added 0.25 mL of TIS. Trifluoroacetic acid (0.9 mL) was then added, and the reaction was stirred for 30 min. Solvents were removed under reduced pressure, and the crude reaction product could be purified by preparative HPLC or used without further purification.

PBI-4967 SAHA-TAMRA

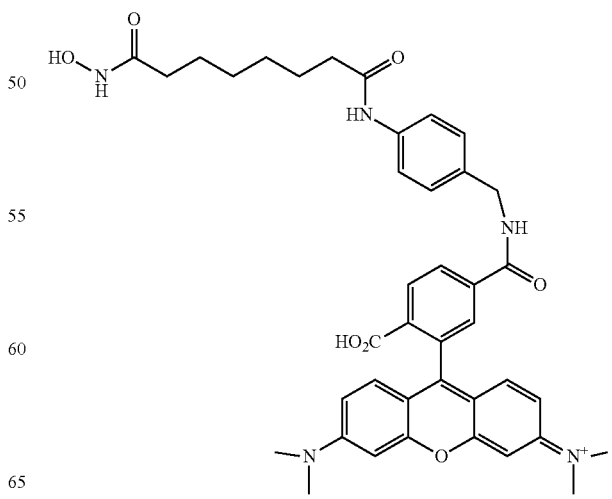

Suberoyl[4-(aminomethyl)anilide] hydroxamic acid crude reaction product (27 mg) was combined with 4 mg (7.6 umol) of tetramethylrhodamine6-succinimidyl ester in 1 mL of DMF with 5 drops of TEA. After 30 min, the reaction was diluted with H₂O and MeCN, and the product was isolated by preparative HPLC (5->60% MeCN in 0.1% aqueous TFA). Lyophilization of the appropriate fractions yielded the desired product as a magenta solid. Calcd for M+H: 706.3; found 706.6.

PBI-4968 SAHA-TOM

PBI-5129 Staurosporine-TOM

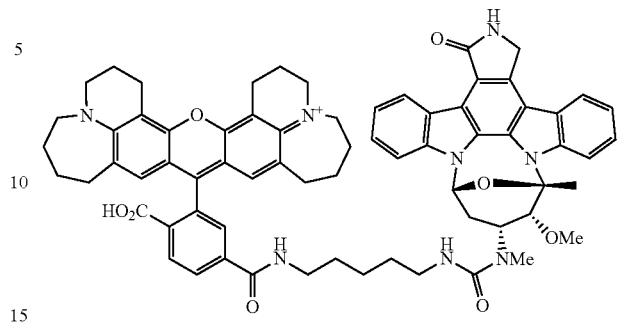

Staurosporine 5-aminopentylcarboxamide (5 mg, 8.4 umol) was dissolved in 1 mL DMF and treated with triethylamine and TOM 6-SE (4 mg, 6 umol). The reaction was monitored by analytical HPLC. Upon completion of the reaction, MeCN and H₂O were added, and the TEA was neutralized by addition of a small amount of AcOH. Preparative HPLC (25%->100% MeOH in 10 mM NH4OAc) and subsequent concentration yielded 1.8 mg of a dark blue solid. Calcd for M+H: 1139.5; found 1139.8.

Dasatinib-TOM

TOM-pentylamine

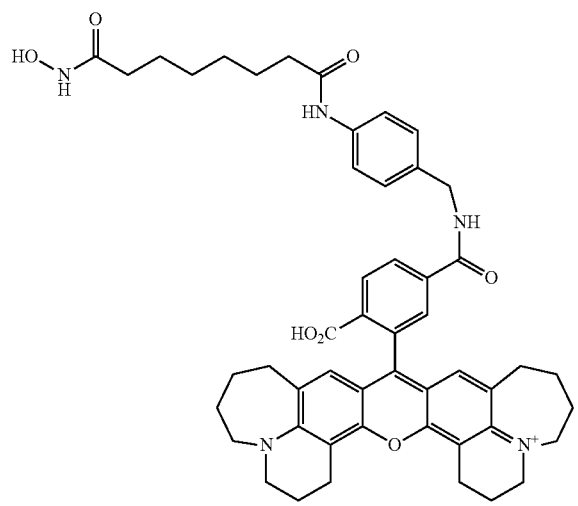 [SMILES: O=C(CCCCCCC(=O)Nc1ccc(CNC(=O)c2ccc(C(=O)O)c(C3=c4cc5c6c(c4Oc4c3cc3c7c4CCCN7CCCC3)CCC[N+]=6CCCC5)c2)cc1)NO]

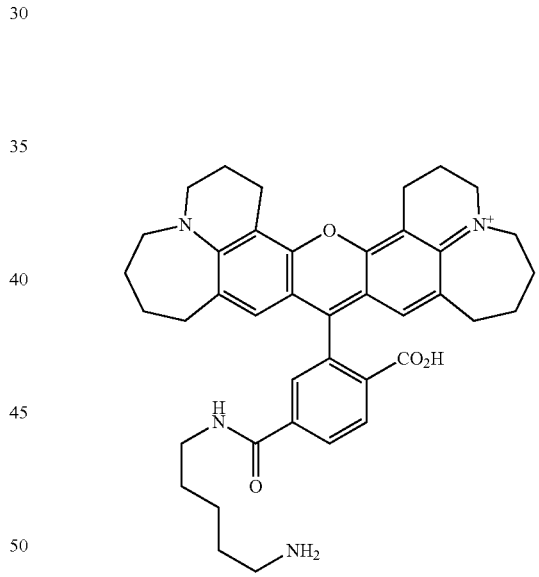

Suberoyl[4-(aminomethyl)anilide] hydroxamic acid crude reaction product (8 mg) was combined with 5 mg (7.6 umol) of TOM 6-succinimidyl ester in 0.8 mL of DMF with 3 drops of TEA. After 30 min, the reaction was diluted with H₂O and MeCN, and the product was isolated by preparative HPLC (5->60% MeCN in 0.1% aqueous TFA). Lyophilization of the appropriate fractions yielded the desired product. Calcd for M+H: 838.4; found 838.7.

Staurosporine-Amine

Staurosporine p-nitrophenylcarbamate (3 mg, 4.8 umol) was dissolved in 0.5 mL of DMF and treated with excess cadaverine. The reaction was warmed in a 70° C. oil bath for 2 h, then diluted with H₂O, acidified with formic acid, and subjected to preparative HPLC eluting with 25%->75% MeCN in 10 mM aqueous NH₄OAc. The appropriate fractions were lyophilized to afford a slightly yellow solid. Calcd for M+H: 595.3; found 595.5.

TOM 6-carboxylic acid (26 mg, 46 umol) was stirred in 1 mL of DMF with 2 equiv of triethylamine and treated with TSTU (17 mg, 56.5 umol, 1.2 equiv), and the reaction was monitored by HPLC. After 40 min, the reaction was added to a solution of cadaverine (94 mg, 0.92 mmol, 20 equiv) in 0.5 mL DMF and stirred for 20 min. The reaction was then neutralized by addition of TFA and diluted with MeCN and water. Preparative HPLC (25->100% MeCN in 0.1% aqueous TFA) and subsequent lyophilization afforded the desired product as a purple solid. LCMS: Calcd for ((M+2H)/2) 324.4; found 324.3.

Dasatinib-TOM

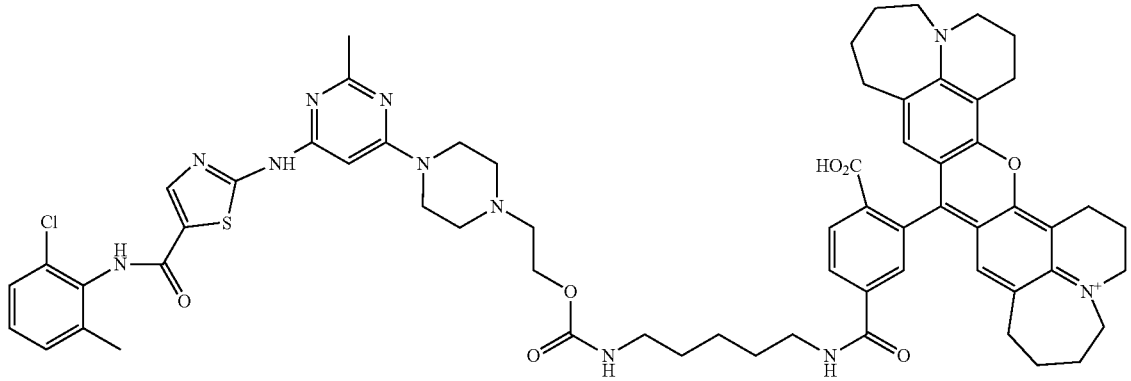 [SMILES: Cc1nc(Nc2ncc(C(=O)Nc3c(C)cccc3Cl)s2)cc(N2CCN(CCOC(=O)NCCCCCNC(=O)c3ccc(C(=O)O)c(C4=c5cc6c7c(c5Oc5c4cc4c8c5CCCN8CCCC4)CCC[N+]=7CCCC6)c3)CC2)n1]

Dasatinib (25 mg, 51 umol) was combined with p-nitrophenyl chloroformate (14 mg, 69 umol, 1.36 equiv) and 30 uL TEA in 0.9 mL of 2:1 DMF:THF. The reaction was stirred overnight and then 35 mg additional p-nitrophenyl chloroformate added. After stirring for an additional 24 h, ½ the volume of the reaction was added to a solution of 7 mg (10 umol) of TOM-pentylamine in 0.5 mL of DMF and 30 uL TEA. The reaction was then stirred for 1 h, followed by dilution with MeCN and water and purification by preparative HPLC. Lyophilization afforded the desired product as a purple solid. MS: Calcd for ((M+2H)/2) 580.8; found 581.0.

Purvalanol-TOM PBI 5077

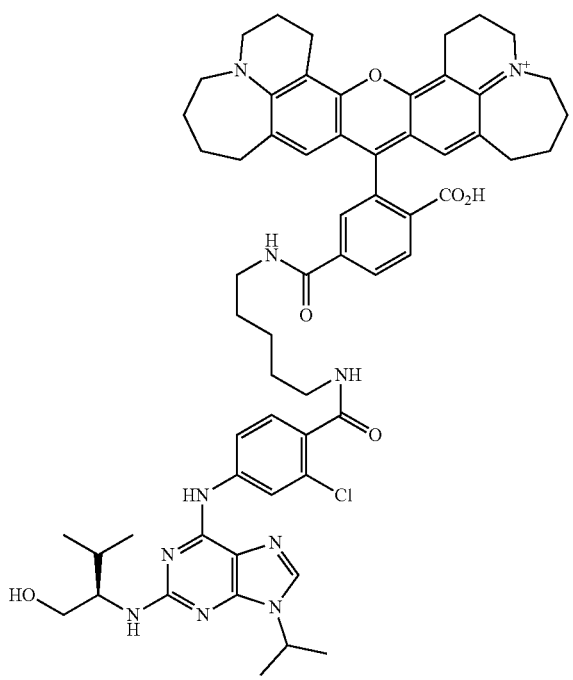 [SMILES: CC(C)[C@H](CO)Nc1nc(Nc2ccc(C(=O)NCCCCCNC(=O)c3ccc(C(=O)O)c(C4=c5cc6c7c(c5Oc5c4cc4c8c5CCCN8CCCC4)CCC[N+]=7CCCC6)c3)c(Cl)c2)c2ncn(C(C)C)c2n1]

Purvalanol (10 mg, 23 umol) was stirred in 1 mL of DMF with 20 mg of TEA (198 umol) and treated with 7.7 mg (25.4 umol, 1.1 equiv) of TSTU. After 30 min, the reaction was diluted with Et2O and ½ of the total reaction volume was added to a vial containing 6 mg (9 umol) of TOM (5-aminopentyl)-6-carboxamide. The reaction was stirred for 3 h, and the volatile organics were removed under reduced pressure. The resulting DMF solution was diluted with water and MeCN and acidified with TFA, then the product was isolated by preparative HPLC (25->100% MeCN in 0.1% aqueous TFA) and subsequent lyophilization to yield 3.5 mg of a purple solid. MS: Calcd for M+H: 1061.5, found 1061.6.

Example 9

Use of *Renilla* Luciferase or NANOLUC Luciferase in the Compound Identification Method of the Present Invention HEK293 cells were transfected with plasmid DNA encoding NANOLUC-p38alpha or *Renilla* Luc-p38alpha using Fugene HD(Promega Corporation) at a 3:1 lipid:DNA ratio and seeded into 96-well plates at a density of 20,000 cells per well (to yield 50 ng/well of DNA). 24 h post-transfection, cell medium was replaced with serum-free medium (Opti-MEM) and incubated with serially-diluted PBI-4838 (BIRB796 derivative conjugated to TOM dye) in the presence/absence of BIRB796 at 1 uM. Cells were incubated at 37° C. for two hours. To the NANOLUC-expressing samples, furimazine was added to a final concentration of 20 uM. To the *Renilla* Luc-expressing samples, native coelenterazine was added to a final concentration of 20 uM. BRET was then measured on a Varioskan luminometer equipped with 450 nm bandpass and 630 nm longpass filters. The BRET ratio was determined by dividing the signal in the 630 channel by the signal in the 450 channel.

Figure 9A:
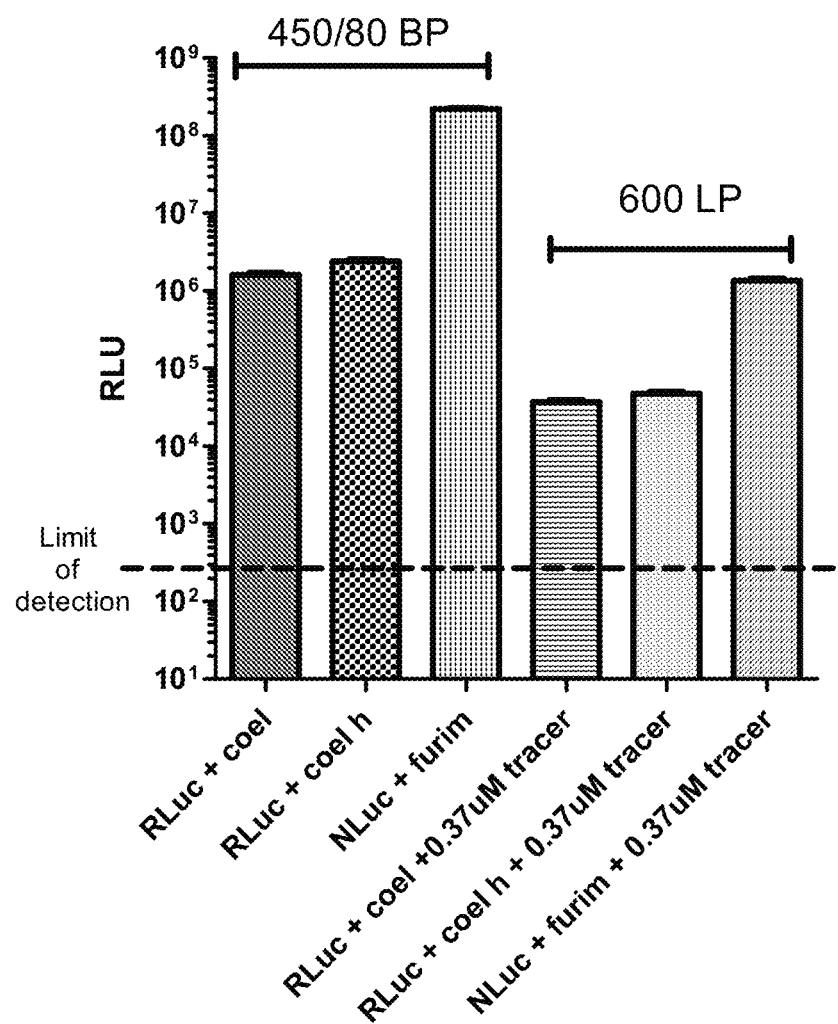
Figure 9B:
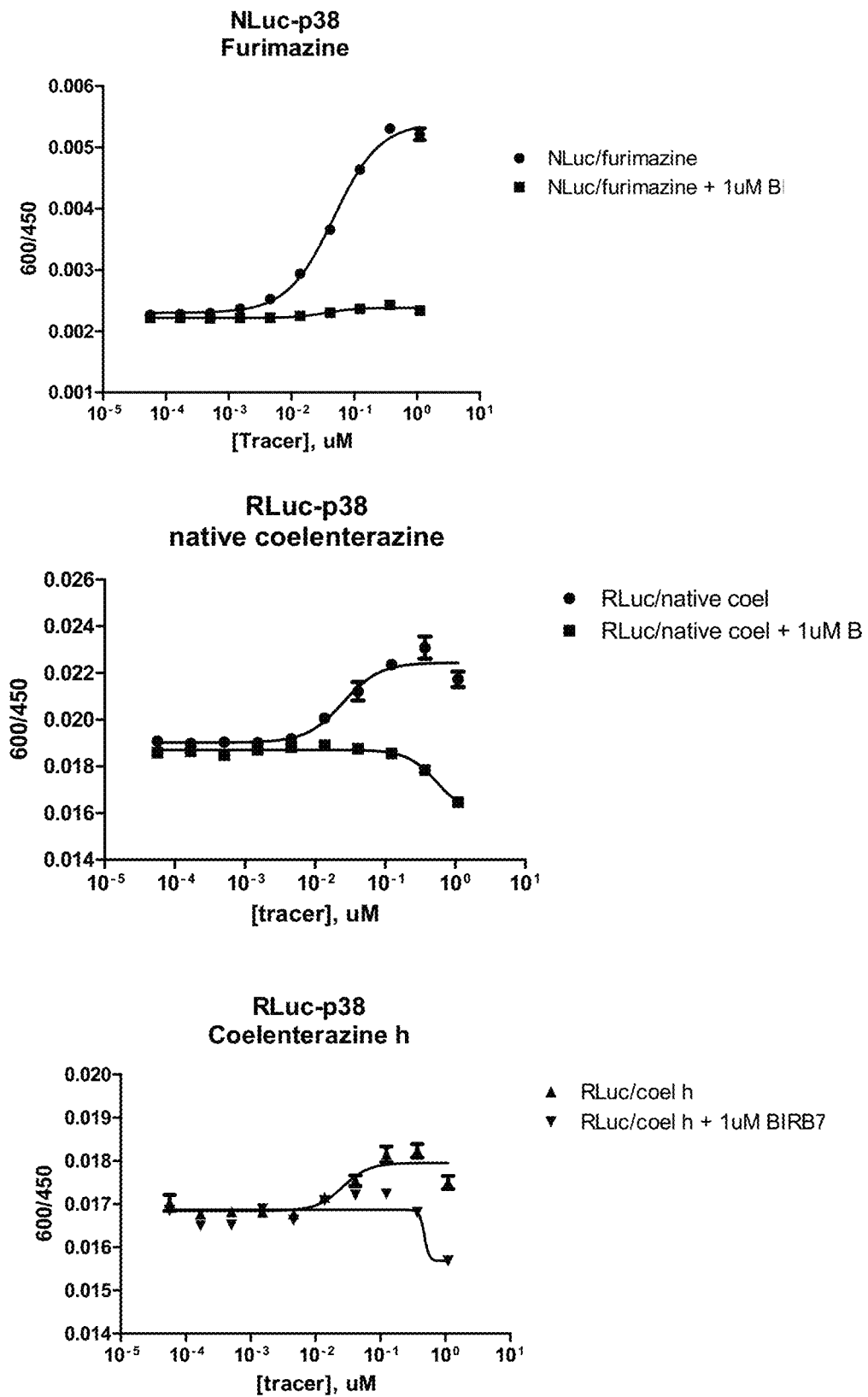

FIGS. 9A-B demonstrates that both *Renilla* luciferase and NANOLUC luciferase can be used in the method of the present invention. Upon treatment of cells expressing NANOLUC-p38alpha or *Renilla* Luc-p38alpha with serially-diluted PBI4838, a dose-dependent increase in BRET is observed. Saturating concentrations of unlabeled BIRB-796 are able to block this BRET signal, indicating specificity of binding using either luciferase fusion to p38alpha.

Example 10

Comparison of TOM-BIRB Vs. TMR-BIRB Against NANOLUC-p38 Alpha

As described above, HEK293 cells were transfected with plasmid DNA encoding NANOLUC-p38alpha using Fugene HD and seeded into 96-well plates (to yield 50 ng/well of DNA). 24 h post-transfection, cell medium was replaced with serum-free medium (Opti-MEM) and incubated with serially-diluted PBI4838 (BIRB796 derivative conjugated to TOM dye) or PBI-4836 (BIRB derivative conjugated to TMR dye) in the presence/absence of BIRB796 at 1 uM. Cells were incubated at 37° C. for two hours. To the NANOLUC-expressing samples, furimazine was added to a final concentration of 20 uM. BRET was then measured on a Varioskan luminometer equipped with 450 nm bandpass and 630 nm longpass filters. The BRET ratio was determined by dividing the signal in the 630 channel by the signal in the 450 channel.

FIGS. 10A-B demonstrates another example of the increased potency of the TOM adduct over the TMR adduct for binding to a target protein in a cell-based format. Dose-response curves for NANOLUC-p38alpha binding indicate an EC50 of 38 nM for the BIRB-TOM conjugate, compared to an EC50 of 450 nM for the BIRB-TMR conjugate. The reported affinity of BIRB-TOM is more consistent with literature reports compared to the BIRB-TMR (Chem Biol Drug Des 2009; 74: 547-559).

Example 11

Comparison of BIM-TOM Vs. BIM-TMR Against PKCalpha-NANOLUC

As described above, HEK293 cells were transfected with plasmid DNA encoding PKCalpha-NANOLUC (diluted 1:1000 into pGEM3Z carrier DNA) using Fugene HD and seeded into 96-well plates (to yield 50 ng/well of total DNA). 24 h post-transfection, cell medium was replaced with serum-free medium (Opti-MEM) and incubated with serially-diluted PBI-5075 (BIM conjugated to TOM dye) or PBI-5051 (BIM conjugated to TMR dye) in the presence/absence of staurosporine at 5 uM. Cells were incubated at 37° C. for two hours. To the NANOLUC-expressing samples, furimazine was added to a final concentration of 20 uM. BRET was then measured on a Varioskan luminometer equipped with 450 nm bandpass and 630 nm longpass filters. The BRET ratio was determined by dividing the signal in the 630 channel by the signal in the 450 channel. To determine specific BRET signals, the BRET ratio at each concentration of tracer+unlabeled staurosporine was subtracted from the BRET ratio at each concentration of tracer without unlabeled staurosporine.

Figure 11:
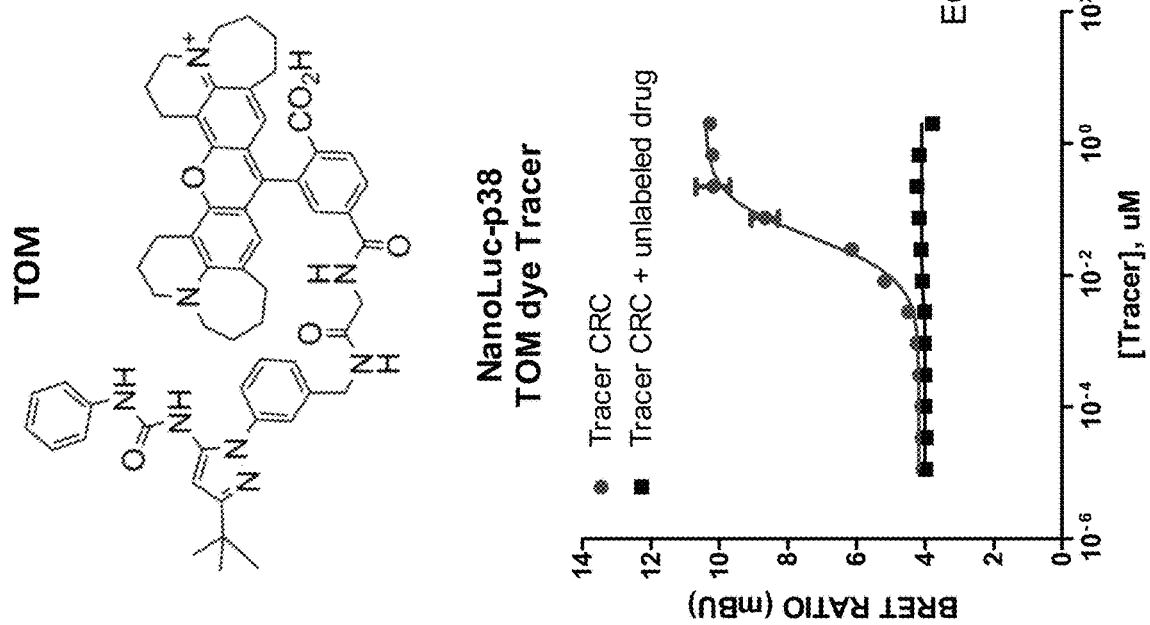
FIG. 11 shows dose-response curves for PKCalpha-NANOLUC binding to a BIM-TOM conjugate compared to a BIM-TMR conjugate.

FIG. 11 demonstrates another example of the increased potency of the TOM adduct over the TMR adduct for binding to a target protein in a permeabilized cell format. Dose-response curves for PKCalpha-NANOLUC binding indicate an EC50 of 483 nM for the BIM-TOM conjugate, compared to dramatically right-shifted potency for the BIM-TMR conjugate. The reported affinity of BIM-TOM is more consistent with literature reports compared to the BIM-TMR (J Biol Chem. 1991 Aug. 25; 266(24):15771-81.).

Example 12

Target Identification Across p38/MAPK Pathway-Determination of Selectivity

The following example serves to demonstrate the ability to profile the selectivity of a drug tracer against a panel of putative targets within a given phylogenetic target family. Similar experimental configurations may be used to identify the target of fluorescently labeled drugs using BRET in cells. This configuration may lead to the identification of the primary drug target, as well as off-target interactors. Engagement of multiple targets may be indicative of drug promiscuity and potential drug side effects. This example serves to demonstrate the ability to measure both primary, as well s secondary target interactions via BRET.

HEK293 cells were transfected with plasmid DNA encoding N or C-terminal NANOLUC fusions to various members of the MAPK pathway (Jnk1, Jnk2, Jnk3, p38alpha, p38beta, p38gamma, p38 delta, or PKCalpha or MAPK 8, 9, 10, 14, 11, 12, or 13, PKCalpha respectively) using Fugene HD (Promega Corporation) at a 3:1 lipid:DNA ratio and seeded into 96-well plates at a density of 20,000 cells per well (yield 50 ng/well of DNA). Twenty-four hours post-transfection, cell medium was replaced with serum-free medium (Opti-MEM) and incubated with 2 uM PBI-4838 in the presence or absence of BIRB796 at 4 uM. Cells were incubated at 37° C. for two hours. To the NANOLUC-expressing samples, furimazine was added to a final concentration of 20 uM. BRET was then measured on a Varioskan luminometer equipped with 450 nm bandpass and 630 nm longpass filters. The BRET ratio was determined by dividing the signal in the 630 channel by the signal in the 450 channel. To determine response ratios, the BRET values with tracer alone were divided by the BRET values with tracer+unmodified BIRB796.

Figure 12:
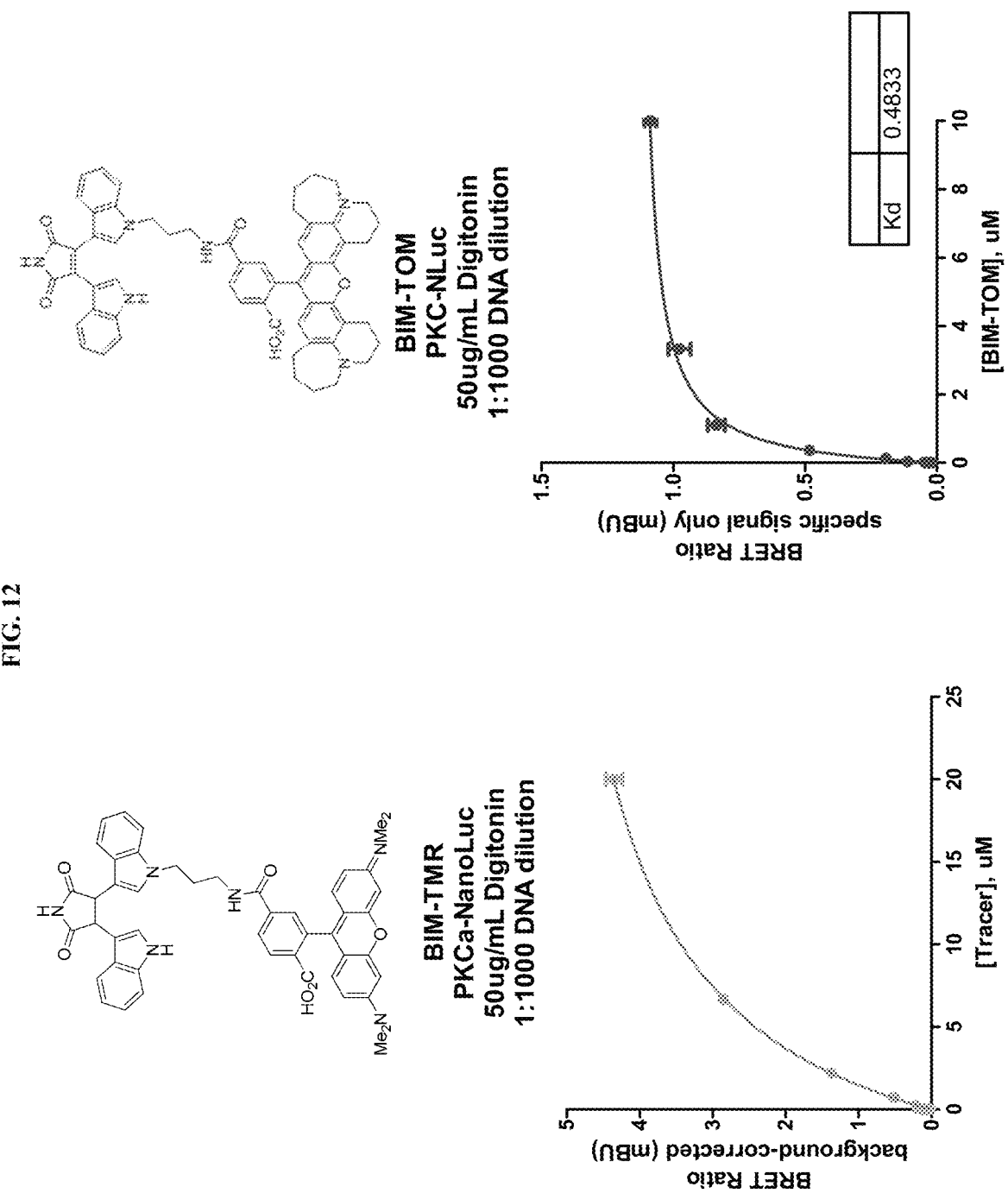
FIG. 12 shows selectivity of PBI-4838 to Jnk2, p38beta and p38alpha.

FIG. 12 indicates selectivity of PBI-4838 to Jnk2, p38beta and p38alpha, consistent with literature reports. P38alpha is recognized as the primary target of BIRB796. However, interactions with targets such as Jnk2 and p38beta could indicate potential off-target liabilities. As expected, PKCalpha showed relatively little specific BRET signal owing to poor affinity of BIRB796 toward this target.

Example 13

Target Identification Across p38/MAPK Pathway-Determination of Affinity

The following example serves to demonstrate the ability to profile the affinity of a drug tracer against a panel of putative targets within a given phylogenetic target family. Similar experimental configurations may be used to characterize the affinity of the fluorescently labeled drug to a given target using BRET in cells.

HEK293 cells were transfected with plasmid DNA encoding NANOLUC-p38alpha, NANOLUC-p38beta, Jnk2-NANOLUC, PKCalpha-NANOLUC, or NANOLUC-HDAC6 using Fugene HD (Promega Corporation) at a 3:1 lipid:DNA ratio and seeded into 96-well plates at a density of 20,000 cells per well (yield 50 ng/well of DNA). Twenty-four hours post-transfection, cell medium was replaced with serum-free medium (Opti-MEM) and incubated with serially-diluted PBI-4838 in the presence or absence of BIRB796 at 4 uM. Cells were incubated at 37° C. for two hours. To a separate set of samples, transfected cells were treated with serially-diluted BIRB796 in the presence of 1 uM PBI-4838. To the NANOLUC-expressing samples, furimazine was added to a final concentration of 20 uM. BRET was then measured on a Varioskan luminometer equipped with 450 nm bandpass and 630 nm longpass filters. The BRET ratio was determined by dividing the signal in the 630 channel by the signal in the 450 channel.

Figure 13:
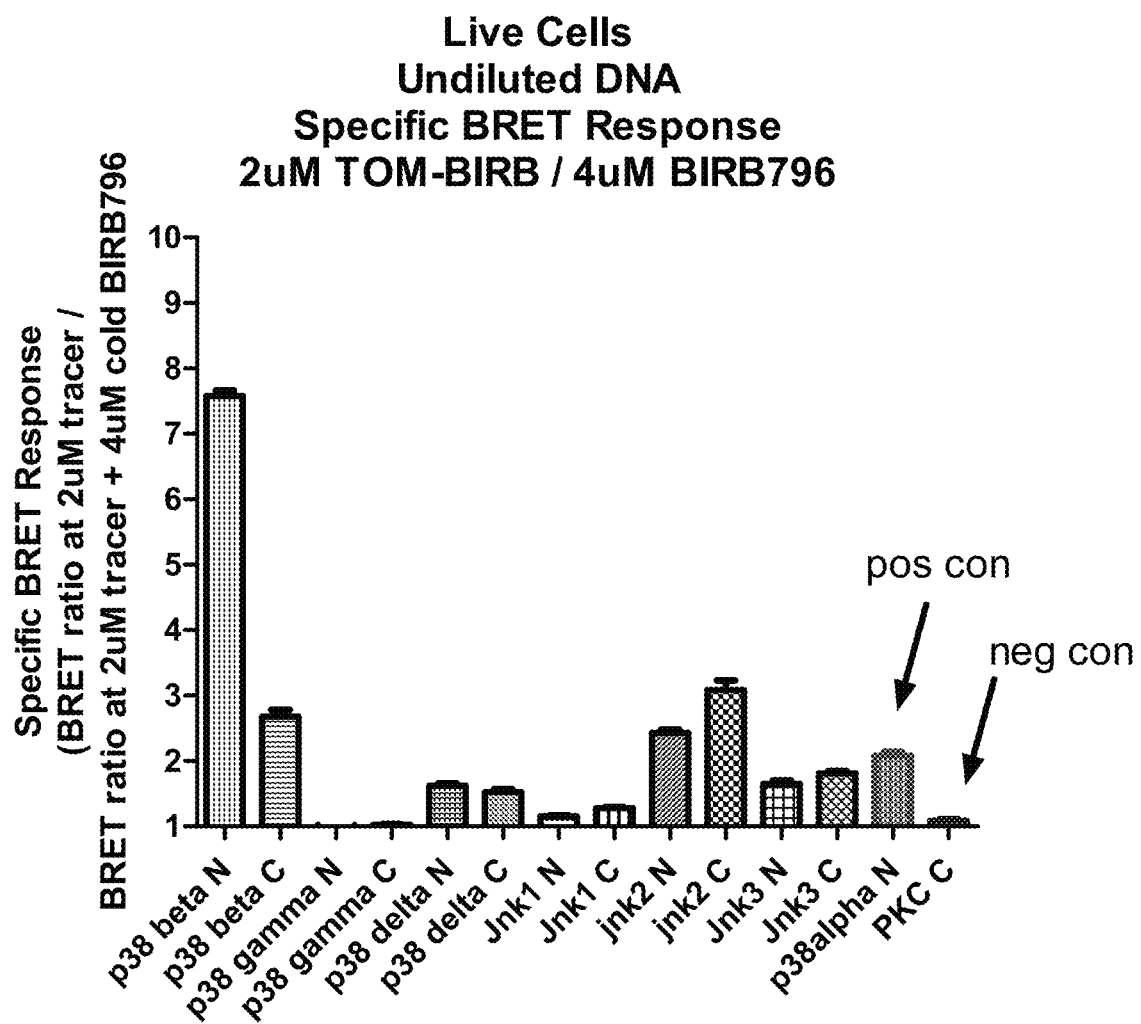
FIG. 13 shows a graph depicting detection of specific BRET response in live cells.

FIGS. 13 and 14 demonstrate the apparent affinity of PBI-4838 to Jnk2, p38beta, and p38alpha. As expected, PKCalpha and HDAC6 showed relatively little specific BRET signal owing to poor affinity of PBI-4838 to these targets. Furthermore, the high affinity of BIRB796 toward Jnk2, p38alpha, and p38beta is demonstrated by competitive displacement in cells. Similar experiments could be configured to rank-order the affinity of drug tracers to a given set of targets (by an increase in BRET) or unmodified drugs (by competitive displacement). As indicated above, high-affinity interactions with targets such as Jnk2 and p38beta could indicate potential off-target liabilities.

Example 14

Affinity Determination of a Drug Tracer for Wild-Type Versus Mutant Version of Target Protein The following example serves to demonstrate the ability to measure the relative affinity of a drug tracer to a wild-type versus mutant target protein. In this example, the affinity of a fluorescently-labeled iBET compound (small-molecule inhibitor that binds BRD4 preventing its interaction with acetylated histones) was determined for wild-type and mutant version (N140 A/N433A; lacks full binding capacity to iBET) of BRD4 (Bromodomain-containing protein 4). Similar experimental configurations may be used to characterize the affinity and selectivity of the fluorescently-labeled drug to a disease-relevant mutant protein in cells. Such experiments may be useful to identify drugs that selectively bind to wild-type or mutant proteins differentially.

HEK293 cells were transfected with plasmid DNA encoding NANOLUC-BRD4 or NANOLUC-BRD4 (N140A/N433A) using Fugene HD (Promega Corporation) at a 3:1 lipid:DNA ratio and seeded into 96-well plates at a density of 20,000 cells per well (yield 50 ng/well of DNA). Twenty-four hours post-transfection, cell medium was replaced with serum-free medium (Opti-MEM) and incubated with serially-diluted PBI-4966 (iBET conjugated to TOM dye) in the presence/absence of iBET at 10 uM. Cells were incubated at 37° C. for two hours. To the NANOLUC-expressing samples, furimazine was added to a final concentration of 20 uM. BRET was then measured on a Varioskan luminometer equipped with 450 nm bandpass and 630 nm longpass filters. The BRET ratio was determined by dividing the signal in the 630 channel by the signal in the 450 channel.

FIG. 15 indicates relative affinities of PBI-4966 to wild-type BRD4 versus the mutant BRD4. As expected, a right-shifted potency is observed with the mutant BRD4 indicating a lowered affinity for PBI-X. Similar experiments could be configured to rank the order of the affinity of drug tracers to disease-relevant mutants of a target. This principle could be expanded to measuring relative affinities of drugs toward wild-type or mutant proteins by competitive tracer displacement. Since increased BRET signal is only indicative of binding to the NANOLUC fusion, this method enables measurements of target engagement amidst a complex mixture of similar antigens present in the assay sample. These antigens could include targets of similar properties, but non-identical to the target of interest (for instance, to discriminate heterologous vs. endogenous analyte or mutant vs. wt. analyte, etc.).

Example 15

Screening Compound Panel to Determine Target Engagement

The following example demonstrates that the method of the present invention can be used to screen compound panels to determine target engagement. This screening method could be expanded to larger compound libraries (e.g. LOPAC) as well.

HEK293 cells were transfected with NANOLUC-HDAC6 DNA using Fugene HD and seeded into wells of a 96-well plate. For the transfection, NANOLUC-HDAC6 DNA was diluted with promoterless carrier DNA (pGEM3Z). The final DNA concentration/well remained 50 ng/well; however the NANOLUC-HDAC6 DNA was diluted 1:1000 (at a seeding density of 20,000 cells/well in 96-well format). Twenty-four hours post-transfection, cells were treated with serially-diluted inhibitors (SEE FIG. 17) in the presence of a fixed concentration (1 uM) of SAHA-TOM conjugate (PBI-4968). After two hours of incubation, furimazine was added to 20 uM, and BRET detected on a Varioskan luminometer.

The results in FIGS. 16A-D demonstrate that structurally-distinct compounds can be identified by competitive displacement of drug tracers using the method of the present invention. Furthermore, relative potency of various compound classes can be confirmed. The results indicate little/no binding efficiency of apicidin to HDAC6 compared to high binding efficiency of panabinostat or SAHA to HDAC6. This is consistent with literature reports using orthogonal assay formats. This screening method could be expanded to include high-throughput screening of large chemical libraries to identify/characterize new chemical matter with inhibitory potential against a given target.

Example 16

Monitoring Drug-Target Interactions

It is commonly accepted that a high degree of non-specific BRET occurs in medium containing a luciferase in the presence of a fluorophore of significant spectral overlap (Couturier 2012). This has been described as a liability to using BRET for high-throughput chemical screens. The following example serves to demonstrate the ability to monitor drug/target interactions using fluorophore-drug conjugates in the presence of a luciferase, NANOLUC, in medium at concentration ranges commonly recognized as problematic for BRET.

HEK293 cells were transfected with plasmid DNA encoding CDK2-NANOLUC (diluted 1:100 into pGEM3Z carrier DNA) using Fugene HD (Promega Corporation) at a 3:1 lipid:DNA ratio and seeded into wells of 96-well plates at a density of 20,000 cells per well (yield 50 ng/well of total DNA). Twenty-four hours post-transfection, cell medium was replaced with serum-free medium (Opti-MEM) and incubated with serially-diluted PBI-5077 (purvalanol B conjugated to TOM dye) in the presence/absence of Purvalanol B at 10 uM. Cells were incubated at 37° C. for two hours.

To the NANOLUC-expressing samples, furimazine was added to a final concentration of 20 uM. BRET was then measured on a Varioskan luminometer equipped with 450 nm bandpass and 630 nm longpass filters. The BRET ratio was determined by dividing the signal in the 630 channel by the signal in the 450 channel (FIGS. 17A-C).

This example supports use of fluorophore tracers in medium for monitoring drug/target interactions via BRET. By co-incubating the sample (+drug tracer) with purvalonol B (unmodified drug), the non-specific BRET signal between the NANOLUC and the tracer can be measured. Over the tracer concentration range tested, this background BRET signal was low. These results demonstrate that specific binding between the drug tracer and the NANOLUC-target fusion can be monitored in cell medium despite significant spectral overlap between the NANOLUC (donor) and fluorophore (acceptor).

Example 17

Target ID Screening Using Protein Arrays

The following example demonstrates the ability to generate NANOLUC fusion arrays using cell-free expression and measure drug binding and relative affinity by BRET.

A panel of 11 kinases (N- and C-terminal NANOLUC fusions) including putative targets of BIRB796 (such as members of the MAPK and Jnk families), putative targets of Dasatinib (such as Src and LCK) as well as an irrelevant HDAC6 negative control was expressed in TnT® T7 Quick Coupled Reticulocyte Transcription/Translation System (Promega Corporation) as recommended by the manufacturer to create an array with 23 different NANOLUC fusions. Each TNT® reaction was diluted 1:100 in PBS and plated in replicates into wells of 96-well plates. The NANOLUC fusion array was screened with 2 different TOM-drug tracer (BIRB-TOM; PBI-4838 and Dasatinib-TOM; PBI-5170) in the presence and absence of excess relevant free drug. For each TNT® reaction, 4 replicates with 2 uM BIRB TOM/4 replicates with 2 uM BIRB-TOM+4 uM BIRB796 (total of 2×96-well plates) and 4 replicas with 1 uM Dasatinib-TOM/4 replicates with 1 uM Dasatinib-TOM+5 uM Dasatinib (total of 2×96-well plates) were performed. The reactions were incubated with constant mixing for 2 h at room temperature. Following the incubation, furimazine was added to a final concentration of 20 uM. BRET was then measured on a Varioskan luminometer equipped with 450 nm bandpass and 610 nm longpass filters. The BRET ratio was determined by dividing the signal in the 610 channel by the signal in the 450 channel. To determine response ratios, the BRET values with tracer alone were divided by the BRET values with tracer+unmodified.

The results (FIG. 18) demonstrate selectivity of the BIRB-TOM tracer to JNk2, JNk3, MAPK14, MAPK11 and MAPK13 as well as selectivity of the Dasatinib-TOM tracer to ABL1, Src, LCK, MEK5, MAPK11 and MAPK14 consistent with literature reports. These results demonstrate the ability to profile the drug tracer's against a panel of putative targets expressed in cell free expression system and to identify hits. This no wash protein NANOLUC fusion array configuration may lead to the identification of the primary drug target, as well as off-target interactors.

Following the above screen, the BIRB-TOM hits were further analyzed for binding affinity to the BIRB-TOM tracer and competitive displacement of the BIRB TOM Tracer with the BIRB796. Binding affinity experiments to the BIRB-TOM tracer were preformed by incubating 3 replicates of the diluted TNT reactions with serially-diluted BIRB-TOM tracer in the presence/absence of BIRB796 at 10 uM. Reactions were incubated at room temperature with constant mixing for two hours and after adding furimazine to a final concentration of 20 uM analyzed as described above. Competitive displacement experiments were preformed by incubating 3 replicates of the diluted TNT reactions with serially-diluted BIRB796 in the presence of BIRB-TOM tracer at 2 uM. Reactions were incubated at room temperature with constant mixing for two hours and after adding furimazine to a final concentration of 20 uM analyzed as described above. The competitive displacement experiments results in FIG. 19 indicates that BIRB796 had highest affinity to MAPK14 and Jnk2 with lower affinity to MAPK11, MAPK13, and Jnk3. Consistent with literature reports, BIRB796 binds efficiently to MAPK14, but also engages other MAPK and Jnk family members indicating off-target liabilities for BIRB-796. These results demonstrate that hits expressed in cell free expression systems and identified in the protein array screen can be further analyzed by BRET for binding affinity to the drug. Furthermore thee results supports the use of cell-free expression systems to generate NANOLUC protein fusions as suitable analytes for target engagement applications.

Example 18

Expression Level of NANOLUC Fusions

The following example demonstrates that high affinity interaction with the drug tracer with optimal signal to background is achieved when the expression of the NANOLUC fusion is close to endogenous level. As previously described, it was demonstrated that a 1:1000 dilution of the NANOLUC HDAC6 DNA with a carrier DNA was required to achieve a high affinity interaction. In this example, the expression of serial dilutions of the NANOLUC HDAC6 DNA was compared to the expression of the endogenous HDAC6 using western blot analysis.

HEK293 cells were seeded into wells of 6-well plates at $2.5 \times 10^5$ cells/well and transfected with PEI with varying amounts of NANOLUC HDAC6 DNA. The NANOLUC HDAC6 DNA was diluted with a non-expressing carrier DNA (pCI neo). The final concentration of DNA remained 2 ug/well while the NANOLUC HDAC6 DNA was diluted 1:0, 1:10, 1:100, 1:1000 and 1:10000. The control was un-transfected cells. 24 hours post transfection, the media was removed, and cells washed with PBS and lysed for 10 min with 400 ul of mammalian lysis buffer (Promega)+1:50 RQ1 DNase (Promega)+1× RQ1 buffer. Following lysis, 133 ul of 4λ SDS-loading buffer was added to each well, and the cell lysates were collected, analyzed on a SDS-PAGE gel and electro-transferred onto a PVDF membrane (Invitrogen). The membrane was blocked for 1 hour with 5% BSA (Promega) in TBS buffer and probed overnight at 4° C. with 1:500 dilution of HDAC6 antibody (Millipore) in TBS supplemented with 0.1% tween (TBST).

After 3× washes in TBST, the membrane was incubated with Anti-Rabbit HRP antibody (Jackson) in TBST for 1 hour, then washed 5× with TBST and 1× with TBS. The membrane was then incubated for 1 min with the ECL substrate from Promega and scanned on the Image Quant LAS4000 (GE). The results indicate that dilution of 1:1000 of the NANOLUC HDAC6 DNA results with expression level that is similar to the expression level of endogenous HDAC6. This is the same dilution that provided the high affinity interaction with the drug tracer with optimal signal to background.

Example 19

Quantification of Binding of Fluorescent Cytokines to a Fusion of a Cell Surface Receptor and NANOLUC Experiments were conducted during development of embodiments of the present invention to demonstrate the ability to measure the relative affinities of therapeutic antibodies against a cell surface receptor by competitive displacement of a fluorescently-labeled cytokine. In this example, commercially-available TAMRA-epidermal growth factor (TMR-EGF; Life Technologies) was applied in a cellular BRET assay using a stable cell line expressing a NANOLUC-EGFR (Her1) fusion protein. The BRET signal generated between TMR-EGF and NANOLUC-EGFR can be inhibited upon treatment with therapeutic antibodies known to interfere with binding of EGF.

A HEK293 stable cell line was generated by transfection of pF5 NANOLUC-EGFR plasmid DNA (Promega Corp.) and FuGene HD (Promega Corp.). After transfection, the stable cell line was generated by G418 selection, followed by limited dilution cloning. Clonally-derived cells expressing NANOLUC-EGFR were seeded into 96-well plates at a density of 20,000 cells per well. 20 hours after seeding, medium was replaced with serum-free OptiMEM and cells were serum starved. After starvation, cells were treated with serially-diluted TMR-EGF (Life Technologies). Following equilibration with the TMR-EGF, furimazine (a coelenterazine derivative substrate for NANOLUC; Promega Corp.) was added at a concentration of 20 uM, and BRET was quantified on a Varioskan luminometer. In subsequent experiments, antibody-mediated displacement of TMR-EGF was measured by pretreating cells with Vectibix, Erbitux, or Herceptin (negative control) prior to stimulation with TMR-EGF (long/mL final concentration).

Results in FIG. 20 demonstrate that the BRET can be used to quantify binding of fluorescent cytokines to cell surface receptors, tethered to NANOLUC. Furthermore, the affinities of therapeutic antibodies capable of inhibiting cytokine binding can be measured by competitive displacement of the fluorescent cytokine. Vectibix and Erbitux were capable of inhibiting the binding of TMR-EGF to NANOLUC-EGFR, whereas Herceptin (a Her2 binder with negligible affinity to Her1) were incapable of inhibiting TMR-EGF binding. This example demonstrates that the binding of a fluorescent cytokine to a known high-affinity target can be quantified by BRET, in a format that can be readily reconfigured to monitor binding of therapeutic antibodies (e.g. Vectibix, Erbitux, etc.) or other binders (e.g. cytokine biologics) by competitive displacement of the fluorescent cytokine. This demonstrates the ability to use BRET as a technique to measure the relative potencies of biologic drugs in a cellular format.

All publications and patents mentioned in the present application and/or listed below are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. A system comprising:
   (a) a bioactive agent conjugated to a fluorophore;
   (b) a cell that expresses a protein fusion of: (i) a protein of interest and (ii) a luciferase, wherein the bioactive agent is capable of binding non-covalently to the protein of interest upon interaction therewith, wherein the emission spectrum of the luciferase overlaps with the excitation spectrum of the fluorophore; and
   (c) a substrate for the luciferase.

2. The system of claim 1, wherein the bioactive agent is a peptide or nucleic acid.

3. The system of claim 2, wherein the nucleic acid is RNA.

4. The system of claim 2, wherein the nucleic acid is DNA.

5. The system of claim 1, wherein the fluorophore is a small molecule fluorophore.

6. The system of claim 5, wherein the small molecule fluorophore is a carboxy rhodamine analog.

7. The system of claim 1, wherein the luciferase comprises a polypeptide with at least 70% sequence identity with SEQ ID NO.: 1.

8. The system of claim 1, wherein the substrate for the luciferase is coelenterazine or a coelenterazine derivative.

9. The system of claim 8, wherein the substrate is 2-furanylmethyl-deoxy-coelenterazine.

10. The system of claim 1, wherein the bioactive agent conjugated to the fluorophore is within the cell.

11. The system of claim 1, wherein the conjugate of the bioactive agent and fluorophore is added extracellularly and enters the cell.

12. The system of claim 1, wherein the bioactive agent conjugated to the fluorophore is cell permeable.

13. The system of claim 12, further comprising a permeabilization agent to potentiate entry of the bioactive agent conjugated to the fluorophore into the cell.

14. The system of claim 1, wherein the bioactive agent conjugated to the fluorophore is part of a library of different non-small molecule bioactive agents tethered to fluorophores.

15. The system of claim 1, wherein the protein fusion is one of a plurality of different proteins of interest fused to luciferase.

16. The system of claim 1, wherein the non small molecule bioactive agent is produced by non-natural chemical synthesis.

17. The system of claim 1, wherein:
   (i) said luciferase has a first emission spectrum with a first peak emission;
   (ii) said fluorophore has an excitation spectrum that overlaps said first emission spectrum; and
   (iii) said fluorophore has a second emission spectrum with a second peak emission, said second peak emission being separated from said first peak emission.

18. The system of claim 17, wherein said second peak emission is separated from said first peak emission by at least 80 nm.

19. The system of claim 17, wherein the Forster distance of the fluorophore and luciferase pair is less than 20 nm.

20. The system of claim 19, wherein the Forster distance of the fluorophore and luciferase pair is less than 5 nm.

21. The system of claim 17, wherein upon binding of the bioactive agent to the protein of interest, conversion of the substrate to a reaction product by the luciferase results in excitation of the fluorophore by bioluminescence resonance energy transfer (BRET) and fluorescence emission from the fluorophore.

22. The system of claim 1, wherein upon binding of the bioactive agent to the protein of interest, conversion of the substrate to a reaction product by the luciferase results in excitation of the fluorophore by bioluminescence resonance energy transfer (BRET) and fluorescence emission from the fluorophore.

23. The system of claim 1, wherein the protein of interest of the fusion protein is displayed on the cell surface or the protein of interest of the fusion protein is intracellular and the bioactive agent conjugated to a fluorophore is cell permeable.

\* \* \* \* \*

SEQUENCE LISTING

```
<160> NUMBER OF SEQ ID NOS: 5

<210> SEQ ID NO 1
<211> LENGTH: 169
<212> TYPE: PRT
<213> ORGANISM: Oplophorus gracilirostris

<400> SEQUENCE: 1

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165
```

<210> SEQ ID NO 2
<211> LENGTH: 513
<212> TYPE: DNA
<213> ORGANISM: Artificial Sequence
<220> FEATURE:
<223> OTHER INFORMATION: Synthetic

<400> SEQUENCE: 2

| | | | | | | |
|---|---|---|---|---|---|---|
| atggtgttta | ccttggcaga | tttcgttgga | gactggcaac | agacagctgg | atacaaccaa | 60 |
| gatcaagtgt | tagaacaagg | aggattgtct | agtctgttcc | aagccctggg | agtgtcagtc | 120 |
| accccaatcc | agaaagttgt | gctgtctggg | gagaatgggt | taaaagctga | tattcatgtc | 180 |
| atcatccctt | acgagggact | cagtggtttt | caaatgggtc | tgattgaaat | gatcttcaaa | 240 |
| gttgtttacc | cagtggatga | tcatcatttc | aagattattc | tccattatgg | tacactcgtt | 300 |
| attgacggtg | tgacaccaaa | catgattgac | tactttggac | gcccttaccc | tggaattgct | 360 |
| gtgtttgacg | gcaagcagat | cacagttact | ggaactctgt | ggaacggcaa | caagatctat | 420 |
| gatgagcgcc | tgatcaaccc | agatggttca | ctcctcttcc | gcgttactat | caatggagtc | 480 |
| accggatggc | gcctttgcga | gaacattctt | gcc | | | 513 |

<210> SEQ ID NO 3
<211> LENGTH: 8414
<212> TYPE: DNA
<213> ORGANISM: Artificial Sequence
<220> FEATURE:
<223> OTHER INFORMATION: Synthetic

<400> SEQUENCE: 3

| | | | | | | |
|---|---|---|---|---|---|---|
| tcaatattgg | ccattagcca | tattattcat | tggttatata | gcataaatca | atattggcta | 60 |
| ttggccattg | catacgttgt | atctatatca | taatatgtac | atttatattg | gctcatgtcc | 120 |
| aatatgaccg | ccatgttggc | attgattatt | gactagttat | taatagtaat | caattacggg | 180 |
| gtcattagtt | catagcccat | atatggagtt | ccgcgttaca | taacttacgg | taaatggccc | 240 |
| gcctggctga | ccgcccaacg | acccccgccc | attgacgtca | ataatgacgt | atgttcccat | 300 |
| agtaacgcca | atagggactt | tccattgacg | tcaatgggtg | gagtatttac | ggtaaactgc | 360 |
| ccacttggca | gtacatcaag | tgtatcatat | gccaagtccg | cccccctattg | acgtcaatga | 420 |
| cggtaaatgg | cccgcctggc | attatgccca | gtacatgacc | ttacgggact | ttcctacttg | 480 |
| gcagtacatc | tacgtattag | tcatcgctat | taccatggtg | atgcggtttt | ggcagtacac | 540 |
| caatgggcgt | ggatagcggt | ttgactcacg | gggatttcca | agtctccacc | ccattgacgt | 600 |
| caatgggagt | ttgttttggc | accaaaatca | acgggacttt | ccaaaatgtc | gtaataaccc | 660 |
| cgccccgttg | acgcaaatgg | gcggtaggcg | tgtacggtgg | gaggtctata | taagcagagc | 720 |
| tggtttagtg | aaccgtcaga | tcactagaag | ctttattgcg | gtagtttatc | acagttaaat | 780 |
| tgctaacgca | gtcagtgctt | ctgacacaac | agtctcgaac | ttaagctgca | gaagttggtc | 840 |
| gtgaggcact | gggcaggtaa | gtatcaaggt | tacaagacag | gtttaaggag | accaatagaa | 900 |
| actgggcttg | tcgagacaga | gaagactctt | gcgtttctga | taggcaccta | ttggtcttac | 960 |
| tgacatccac | tttgcctttc | tctccacagg | tgtccactcc | cagttcaatt | acagctctta | 1020 |
| aggctagagt | attaatacga | ctcactatag | gctagcgct | caccatggtc | ttcacactcg | 1080 |
| aagatttcgt | tggggactgg | cgacagacag | ccggctacaa | cctggaccaa | gtccttgaac | 1140 |
| agggaggtgt | gtccagtttg | tttcagaatc | tcggggtgtc | cgtaactccg | atccaaagga | 1200 |
| ttgtcctgag | cggtgaaaat | gggctgaaga | tcgacatcca | tgtcatcatc | ccgtatgaag | 1260 |

```
gtctgagcgg cgaccaaatg ggccagatcg aaaaaatttt taaggtggtg taccctgtgg    1320
atgatcatca ctttaaggtg atcctgcact atggcacact ggtaatcgac ggggttacgc    1380
cgaacatgat cgactatttc ggacggccgt atgaaggcat cgccgtgttc gacggcaaaa    1440
agatcactgt aacagggacc ctgtggaacg gcaacaaaat tatcgacgag cgcctgatca    1500
accccgacgg ctccctgctg ttccgagtaa ccatcaacgg agtgaccggc tggcggctgt    1560
gcgaacgcat tctggcgggc tcgagcgcg cgatcgccat gacctcaacc ggccaggatt    1620
ccaccacaac caggcagcga agaagtaggc agaaccccca gtcgcccct caggactcca    1680 gtgtcacttc gaagcgaaat attaaaaagg gagccgttcc ccgctctatc cccaatctag    1740
cggaggtaaa gaagaaaggc aaaatgaaga agctcggcca agcaatggaa gaagacctaa    1800
tcgtgggact gcaagggatg gatctgaacc ttgaggctga agcactggct ggcactggct    1860
tggtgttgga tgagcagtta aatgaattcc attgcctctg ggatgacagc ttcccggaag    1920
gccctgagcg gctccatgcc atcaaggagc aactgatcca ggagggcctc ctagatcgct    1980
gcgtgtcctt tcaggcccgg tttgctgaaa aggaagagct gatgttggtt cacagcctag    2040
aatatattga tctgatggaa caacccagt acatgaatga gggagaactc cgtgtcctag    2100
cagacaccta cgactcagtt tatctgcatc cgaactcata ctcctgtgcc tgcctggcct    2160
caggctctgt cctcaggctg gtggatgcgt cctgggggc tgagatccgg aatggcatgg    2220
ccatcattag gcctcctgga catcacgccc agcacagtct tatggatggc tattgcatgt    2280
tcaaccacgt ggctgtggca gcccgctatg ctcaacagaa acaccgcatc cggagggtcc    2340
ttatcgtaga ttgggatgtg caccacggtc aaggaacaca gttcaccttc gaccaggacc    2400
ccagtgtcct ctatttctcc atccaccgct acgagcaggg taggttctgg ccccacctga    2460
aggcctctaa ctggtccacc acaggtttcg gccaaggcca aggatatacc atcaatgtgc    2520
cttggaacca ggtggggatg cgggatgctg actacattgc tgctttcctg cacgtcctgc    2580
tgccagtcgc cctcgagttc cagcctcagc tggtcctggt ggctgctgga tttgatgccc    2640
tgcaagggga ccccaagggt gagatggccg ccactccggc agggttcgcc cagctaaccc    2700
acctgctcat gggtctggca ggaggcaagc tgatcctgtc tctggagggt ggctacaacc    2760
tccgcgccct ggctgaaggc gtcagtgctt cgctccacac ccttctggga gacccttgcc    2820
ccatgctgga gtcacctggt gcccctgcc ggagtgccca ggcttcagtt tcctgtgctc    2880
tggaagccct tgagcccttc tgggaggttc ttgtgagatc aactgagacc gtggagaggg    2940
acaacatgga ggaggacaat gtagaggaga gcgaggagga aggaccctgg gagccccctg    3000
tgctcccaat cctgacatgg ccagtgctac agtctcgcac agggctggtc tatgaccaaa    3060
atatgatgaa tcactgcaac ttgtgggaca gccaccaccc tgaggtaccc cagcgcatct    3120
tgcggatcat gtgccgtctg gaggagctgg gccttgccgg gcgctgcctc accctgacac    3180
cgcgccctgc cacagaggct gagctgctca cctgtcacag tgctgagtac gtgggtcatc    3240
tccgggccac agagaaaatg aaaacccggg agctgcaccg tgagagttcc aactttgact    3300
ccatctatat ctgccccagt accttcgcct gtgcacagct tgccactggc gctgcctgcc    3360
gcctggtgga ggctgtgctc tcaggagagg ttctgaatgg tgctgctgtg gtgcgtcccc    3420
caggacacca cgcagagcag gatgcagctt gcggttttg cttttcaac tctgtggctg    3480 tggctgctcg ccatgcccag actatcagtg ggcatgccct acggatcctg attgtggatt    3540
gggatgtcca ccacggtaat ggaactcagc acatgtttga ggatgacccc agtgtgctat    3600
```

```
atgtgtccct gcaccgctat gatcatggca ccttcttccc catggggat gagggtgcca    3660 gcagccagat cggccgggct gcgggcacag gcttcaccgt caacgtggca tggaacgggc    3720
cccgcatggg tgatgctgac tacctagctg cctggcatcg cctggtgctt cccattgcct    3780
acgagtttaa cccagaactg gtgctggtct cagctggctt tgatgctgca cggggggatc    3840
cgctgggggg ctgccaggtg tcacctgagg gttatgccca cctcacccac ctgctgatgg    3900
gccttgccag tggccgcatt atccttatcc tagagggtgg ctataacctg acatccatct    3960
cagagtccat ggctgcctgc actcgctccc tccttggaga cccaccaccc ctgctgaccc    4020
tgccacggcc cccactatca ggggccctgg cctcaatcac tgagaccatc caagtccatc    4080
gcagatactg gcgcagctta cgggtcatga aggtagaaga cagagaagga ccctccagtt    4140
ctaagttggt caccaagaag gcaccccaac cagccaaacc taggttagct gagcggatga    4200
ccacacgaga aaagaaggtt ctggaagcag gcatgggaa agtcacctcg gcatcatttg    4260
gggaagagtc cactccaggc cagactaact cagagacagc tgtggtggcc ctcactcagg    4320
accagccctc agaggcagcc acaggggag ccactctggc ccagaccatt tctgaggcag    4380
ccattggggg agccatgctg ggccagacca cctcagagga ggctgtcggg ggagccactc    4440
cggaccagac cacctcagag gagactgtgg gaggagccat tctggaccag accacctcag    4500
aggatgctgt tgggggagcc acgctgggcc agactacctc agaggaggct gtaggaggag    4560
ctacactggc ccagaccacc tcggaggcag ccatggaggg agccacactg gaccagacta    4620
cgtcagagga ggctccaggg ggcaccgagc tgatccaaac tcctctagcc tcgagcacag    4680
accaccagac ccccccaacc tcacctgtgc agggaactac accccagata tctcccagta    4740
cactgattgg gagtctcagg accttggagc taggcagcga atctcagggg gcctcagaat    4800
ctcaggcccc aggagaggag aacctactag gagaggcagc tggaggtcag gacatggctg    4860
attcgatgct gatgcaggga tctaggggcc tcactgatca ggccatattt tatgctgtga    4920
caccactgcc ctggtgtccc catttggtgg cagtatgccc catacctgca gcaggcctag    4980
acgtgaccca accttgtggg gactgtggaa caatccaaga gaattgggtg tgtctctctt    5040
gctatcaggt ctactgtggt cgttacatca atggccacat gctccaacac catggaaatt    5100
ctggacaccc gctggtcctc agctacatcg acctgtcagc ctggtgttac tactgtcagg    5160
cctatgtcca ccaccaggct ctcctagatg tgaagaacat cgcccaccag aacaagtttg    5220
gggaggatat gccccaccca cacgtttaaa cgaattcggg ctcggtaccc ggggatcctc    5280
tagagtcgac ctgcaggcat gcaagctgat ccggctgcta acaaagcccg aaaggaagct    5340
gagttggctg ctgccaccgc tgagcaataa ctagcataac cccttggggc ggccgcttcg    5400
agcagacatg ataagataca ttgatgagtt tggacaaacc acaactagaa tgcagtgaaa    5460
aaaatgcttt atttgtgaaa tttgtgatgc tattgcttta tttgtaacca ttataagctg    5520
caataaacaa gttaacaaca caattgcat tcattttatg tttcaggttc aggggagat    5580 gtgggaggtt ttttaagca agtaaaacct ctacaaatgt ggtaaaatcg aattttaaca    5640
aaatattaac gcttacaatt tcctgatgcg gtattttctc cttacgcatc tgtgcggtat    5700
ttcacaccgc atacgcggat ctgcgcagca ccatggcctg aaataacctc tgaaagagga    5760
acttggttag gtaccttctg aggcggaaag aaccagctgt ggaatgtgtg tcagttaggg    5820
tgtggaaagt ccccaggctc cccagcaggc agaagtatgc aaagcatgca tctcaattag    5880
tcagcaacca ggtgtggaaa gtccccaggc tccccagcag gcagaagtat gcaaagcatg    5940
catctcaatt agtcagcaac catagtcccg cccctaactc cgcccatccc gcccctaact    6000
```

```
ccgcccagtt ccgcccattc tccgcccat  ggctgactaa ttttttttat ttatgcagag  6060
gccgaggccg cctcggcctc tgagctattc cagaagtagt gaggaggctt ttttggaggc  6120
ctaggctttt gcaaaaagct taattaactg ttgacaatta atcatcggca tagtatatcg  6180
gcatagtata atacgacaag gtgaggaact aaacccagga ggcagatcat gattgaacaa  6240
gatggattgc acgcaggttc tccggccgct tgggtggaga ggctattcgg ctatgactgg  6300
gcacaacaga caatcggctg ctctgatgcc gccgtgttcc ggctgtcagc gcaggggcgc  6360
ccggttcttt ttgtcaagac cgacctgtcc ggtgccctga atgaactgca ggacgaggca  6420
gcgcggctat cgtggctggc cacgacgggc gttccttgcg cagctgtgct cgacgttgtc  6480
actgaagcgg gaagggactg gctgctattg ggcgaagtgc cggggcagga tctcctgtca  6540
tctcaccttg ctcctgccga gaaagtatcc atcatggctg atgcaatgcg gcggctgcat  6600
acgcttgatc cggctacctg cccattcgac caccaagcga acatcgcat  cgagcgagca  6660
cgtactcgga tggaagccgg tcttgtcgat caggatgatc tggacgaaga gcatcagggg  6720
ctcgcgccag ccgaactgtt cgccaggctc aaggcgcgca tgcccgacgg cgaggatctc  6780
gtcgtgaccc atggcgatgc ctgcttgccg aatatcatgg tggaaaatgg ccgcttttct  6840
ggattcatcg actgtggccg gctgggtgtg gcggaccgct atcaggacat agcgttggct  6900
acccgtgata ttgctgaaga gcttggcggc gaatgggctg accgcttcct cgtgctttac  6960
ggtatcgccg ctcccgattc gcagcgcatc gccttctatc gccttcttga cgagttcttc  7020
tgagcgggac tctggggttc gaaatgaccg accaagcgac gcccaacctg ccatcacgat  7080
ggccgcaata aaatatcttt attttcatta catctgtgtg ttggtttttt gtgtgaatcg  7140
atagcgataa ggatcctctt tgcgcttgcg ttttcccttg tccagatagc ccagtagctg  7200
acattcatcc ggggtcagca ccgtttctgc ggactggctt tctacccggt atcagctcac  7260
tcaaaggcgg taatacggtt atccacagaa tcagggata  acgcaggaaa gaacatgtga  7320
gcaaaaggcc agcaaaaggc caggaaccgt aaaaaggccg cgttgctggc gttttccat   7380
aggctccgcc cccctgacga gcatcacaaa aatcgacgct caagtcagag gtggcgaaac  7440
ccgacaggac tataaagata ccaggcgttt ccccctggaa gctccctcgt gcgctctcct  7500
gttccgaccc tgccgcttac cggatacctg tccgcctttc tcccttcggg aagcgtggcg  7560
ctttctcata gctcacgctg taggtatctc agttcggtgt aggtcgttcg ctccaagctg  7620
ggctgtgtgc acgaaccccc cgttcagccc gaccgctgcg ccttatccgg taactatcgt  7680
cttgagtcca acccggtaag acacgactta tcgccactgg cagcagccac tggtaacagg  7740
attagcagag cgaggtatgt aggcggtgct acagagttct tgaagtggtg gcctaactac  7800
ggctacacta gaaggacagt atttggtatc tgcgctctgc tgaagccagt taccttcgga  7860
aaaagagttg gtagctcttg atccggcaaa caaaccaccg ctggtagcgg tggtttttt   7920
gtttgcaagc agcagattac gcgcagaaaa aaaggatttc aagaagatcc tttgatcttt  7980
tctacggggt ctgacgctca gtggaacgaa aactcacgtt aagggatttt ggtcatgaga  8040
ttatcaaaaa ggatcttcac ctagatcctt ttatagtccg aaatacagg  aacgcacgct  8100
ggatggccct tcgctgggat ggtgaaacca tgaaaaatgg cagcttcagt ggattaagtg  8160
ggggtaatgt ggcctgtacc ctctggttgc ataggtattc atacggttaa atttatcag   8220
gcgcgattgc ggcagttttt cggtggtttt gttgccattt ttacctgtct gctgccgtga  8280
tcgcgctgaa cgcgttttag cggtgcgtac aattaaggga ttatggtaaa tccacttact  8340
```

| | |
|---|---|
| gtctgccctc gtagccatcg agataaaccg cagtactccg gccacgatgc gtccggcgta | 8400 |
| gaggatcgag atct | 8414 |

```
<210> SEQ ID NO 4
<211> LENGTH: 4185
<212> TYPE: DNA
<213> ORGANISM: Artificial Sequence
<220> FEATURE:
<223> OTHER INFORMATION: Synthetic

<400> SEQUENCE: 4
```

| | |
|---|---|
| atggtcttca cactcgaaga tttcgttggg gactggcgac agacagccgg ctacaacctg | 60 |
| gaccaagtcc ttgaacaggg aggtgtgtcc agtttgtttc agaatctcgg ggtgtccgta | 120 |
| actccgatcc aaaggattgt cctgagcggt gaaaatgggc tgaagatcga catccatgtc | 180 |
| atcatcccgt atgaaggtct gagcggcgac caaatgggcc agatcgaaaa aattttaag | 240 |
| gtggtgtacc ctgtggatga tcatcacttt aaggtgatcc tgcactatgg cacactggta | 300 |
| atcgacgggg ttacgccgaa catgatcgac tatttcggac ggccgtatga aggcatcgcc | 360 |
| gtgttcgacg gcaaaaagat cactgtaaca gggaccctgt ggaacggcaa caaaattatc | 420 |
| gacgagcgcc tgatcaaccc cgacggctcc ctgctgttcc gagtaaccat caacggagtg | 480 |
| accggctggc ggctgtgcga acgcattctg gcgggctcga gcggcgcgat cgccatgacc | 540 |
| tcaaccggcc aggattccac cacaaccagg cagcgaagaa gtaggcagaa cccccagtcg | 600 |
| cccctcagg actccagtgt cacttcgaag cgaaatatta aaagggagc cgttccccgc | 660 |
| tctatcccca atctagcgga ggtaaagaag aaggcaaaa tgaagaagct cggccaagca | 720 |
| atggaagaag acctaatcgt gggactgcaa gggatggatc tgaaccttga ggctgaagca | 780 |
| ctggctggca ctggccttgt gttggatgag cagttaaatg aattccattg cctctgggat | 840 |
| gacagcttcc cggaaggccc tgagcggctc catgccatca ggagcaact gatccaggag | 900 |
| ggcctcctag atcgctgcgt gtcctttcag gcccggtttg ctgaaaagga gagctgatg | 960 |
| ttggttcaca gcctagaata tattgatctg atggaaacaa cccagtacat gaatgaggga | 1020 |
| gaactccgtg tcctagcaga cacctacgac tcagtttatc tgcatccgaa ctcatactcc | 1080 |
| tgtgcctgcc tggcctcagg ctctgtcctc aggctggtgg atgcggtcct gggggctgag | 1140 |
| atccggaatg gcatggccat cattaggcct cctggacatc acgcccagca cagtcttatg | 1200 |
| gatggctatt gcatgttcaa ccacgtggct gtggcagccc gctatgctca acagaaacac | 1260 |
| cgcatccgga gggtccttat cgtagattgg gatgtgcacc acggtcaagg aacacagttc | 1320 |
| accttcgacc aggaccccag tgtcctctat ttctccatcc accgctacga gcagggtagg | 1380 |
| ttctggcccc acctgaaggc ctctaactgg tccaccacag gtttcggcca aggccaagga | 1440 |
| tataccatca atgtgccttg gaaccaggtg gggatgcggg atgctgacta cattgctgct | 1500 |
| ttcctgcacg tcctgctgcc agtcgccctc gagttccagc ctcagctggt cctggtggct | 1560 |
| gctggatttg atgccctgca aggggacccc aagggtgaga tggccgccac tccggcaggg | 1620 |
| ttcgcccagc taacccacct gctcatgggt ctggcaggag gcaagctgat cctgtctctg | 1680 |
| gagggtggct acaacctccg cgccctggct gaaggcgtca gtgcttcgct ccacacctt | 1740 |
| ctgggagacc cttgccccat gctggagtca cctggtgccc cctgccggag tgcccaggct | 1800 |
| tcagtttcct gtgctctgga agcccttgag cccttctggg aggttcttgt gagatcaact | 1860 |
| gagaccgtgg agagggacaa catggaggag acaatgtag aggagagcga ggaggaagga | 1920 |
| ccctgggagc cccctgtgct cccaatcctg acatggccag tgctacagtc tcgcacaggg | 1980 |

```
ctggtctatg accaaaatat gatgaatcac tgcaacttgt gggacagcca ccaccctgag    2040
gtaccccagc gcatcttgcg gatcatgtgc cgtctggagg agctgggcct tgccgggcgc    2100
tgcctcaccc tgacaccgcg ccctgccaca gaggctgagc tgctcacctg tcacagtgct    2160
gagtacgtgg gtcatctccg ggccacagag aaaatgaaaa cccgggagct gcaccgtgag    2220
agttccaact ttgactccat ctatatctgc cccagtacct tcgcctgtgc acagcttgcc    2280
actggcgctg cctgccgcct ggtggaggct gtgctctcag agaggttct  gaatggtgct    2340 gctgtggtgc gtcccccagg acaccacgca gagcaggatg cagcttgcgg tttttgcttt    2400
ttcaactctg tggctgtggc tgctcgccat gcccagacta tcagtgggca tgccctacgg    2460
atcctgattg tggattggga tgtccaccac ggtaatggaa ctcagcacat gtttgaggat    2520
gaccccagtg tgctatatgt gtccctgcac cgctatgatc atggcacctt cttccccatg    2580
ggggatgagg gtgccagcag ccagatcggc cgggctgcgg gcacaggctt caccgtcaac    2640
gtggcatgga acgggcccg catggtgat gctgactacc tagctgcctg gcatcgcctg    2700
gtgcttccca ttgcctacga gtttaaccca gaactggtgc tggtctcagc tggctttgat    2760
gctgcacggg gggatccgct gggggctgc caggtgtcac ctgagggtta tgcccacctc    2820
acccacctgc tgatgggcct tgccagtggc cgcattatcc ttatcctaga gggtggctat    2880
aacctgacat ccatctcaga gtccatggct gcctgcactc gctccctcct ggagaccca    2940 ccaccctgc tgaccctgcc acggccccca ctatcagggg ccctggcctc aatcactgag    3000
accatccaag tccatcgcag atactggcgc agcttacggg tcatgaaggt agaagacaga    3060
gaaggaccct ccagttctaa gttggtcacc aagaaggcac cccaaccagc caaacctagg    3120
ttagctgagc ggatgaccac acgagaaaag aaggttctgg aagcaggcat ggggaaagtc    3180
acctcggcat catttgggga agagtccact ccaggccaga ctaactcaga gacagctgtg    3240
gtggccctca ctcaggacca gccctcgagg gcagccacag ggggagccac tctggcccag    3300
accatttctg aggcagccat tgggggagcc atgctgggcc agaccacctc agaggaggct    3360
gtcgggggag ccactccgga ccagaccacc tcagaggaga ctgtgggagg agccattctg    3420
gaccagacca cctcagagga tgctgttggg ggagccacgc tgggcagac tacctcagag    3480 gaggctgtag gaggagctac actggcccag accacctcgg aggcagccat ggagggagcc    3540
acactggacc agactacgtc agaggaggct ccagggggca ccgagctgat ccaaactcct    3600
ctagcctcga gcacagacca ccagaccccc ccaacctcac ctgtgcaggg aactacaccc    3660
cagatatctc ccagtacact gattgggagt ctcaggacct tggagctagg cagcgaatct    3720
cagggggcct cagaatctca ggccccagga gaggagaacc tactaggaga ggcagctgga    3780
ggtcaggaca tggctgattc gatgctgatg cagggatcta ggggcctcac tgatcaggcc    3840
atattttatg ctgtgacacc actgccctgg tgtccccatt tggtggcagt atgccccata    3900
cctgcagcag gcctagacgt gacccaacct tgtggggact gtggaacaat ccaagagaat    3960
tgggtgtgtc tctcttgcta tcaggtctac tgtggtcgtt acatcaatgg ccacatgctc    4020
caacaccatg gaaattctgg acacccgctg gtcctcagct acatcgacct gtcagcctgg    4080
tgttactact gtcaggccta tgtccaccac caggctctcc tagatgtgaa gaacatcgcc    4140
caccagaaca gtttgggga ggatatgccc cacccacacg tttaa              4185
```

<210> SEQ ID NO 5
<211> LENGTH: 1394
<212> TYPE: PRT

<213> ORGANISM: Artificial Sequence
<220> FEATURE:
<223> OTHER INFORMATION: Synthetic

<400> SEQUENCE: 5

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala Gly Ser Ser Gly Ala
                165                 170                 175

Ile Ala Met Thr Ser Thr Gly Gln Asp Ser Thr Thr Thr Arg Gln Arg
            180                 185                 190

Arg Ser Arg Gln Asn Pro Gln Ser Pro Pro Gln Asp Ser Ser Val Thr
        195                 200                 205

Ser Lys Arg Asn Ile Lys Lys Gly Ala Val Pro Arg Ser Ile Pro Asn
210                 215                 220

Leu Ala Glu Val Lys Lys Lys Gly Lys Met Lys Lys Leu Gly Gln Ala
225                 230                 235                 240

Met Glu Glu Asp Leu Ile Val Gly Leu Gln Gly Met Asp Leu Asn Leu
                245                 250                 255

Glu Ala Glu Ala Leu Ala Gly Thr Gly Leu Val Leu Asp Glu Gln Leu
            260                 265                 270

Asn Glu Phe His Cys Leu Trp Asp Asp Ser Phe Pro Glu Gly Pro Glu
        275                 280                 285

Arg Leu His Ala Ile Lys Glu Gln Leu Ile Gln Glu Gly Leu Leu Asp
290                 295                 300

Arg Cys Val Ser Phe Gln Ala Arg Phe Ala Glu Lys Glu Glu Leu Met
305                 310                 315                 320

Leu Val His Ser Leu Glu Tyr Ile Asp Leu Met Glu Thr Thr Gln Tyr
                325                 330                 335

Met Asn Glu Gly Glu Leu Arg Val Leu Ala Asp Thr Tyr Asp Ser Val
            340                 345                 350

Tyr Leu His Pro Asn Ser Tyr Ser Cys Ala Cys Leu Ala Ser Gly Ser
        355                 360                 365

Val Leu Arg Leu Val Asp Ala Val Leu Gly Ala Glu Ile Arg Asn Gly
370                 375                 380

Met Ala Ile Ile Arg Pro Pro Gly His His Ala Gln His Ser Leu Met
```

-continued

```
            385                 390                 395                 400
        Asp Gly Tyr Cys Met Phe Asn His Val Ala Val Ala Ala Arg Tyr Ala
                        405                 410                 415
        Gln Gln Lys His Arg Ile Arg Val Leu Ile Val Asp Trp Asp Val
                    420                 425                 430
        His His Gly Gln Gly Thr Gln Phe Thr Phe Asp Gln Asp Pro Ser Val
                        435                 440                 445
        Leu Tyr Phe Ser Ile His Arg Tyr Glu Gln Gly Arg Phe Trp Pro His
            450                 455                 460
        Leu Lys Ala Ser Asn Trp Ser Thr Thr Gly Phe Gly Gln Gly Gln Gly
        465                 470                 475                 480
        Tyr Thr Ile Asn Val Pro Trp Asn Gln Val Gly Met Arg Asp Ala Asp
                        485                 490                 495
        Tyr Ile Ala Ala Phe Leu His Val Leu Leu Pro Val Ala Leu Glu Phe
                        500                 505                 510
        Gln Pro Gln Leu Val Leu Val Ala Ala Gly Phe Asp Ala Leu Gln Gly
                    515                 520                 525
        Asp Pro Lys Gly Glu Met Ala Ala Thr Pro Ala Gly Phe Ala Gln Leu
                530                 535                 540
        Thr His Leu Leu Met Gly Leu Ala Gly Gly Lys Leu Ile Leu Ser Leu
        545                 550                 555                 560
        Glu Gly Gly Tyr Asn Leu Arg Ala Leu Ala Glu Gly Val Ser Ala Ser
                        565                 570                 575
        Leu His Thr Leu Leu Gly Asp Pro Cys Pro Met Leu Glu Ser Pro Gly
                    580                 585                 590
        Ala Pro Cys Arg Ser Ala Gln Ala Ser Val Ser Cys Ala Leu Glu Ala
                    595                 600                 605
        Leu Glu Pro Phe Trp Glu Val Leu Val Arg Ser Thr Glu Thr Val Glu
                610                 615                 620
        Arg Asp Asn Met Glu Glu Asp Asn Val Glu Glu Ser Glu Glu Glu Gly
        625                 630                 635                 640
        Pro Trp Glu Pro Pro Val Leu Pro Ile Leu Thr Trp Pro Val Leu Gln
                        645                 650                 655
        Ser Arg Thr Gly Leu Val Tyr Asp Gln Asn Met Met Asn His Cys Asn
                    660                 665                 670
        Leu Trp Asp Ser His His Pro Glu Val Pro Gln Arg Ile Leu Arg Ile
                    675                 680                 685
        Met Cys Arg Leu Glu Glu Leu Gly Leu Ala Gly Arg Cys Leu Thr Leu
                690                 695                 700
        Thr Pro Arg Pro Ala Thr Glu Ala Glu Leu Leu Thr Cys His Ser Ala
        705                 710                 715                 720
        Glu Tyr Val Gly His Leu Arg Ala Thr Glu Lys Met Lys Thr Arg Glu
                        725                 730                 735
        Leu His Arg Glu Ser Ser Asn Phe Asp Ser Ile Tyr Ile Cys Pro Ser
                    740                 745                 750
        Thr Phe Ala Cys Ala Gln Leu Ala Thr Gly Ala Ala Cys Arg Leu Val
                    755                 760                 765
        Glu Ala Val Leu Ser Gly Glu Val Leu Asn Gly Ala Ala Val Val Arg
                770                 775                 780
        Pro Pro Gly His His Ala Glu Gln Asp Ala Ala Cys Gly Phe Cys Phe
        785                 790                 795                 800
        Phe Asn Ser Val Ala Val Ala Ala Arg His Ala Gln Thr Ile Ser Gly
                        805                 810                 815
```

```
His Ala Leu Arg Ile Leu Ile Val Asp Trp Asp Val His His Gly Asn
            820                 825                 830

Gly Thr Gln His Met Phe Glu Asp Asp Pro Ser Val Leu Tyr Val Ser
            835                 840                 845

Leu His Arg Tyr Asp His Gly Thr Phe Phe Pro Met Gly Asp Glu Gly
    850                 855                 860

Ala Ser Ser Gln Ile Gly Arg Ala Ala Gly Thr Gly Phe Thr Val Asn
865                 870                 875                 880

Val Ala Trp Asn Gly Pro Arg Met Gly Asp Ala Asp Tyr Leu Ala Ala
                885                 890                 895

Trp His Arg Leu Val Leu Pro Ile Ala Tyr Glu Phe Asn Pro Glu Leu
                900                 905                 910

Val Leu Val Ser Ala Gly Phe Asp Ala Ala Arg Gly Asp Pro Leu Gly
            915                 920                 925

Gly Cys Gln Val Ser Pro Glu Gly Tyr Ala His Leu Thr His Leu Leu
    930                 935                 940

Met Gly Leu Ala Ser Gly Arg Ile Ile Leu Ile Leu Glu Gly Gly Tyr
945                 950                 955                 960

Asn Leu Thr Ser Ile Ser Glu Ser Met Ala Ala Cys Thr Arg Ser Leu
                965                 970                 975

Leu Gly Asp Pro Pro Pro Leu Leu Thr Leu Pro Arg Pro Pro Leu Ser
            980                 985                 990

Gly Ala Leu Ala Ser Ile Thr Glu  Thr Ile Gln Val His Arg Arg Tyr
        995                 1000                1005

Trp Arg  Ser Leu Arg Val Met  Lys Val Glu Asp Arg  Glu Gly Pro
   1010                 1015                1020

Ser Ser  Ser Lys Leu Val Thr  Lys Lys Ala Pro Gln  Pro Ala Lys
   1025                 1030                1035

Pro Arg  Leu Ala Glu Arg Met  Thr Thr Arg Glu Lys  Lys Val Leu
   1040                 1045                1050

Glu Ala  Gly Met Gly Lys Val  Thr Ser Ala Ser Phe  Gly Glu Glu
   1055                 1060                1065

Ser Thr  Pro Gly Gln Thr Asn  Ser Glu Thr Ala Val  Val Ala Leu
   1070                 1075                1080

Thr Gln  Asp Gln Pro Ser Glu  Ala Ala Thr Gly Gly  Ala Thr Leu
   1085                 1090                1095

Ala Gln  Thr Ile Ser Glu Ala  Ala Ile Gly Gly Ala  Met Leu Gly
   1100                 1105                1110

Gln Thr  Thr Ser Glu Glu Ala  Val Gly Gly Ala Thr  Pro Asp Gln
   1115                 1120                1125

Thr Thr  Ser Glu Glu Thr Val  Gly Gly Ala Ile Leu  Asp Gln Thr
   1130                 1135                1140

Thr Ser  Glu Asp Ala Val Gly  Gly Ala Thr Leu Gly  Gln Thr Thr
   1145                 1150                1155

Ser Glu  Glu Ala Val Gly Gly  Ala Thr Leu Ala Gln  Thr Thr Ser
   1160                 1165                1170

Glu Ala  Ala Met Glu Gly Ala  Thr Leu Asp Gln Thr  Thr Ser Glu
   1175                 1180                1185

Glu Ala  Pro Gly Gly Thr Glu  Leu Ile Gln Thr Pro  Leu Ala Ser
   1190                 1195                1200

Ser Thr  Asp His Gln Thr Pro  Thr Ser Pro Val Gln  Gly Thr
   1205                 1210                1215
```

```
Thr Pro Gln Ile Ser Pro Ser Thr Leu Ile Gly Ser Leu Arg Thr
    1220            1225                1230

Leu Glu Leu Gly Ser Glu Ser Gln Gly Ala Ser Glu Ser Gln Ala
    1235            1240                1245

Pro Gly Glu Glu Asn Leu Leu Gly Glu Ala Ala Gly Gly Gln Asp
    1250            1255                1260

Met Ala Asp Ser Met Leu Met Gln Gly Ser Arg Gly Leu Thr Asp
    1265            1270                1275

Gln Ala Ile Phe Tyr Ala Val Thr Pro Leu Pro Trp Cys Pro His
    1280            1285                1290

Leu Val Ala Val Cys Pro Ile Pro Ala Ala Gly Leu Asp Val Thr
    1295            1300                1305

Gln Pro Cys Gly Asp Cys Gly Thr Ile Gln Glu Asn Trp Val Cys
    1310            1315                1320

Leu Ser Cys Tyr Gln Val Tyr Cys Gly Arg Tyr Ile Asn Gly His
    1325            1330                1335

Met Leu Gln His His Gly Asn Ser Gly His Pro Leu Val Leu Ser
    1340            1345                1350

Tyr Ile Asp Leu Ser Ala Trp Cys Tyr Tyr Cys Gln Ala Tyr Val
    1355            1360                1365

His His Gln Ala Leu Leu Asp Val Lys Asn Ile Ala His Gln Asn
    1370            1375                1380

Lys Phe Gly Glu Asp Met Pro His Pro His Val
    1385            1390
```